US011581491B2

(12) United States Patent
Jatsch et al.

(10) Patent No.: US 11,581,491 B2
(45) Date of Patent: Feb. 14, 2023

(54) MATERIALS FOR ORGANIC ELECTROLUMINESCENT DEVICES

(71) Applicant: Merck Patent GmbH, Darmstadt (DE)

(72) Inventors: Anja Jatsch, Frankfurt am Main (DE); Amir Hossain Parham, Frankfurt am Main (DE); Thomas Eberle, Landau (DE); Tobias Grossmann, Darmstadt (DE); Jonas Valentin Kroeber, Frankfurt am Main (DE)

(73) Assignee: MERCK PATENT GMBH, Darmstadt (DE)

( * ) Notice: Subject to any disclaimer, the term of this patent is extended or adjusted under 35 U.S.C. 154(b) by 471 days.

(21) Appl. No.: 15/756,783

(22) PCT Filed: Aug. 12, 2016

(86) PCT No.: PCT/EP2016/001391
§ 371 (c)(1),
(2) Date: Mar. 1, 2018

(87) PCT Pub. No.: WO2017/041874
PCT Pub. Date: Mar. 16, 2017

(65) Prior Publication Data
US 2018/0269400 A1   Sep. 20, 2018

(30) Foreign Application Priority Data

Sep. 8, 2015  (EP) .................................... 15184191

(51) Int. Cl.
| H01L 51/00 | (2006.01) |
|---|---|
| C09K 11/06 | (2006.01) |
| C07D 209/94 | (2006.01) |
| C07D 405/12 | (2006.01) |
| C07D 409/12 | (2006.01) |
| C07D 409/14 | (2006.01) |
| C07D 405/14 | (2006.01) |
| C07D 209/08 | (2006.01) |
| C07D 401/10 | (2006.01) |
| C07D 405/10 | (2006.01) |
| C07D 409/10 | (2006.01) |
| C07D 403/10 | (2006.01) |
| C07D 209/10 | (2006.01) |
| C07D 491/04 | (2006.01) |
| H01L 51/50 | (2006.01) |

(52) U.S. Cl.
CPC ........ *H01L 51/0061* (2013.01); *C07D 209/08* (2013.01); *C07D 209/10* (2013.01); *C07D 209/94* (2013.01); *C07D 401/10* (2013.01); *C07D 403/10* (2013.01); *C07D 405/10* (2013.01); *C07D 405/12* (2013.01); *C07D 405/14* (2013.01); *C07D 409/10* (2013.01); *C07D 409/12* (2013.01); *C07D 409/14* (2013.01); *C07D 491/04* (2013.01); *C09K 11/06* (2013.01); *H01L 51/006* (2013.01); *H01L 51/0072* (2013.01); *H01L 51/0073* (2013.01); *C09K 2211/1018* (2013.01); *H01L 51/0052* (2013.01); *H01L 51/0054* (2013.01); *H01L 51/0056* (2013.01); *H01L 51/0058* (2013.01); *H01L 51/0074* (2013.01); *H01L 51/5016* (2013.01); *H01L 51/5056* (2013.01); *H01L 51/5088* (2013.01); *H01L 51/5096* (2013.01)

(58) Field of Classification Search
None
See application file for complete search history.

(56) References Cited

U.S. PATENT DOCUMENTS

| 9,978,949 B2 | 5/2018 | Mujica-Fernaud et al. |
|---|---|---|
| 2012/0299473 A1 | 11/2012 | Mizutani et al. |
| 2013/0126856 A1* | 5/2013 | Yokoyama ........... C07D 401/10 257/40 |
| 2015/0155498 A1 | 6/2015 | Ahn et al. |
| 2015/0318478 A1 | 11/2015 | Pflumm et al. |

FOREIGN PATENT DOCUMENTS

| CN | 102448946 A | 5/2012 |
|---|---|---|
| CN | 103038215 A | 4/2013 |
| CN | 103477462 A | 12/2013 |
| CN | 103842339 A | 6/2014 |
| CN | 104334682 A | 2/2015 |
| CN | 104837808 A | 8/2015 |
| EP | 2599773 A1 | 6/2013 |
| JP | 2012528088 A | 11/2012 |
| KR | 20110117548 A | 10/2011 |
| TW | 201425305 A | 7/2014 |
| WO | WO-2011037429 A2 | 3/2011 |
| WO | WO-2011096506 A1 | 8/2011 |
| WO | WO-2012/014500 A1 * | 2/2012 |
| WO | 2012/089294 A1 | 7/2012 |

(Continued)

OTHER PUBLICATIONS

International Search Report for PCT/EP2016/001391 dated Nov. 2, 2016.
Written Opinion of the International Searching Authority for PCT/EP2016/001391 dated Nov. 2, 2016.
International Preliminary Report on Patentability received for PCT Patent Application No. PCT/EP2016/001391, dated Mar. 22, 2018, 13 pages (8 pages of English Translation and 5 pages of Original Document).

(Continued)

*Primary Examiner* — Jay Yang
(74) *Attorney, Agent, or Firm* — Faegre Drinker Biddle & Reath LLP

(57) ABSTRACT

The present invention relates to compounds suitable for use in electronic devices, and to electronic devices, especially organic electroluminescent devices, comprising these compounds.

6 Claims, No Drawings

(56) References Cited

FOREIGN PATENT DOCUMENTS

WO        2014/020444 A2    2/2014
WO   WO-2014204464 A1   12/2014

OTHER PUBLICATIONS

International Search Report and Written Opinion received for PCT Patent Application No. PCT/EP2016/001391, dated Nov. 2, 2016, 16 pages (7 pages of English Translation and 9 pages of Original Document).

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2016/001391, filed Aug. 12, 2016, which claims benefit of European Application No. 15184191.3, filed Sep. 8, 2015, both of which are incorporated herein by reference in their entirety.

The present invention relates to materials for use in electronic devices, especially in organic electroluminescent devices, and to electronic devices, especially organic electroluminescent devices, comprising these materials.

Emitting materials used in organic electroluminescent devices (OLEDs) are frequently organometallic complexes which exhibit phosphorescence rather than fluorescence. In general terms, however, there is still a need for improvement in OLEDs, especially also in OLEDs which exhibit triplet emission (phosphorescence), for example with regard to efficiency, operating voltage and lifetime. The properties of phosphorescent OLEDs are not just determined by the triplet emitters used. More particularly, the other materials used, especially also the matrix materials, are also of particular significance here. Improvements to these materials can thus also lead to distinct improvements in the OLED properties.

According to the prior art, matrix materials used for phosphorescent emitters in organic electroluminescent devices include indenocarbazole derivatives, for example according to WO 2010/136109, WO 2012/014500 or WO 2013/041176, for example indenocarbazole derivatives substituted by diarylamino groups or triarylamino groups. In the materials disclosed in these documents, further improvements are desirable, especially in relation to lifetime.

The problem addressed by the present invention is that of providing improved indenocarbazole materials which are especially suitable for use as matrix material for phosphorescent emitters.

It has been found that, surprisingly, particular compounds described in detail below solve this problem and are of good suitability for use in OLEDs and lead to improvements in the organic electroluminescent device, the improvements relating especially to lifetime. These materials are indenocarbazole compounds having a triarylamine substituent, where the amine is substituted by a 1-, 3- or 4-fluorenyl group, a 1-, 3- or 4-dibenzofuran group or a 1-, 3- or 4-dibenzothiophene group. The present invention therefore provides these compounds and electronic devices, especially organic electroluminescent devices, comprising such compounds.

The present invention therefore provides a compound of the following formula (1):

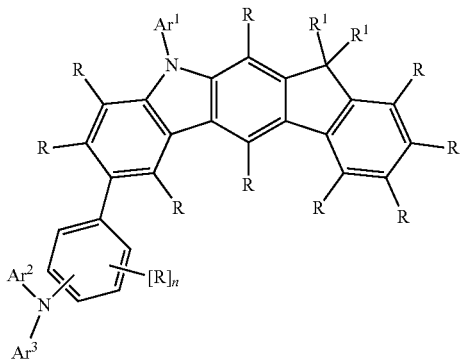

Formula (1)

where the symbols and indices used are as follows:

$Ar^1$, $Ar^2$ is the same or different at each instance and is an aromatic or heteroaromatic ring system which has 5 to 30 aromatic ring atoms and may be substituted by one or more R radicals, preferably nonaromatic R radicals;

$Ar^3$ is a group of the following formula (2):

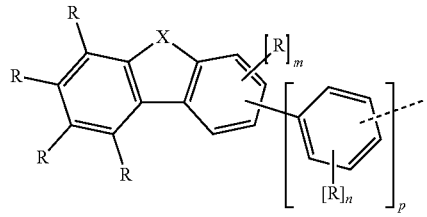

Formula (2)

where the dotted bond indicates the linkage of this group to the nitrogen atom and the fluorene or dibenzofuran or dibenzothiophene group is joined to the phenylene group via the 1, 3 or 4 position where p=1 and to the nitrogen atom when p=0;

X is $C(R^1)_2$, O or S;

R, $R^1$ is the same or different at each instance and is selected from the group consisting of H, D, F, Cl, Br, I, CN, $NO_2$, $N(R^2)_2$, $OR^2$, $SR^2$, $C(=O)R^2$, $P(=O)R^2$, $Si(R^2)_3$, a straight-chain alkyl group having 1 to 20 carbon atoms or a branched or cyclic alkyl group having 3 to 20 carbon atoms or an alkenyl or alkynyl group having 2 to 20 carbon atoms, where the alkyl, alkenyl or alkynyl group may be substituted in each case by one or more $R^2$ radicals and where one or more nonadjacent $CH_2$ groups may be replaced by $R^2C=CR^2$, $C\equiv C$, $Si(R^2)_2$, $C=O$, $C=NR^2$, $P(=O)(R^2)$, SO, $SO_2$, $NR^2$, O, S or $CONR^2$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^2$ radicals; at the same time, it is optionally possible for two adjacent R substituents or two adjacent $R^1$ substituents to form a monocyclic or polycyclic, aliphatic, aromatic or heteroaromatic ring system which may be substituted by one or more $R^2$ radicals;

$R^2$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, CN or an alkyl group having 1 to 10 carbon atoms, where two or more adjacent $R^2$ substituents together may form a mono- or polycyclic, aliphatic ring system;

m is 0, 1, 2 or 3;

n is the same or different at each instance and is 0, 1, 2, 3 or 4;

p is 0 or 1.

For the sake of clarity, the numbering of the carbon atoms in the fluorene or dibenzofuran or dibenzothiophene used in this application, as occurs in the structure of the formula (2), is shown below:

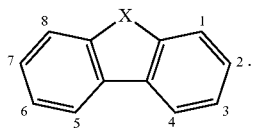

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. The heteroaryl group here preferably contains not more than three heteroatoms, of which not more than one is selected from O and S and the further heteroatoms are N. An aryl group or heteroaryl group is understood here to mean either a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl or bipyridine, by contrast, are not referred to as an aryl or heteroaryl group but as an aromatic or heteroaromatic ring system.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. The heteroaromatic ring system here preferably contains not more than three heteroatoms per heteroaryl group present in the ring system, of which not more than one is selected from O and S and the further heteroatoms are N. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ether, stilbene, etc. shall also be regarded as aromatic ring systems in the context of this invention.

An electron-rich heteroaromatic ring system in the context of the present invention is a heteroaromatic ring system containing no electron-deficient heteroaryl groups. Electron-deficient heteroaryl rings in the context of the present invention are 5-membered heteroaryl rings having two or more heteroatoms and 6-membered heteroaryl rings. An electron-rich heteroaromatic ring system thus contains only aryl rings and 5-membered heteroaryl rings having exactly one heteroatom, especially pyrrole, furan and/or thiophene, where the aryl rings and the 5-membered heteroaryl rings may also be fused to one another. Examples of suitable electron-rich heteroaromatic ring systems are carbazole, dibenzofuran and dibenzothiophene.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An $OR^2$ group is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. An $SR^2$ group is especially understood to mean methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynyithio. In general, alkyl, alkoxy or thioalkyl groups according to the present invention may be straight-chain, branched or cyclic; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-60 aromatic ring atoms and may also be substituted in each case by the abovementioned $R^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from a combination of these systems.

Adjacent radicals or adjacent substituents in the context of the present application are understood to mean substituents which are bonded to carbon atoms that are in turn bonded directly to one another, or substituents bonded to the same carbon atom.

In a preferred embodiment of the invention, the indenocarbazole base skeleton has a total of not more than two R substituents that are not H, more preferably not more than one R substituent that is not H, and most preferably no R substituent that is not H. In a further preferred embodiment of the invention, the phenylene group that joins the indenocarbazole group and the —NAr$^2$Ar$^3$ group to one another is unsubstituted. Very particular preference is thus given to a compound of formula (3)

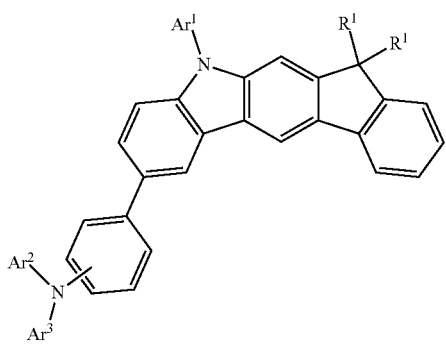

Formula (3)

where the symbols used have the definitions given above.

In a preferred embodiment of the invention, the R$^1$ radicals which bind to the indenocarbazole base skeleton are the same or different at each instance and are selected from the group consisting of a straight-chain alkyl group having 1 to 10 carbon atoms or a branched or cyclic alkyl group having 3 to 10 carbon atoms or an alkenyl group having 2 to 10 carbon atoms, each of which may be substituted by one or more R$^2$ radicals, where one or more nonadjacent CH$_2$ groups may be replaced by O and where one or more hydrogen atoms may be replaced by D or F, or an aromatic or heteroaromatic ring system which has 6 to 24 aromatic ring atoms and may be substituted in each case by one or more R$^2$ radicals, preferably nonaromatic R$^2$ radicals; at the same time, the two R$^1$ substituents may form a monocyclic or polycyclic, aliphatic, aromatic or heteroaromatic ring system which may be substituted by one or more R$^2$ radicals. More preferably, the R$^1$ radicals are the same or different at each instance and are selected from the group consisting of a straight-chain alkyl group having 1 to 4 carbon atoms or a branched or cyclic alkyl group having 3 to 10 carbon atoms, each of which may be substituted by one or more R$^2$ radicals, but is preferably unsubstituted, where one or more hydrogen atoms may be replaced by D or F, or an aromatic ring system which has 6 to 24 aromatic ring atoms and may be substituted by one or more nonaromatic R$^2$ radicals, but is preferably unsubstituted; at the same time, the two R$^1$ substituents may form a monocyclic or polycyclic, aliphatic or aromatic ring system which may be substituted by one or more R$^2$ radicals, but is preferably unsubstituted. Most preferably, the R$^1$ radicals are the same or different at each instance and are selected from methyl, phenyl and two phenyl groups which together form a ring system and hence a spiro system. Preference is thus given to compounds of one of the following formulae (3-1) to (3-4):

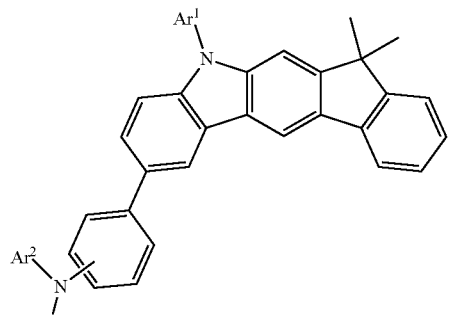

Formula (3-1)

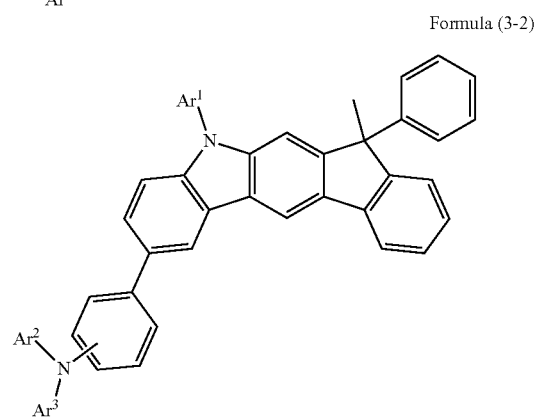

Formula (3-2)

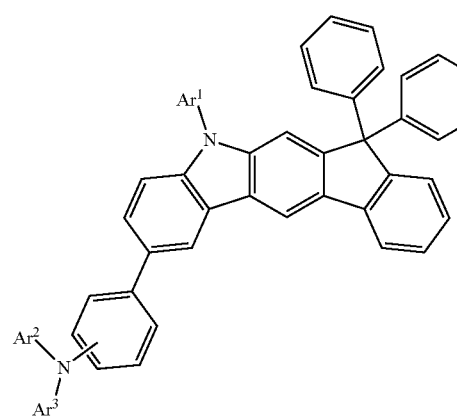

Formula (3-3)

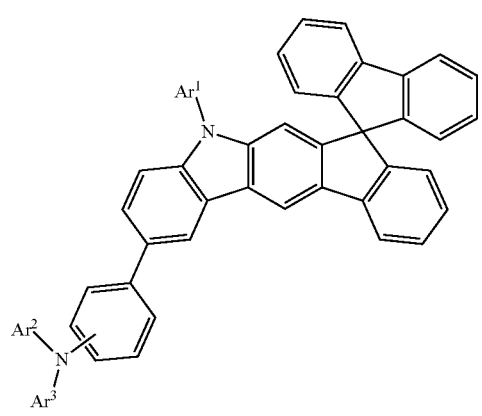

Formula (3-4)

where the symbols used have the definitions given above.

In the compounds of the formula (1), the indenocarbazole group and the —NAr²Ar² group are joined to one another by an optionally substituted, but preferably unsubstituted, phenylene group. In this case, the phenylene group may be joined via the ortho, meta or para positions, preferably via the meta or para positions and more preferably via the para positions. Preferred embodiments of the compound of the formula (1) are thus the compounds of the following formulae (1a) and (1b), particular preference being given to the compound of the formula (1b):

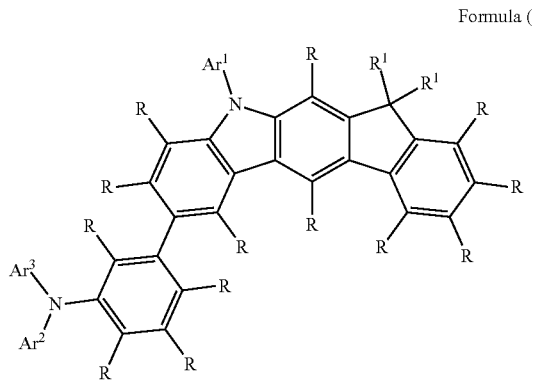

Formula (1a)

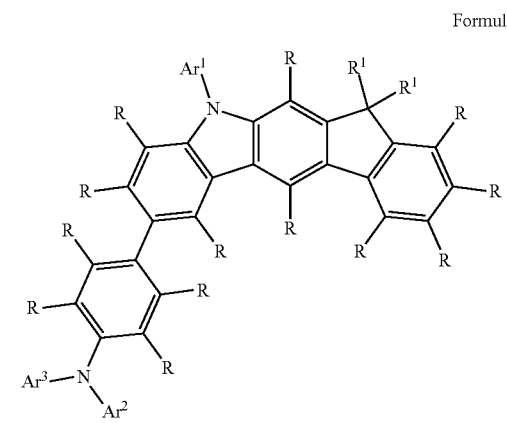

Formula (1b)

where the symbols used have the definitions given above.

Particular preference is given to the compounds of the following formulae (3a) and (3b), very particular preference being given to the compounds of the formula (3b):

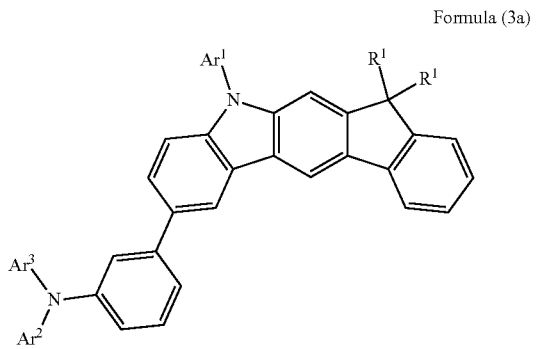

Formula (3a)

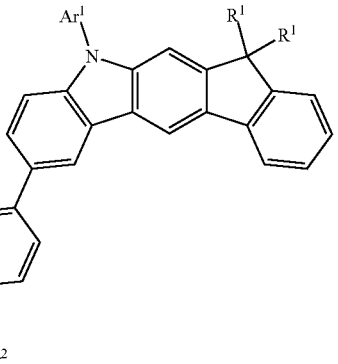

Formula (3b)

where the symbols used have the definitions given above.

There follows a more particular description of the Ar¹ group. In a preferred embodiment of the invention, Ar¹ is an aromatic ring system which has 6 to 24 aromatic ring atoms and may be substituted by one or more R radicals, or an electron-rich heteroaromatic ring system which has 5 to 24 aromatic ring atoms and may be substituted by one or more R radicals, preferably by nonaromatic R radicals. More preferably, Ar¹ is an aromatic ring system which has 6 to 24 aromatic ring atoms and may be substituted by one or more nonaromatic R radicals, but is preferably unsubstituted. Preferred Ar¹ groups are selected from the group consisting of phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorenyl, especially 1-, 2-, 3- or 4-fluorenyl, spirobifluorenyl, especially 1-, 2-, 3- or 4-spirobifluorenyl, dibenzofuranyl, especially 1-, 2-, 3- or 4-dibenzofuranyl, dibenzothienyl, especially 1-, 2-, 3- or 4-dibenzothienyl, or N-phenylcarbazolyl, especially N-phenyl-1-, 2-, 3- or 4-carbazolyl, where these groups may each be substituted by one or more nonaromatic R radicals, but are preferably unsubstituted. Very particular preference is given to phenyl, biphenyl, terphenyl, quaterphenyl and fluorenyl.

Examples of suitable Ar¹ groups are the (Ar¹-1) to (Ar¹-15) groups depicted below:

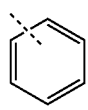

(Ar¹-1)

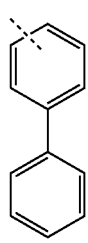

(Ar¹-2)

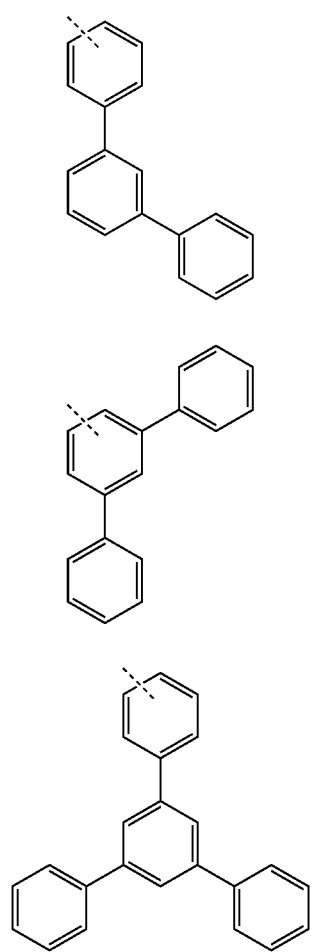
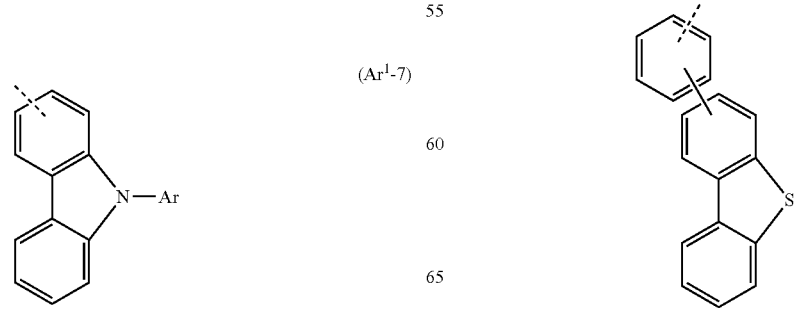

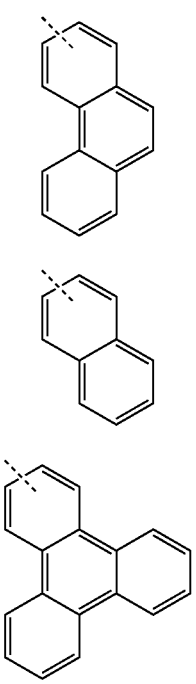

(Ar¹-13)

(Ar¹-14)

(Ar¹-15)

where the dotted bond represents the linkage of this group, the structures may also be substituted by one or more R radicals, preferably nonaromatic R radicals, and the further symbols used have the definitions given above. Preferably, the abovementioned groups are unsubstituted.

Particularly preferred embodiments of the Ar¹ group are the groups of the following formulae (Ar¹-1-a) to (Ar¹-15-b):

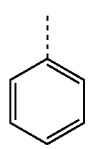

(Ar¹-1-a)

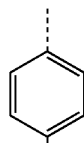

(Ar¹-2-a)

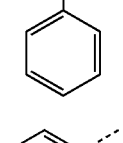

(Ar¹-2-b)

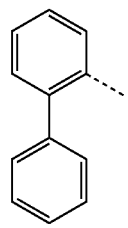

(Ar¹-2-c)

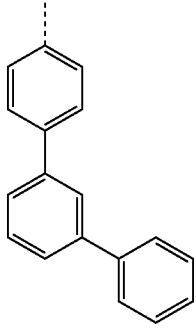

(Ar¹-3-a)

(Ar¹-3-b)

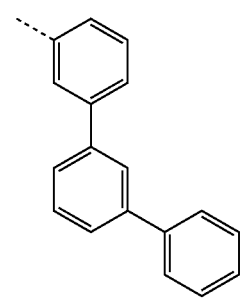

(Ar¹-4-c)

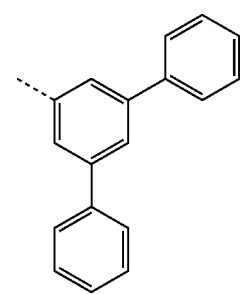

(Ar¹-5-a)

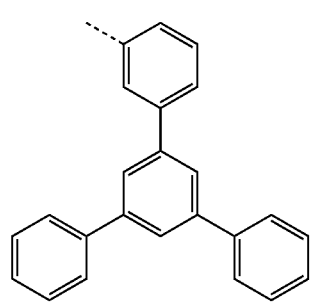

-continued
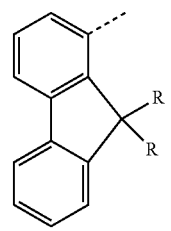 (Ar¹-6-a)
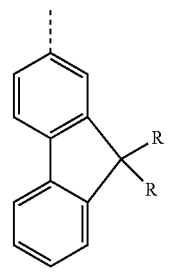 (Ar¹-6-b)
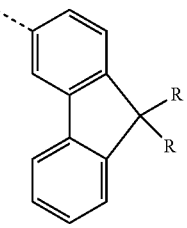 (Ar¹-6-c)
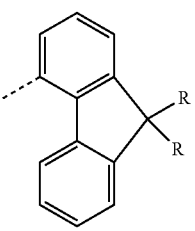 (Ar¹-6-d)
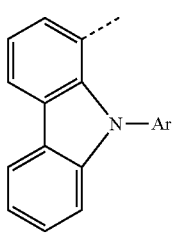 (Ar¹-7-a)
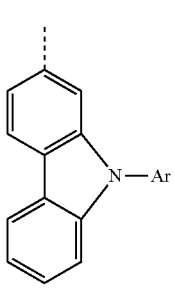 (Ar¹-7-b)
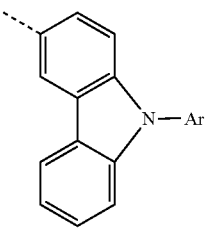 (Ar¹-7-c)
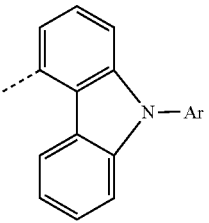 (Ar¹-7-d)
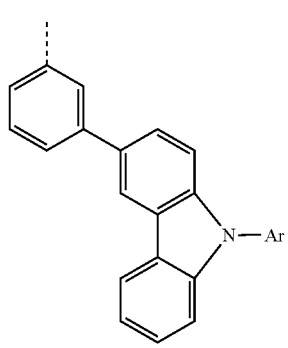 (Ar¹-8-a)
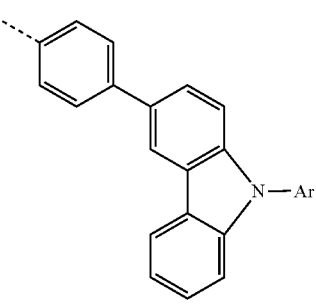 (Ar¹-8-b)
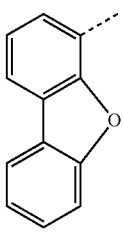 (Ar¹-9-a)
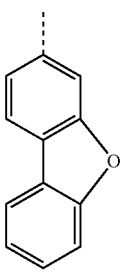 (Ar¹-9-b)

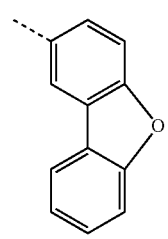 (Ar¹-9-c)
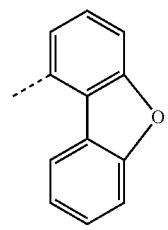 (Ar¹-9-d)
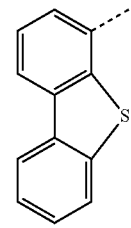 (Ar¹-10-a)
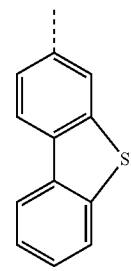 (Ar¹-10-b)
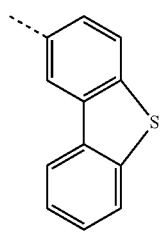 (Ar¹-10-c)
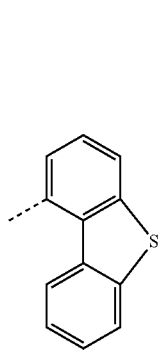 (Ar¹-10-d)
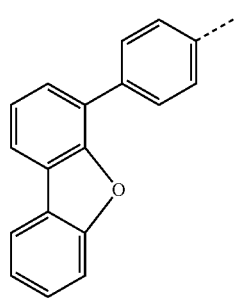 (Ar¹-11a)
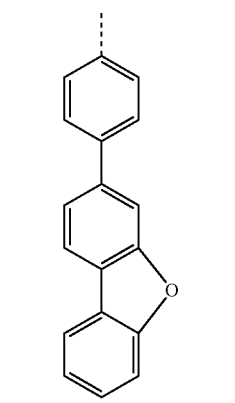 (Ar¹-11b)
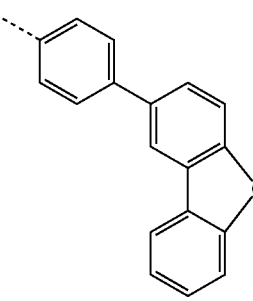 (Ar¹-11c)
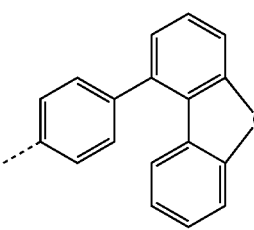 (Ar¹-11d)
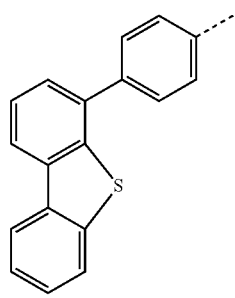 (Ar¹-12a)

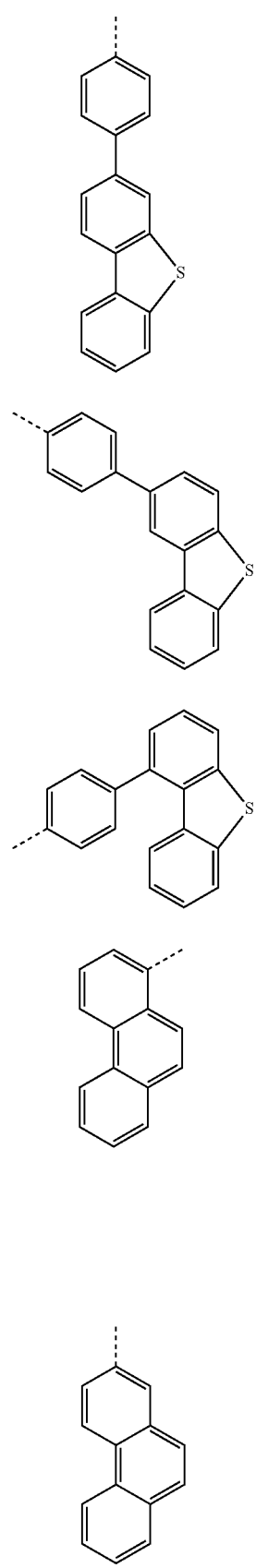
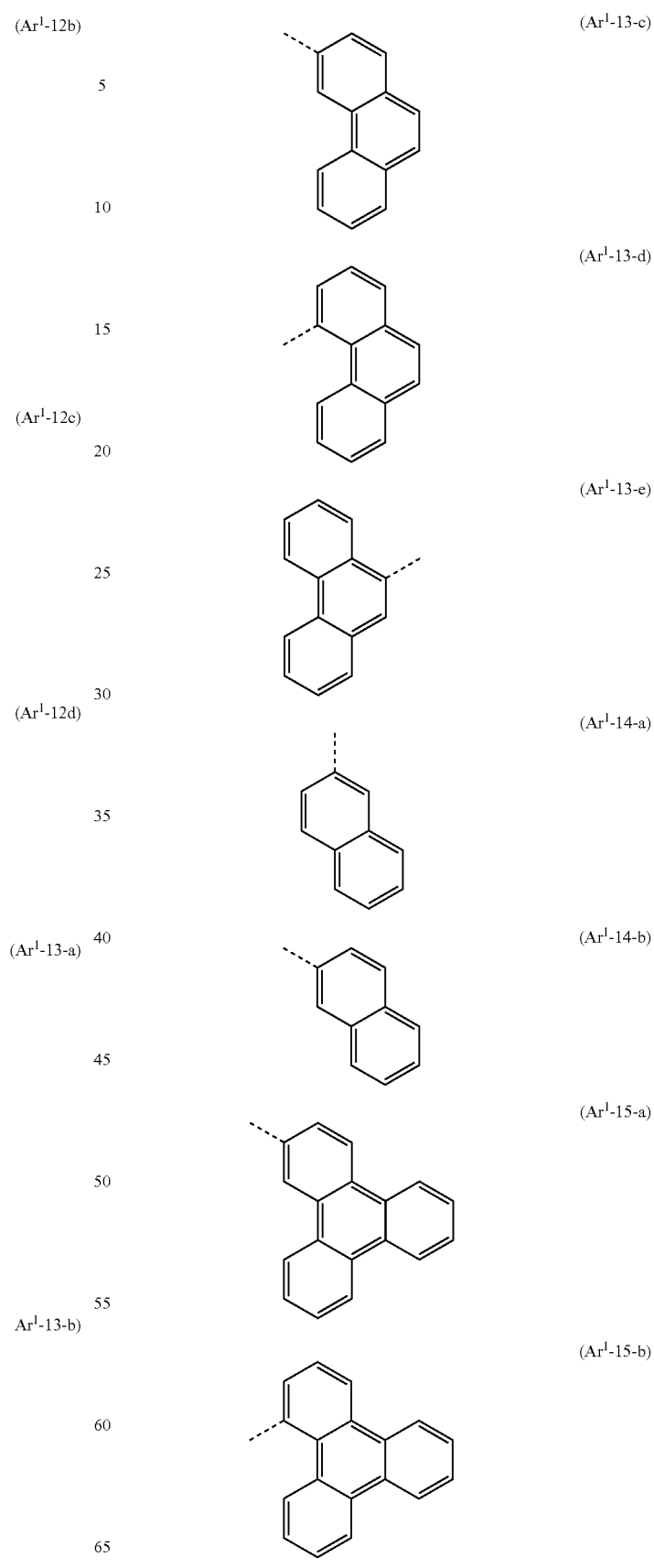

where the symbols used have the definitions given above and the structures may also be substituted by one or more R radicals, but are preferably unsubstituted.

There follows a more particular description of the $Ar^2$ group. In a preferred embodiment of the invention, $Ar^2$ is an aromatic ring system which has 6 to 24 aromatic ring atoms and may be substituted by one or more R radicals, or an electron-rich heteroaromatic ring system which has 5 to 24 aromatic ring atoms and may be substituted by one or more R radicals, preferably by nonaromatic R radicals. More preferably, $Ar^2$ is an aromatic ring system which has 6 to 24 aromatic ring atoms and may be substituted by one or more nonaromatic R radicals, but is preferably unsubstituted. Preferred $Ar^2$ groups are selected from the group consisting of phenyl, biphenyl, especially ortho-, meta- or para-biphenyl, terphenyl, especially ortho-, meta- or para-terphenyl or branched terphenyl, quaterphenyl, especially ortho-, meta- or para-quaterphenyl or branched quaterphenyl, fluorenyl, especially 1-, 2-, 3- or 4-fluorenyl, spirobifluorenyl, especially 1-, 2-, 3- or 4-spirobifluorenyl, dibenzofuranyl, especially 1-, 2-, 3- or 4-dibenzofuranyl, dibenzothienyl, especially 1-, 2-, 3- or 4-dibenzothienyl, or N-phenylcarbazolyl, especially N-phenyl-1-, 2-, 3- or 4-carbazolyl, where these groups may each be substituted by one or more nonaromatic R radicals, but are preferably unsubstituted.

Examples of suitable $Ar^2$ groups are the ($Ar^2$-1) to ($Ar^2$-15) groups depicted below:

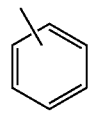

($Ar^2$-1)

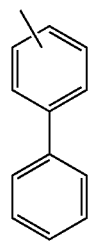

($Ar^2$-2)

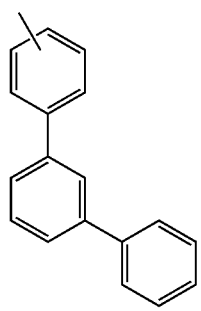

($Ar^2$-3)

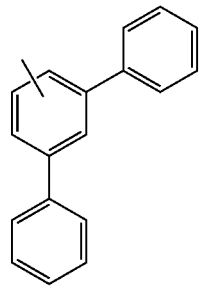

($Ar^2$-4)

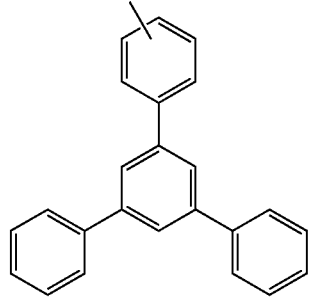

($Ar^2$-5)

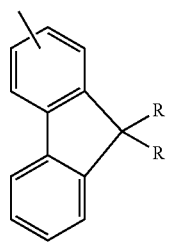

($Ar^2$-6)

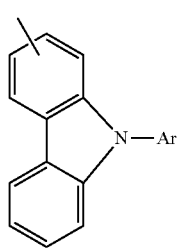

($Ar^2$-7)

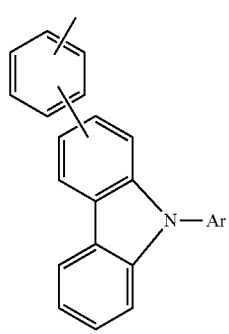

($Ar^2$-8)

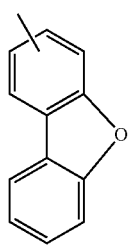
(Ar²-9)

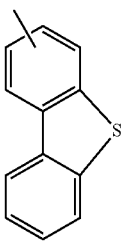
(Ar²-10)

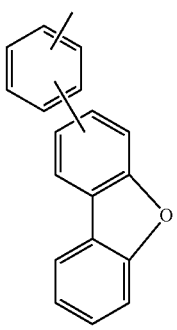
(Ar²-11)

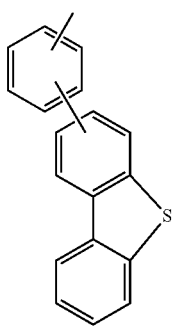
(Ar²-12)

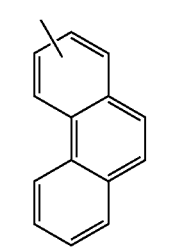
(Ar²-13)

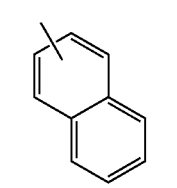
(Ar²-14)

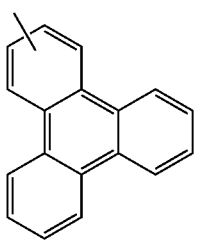
(Ar²-15)

where the dotted bond represents the linkage of this group, the structures may also be substituted by one or more R radicals, preferably nonaromatic R radicals, and the further symbols used have the definitions given above.

Particularly preferred embodiments of the Ar² group are the groups of the following formulae (Ar²-1a) to (Ar²-15b):

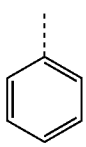
(Ar²-1a)

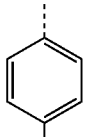
(Ar²-2a)

(Ar²-2b)

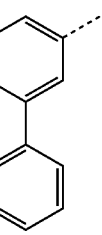
(Ar²-2c)

-continued
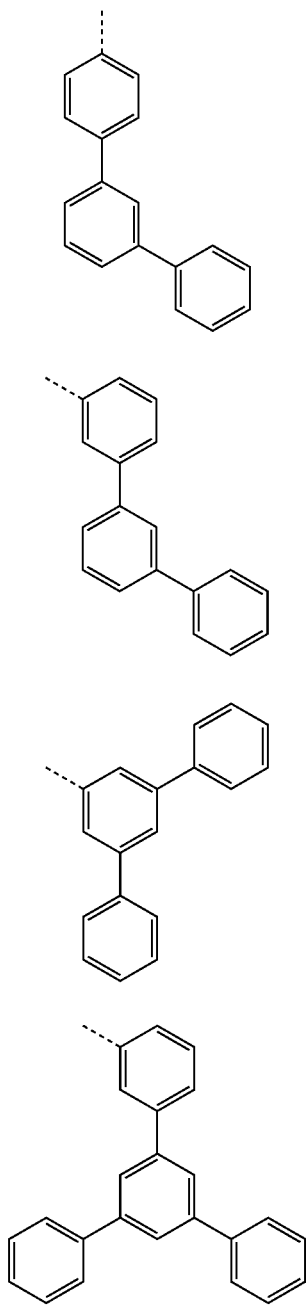
(Ar²-3a)
(Ar²-3b)
(Ar²-4c)
(Ar²-5a)
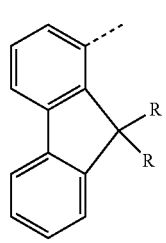
(Ar²-6a)
-continued
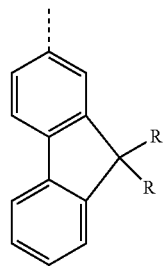
(Ar²-6b)
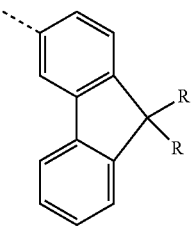
(Ar²-6c)
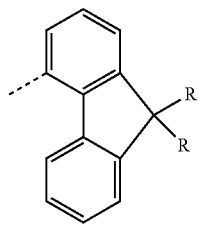
(Ar²-6d)
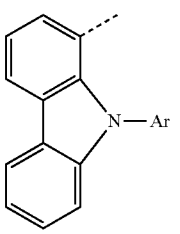
(Ar²-7a)
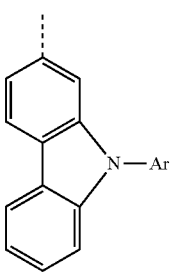
(Ar²-7b)
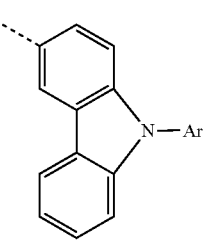
(Ar²-7c)

(Ar²-7d)
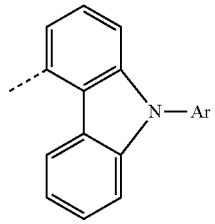
(Ar²-8a)
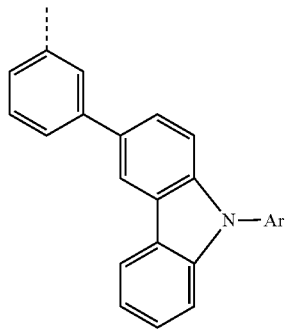
(Ar²-8b)
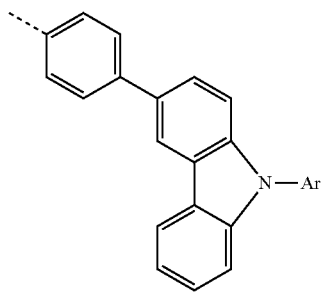
(Ar²-9a)
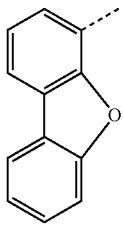
(Ar²-9b)
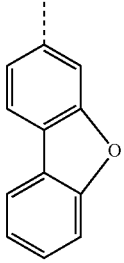
(Ar²-9c)
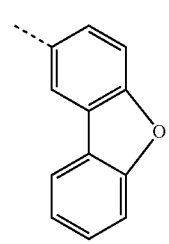
(Ar²-9d)
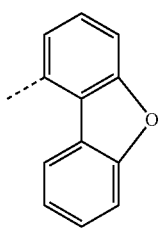
(Ar²-10a)
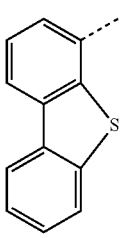
(Ar²-10b)
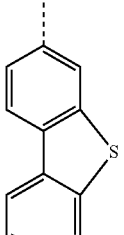
(Ar²-10c)
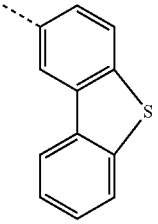
(Ar²-10d)
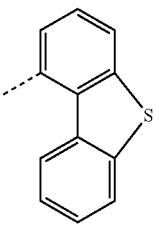
(Ar²-11a)
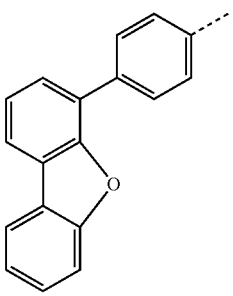

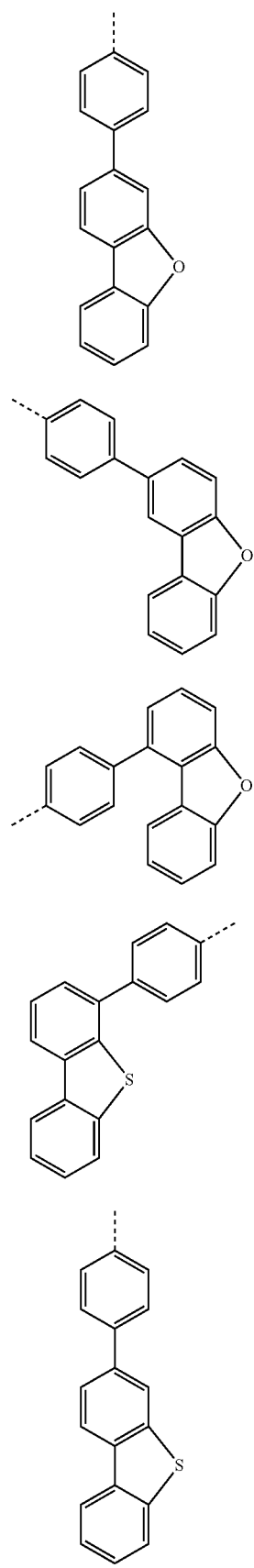
(Ar²-11b)
(Ar²-11c)
(Ar²-11d)
(Ar²-12a)
(Ar²-12b)
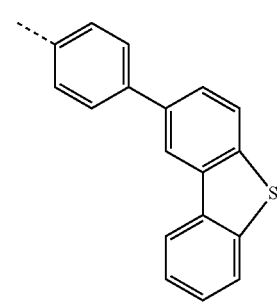
(Ar²-12c)
(Ar²-12d)
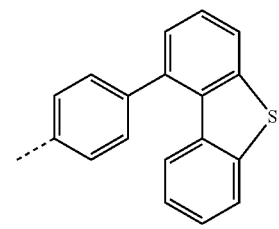
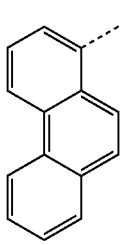
(Ar²-13-a)
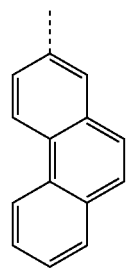
Ar²-13b)
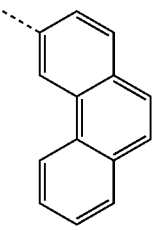
(Ar²-13c)
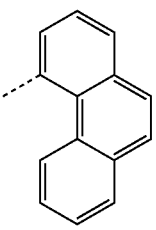
(Ar²-13d)

(Ar²-13e)
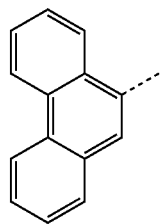

(Ar²-14a)
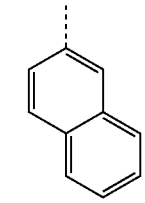

(Ar²-14b)
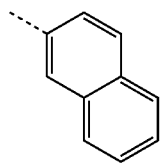

(Ar²-15a)
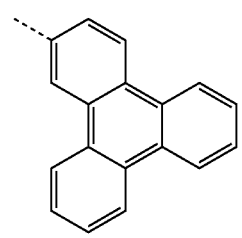

(Ar²-15b)
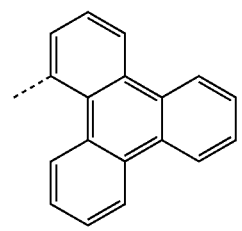

where the symbols used have the definitions given above and the structures may also be substituted by one or more R radicals, but are preferably unsubstituted.

There follows a more particular description of the Ar³ group, i.e. the group of the formula (2). In a preferred embodiment of the invention, p=0. In a further preferred embodiment of the invention, p=1 and the phenylene group is an unsubstituted meta- or para-bonded phenylene group, especially a para-bonded phenylene group. Preferred embodiments of the group of the formula (2) are thus the groups of the formulae (2a) to (2c)

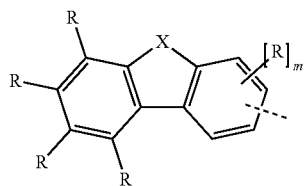
Formula (2a)

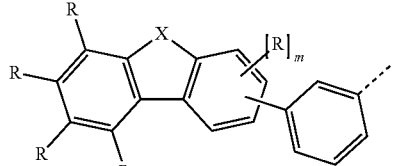
Formula (2b)

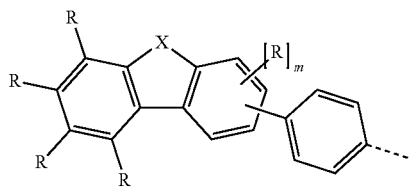
Formula (2c)

where the symbols and indices used have the definitions given above and the fluorene group or dibenzofuran group or dibenzothiophene group is bonded in accordance with the invention via the 1, 3 or 4 position. Particular preference is given to a group of the formula (2a).

Embodiments of the group (2a) are the groups of the following formulae (2a-1) to (2a-9):

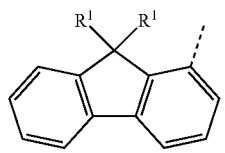
Formula (2a-1)

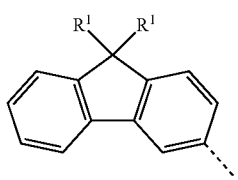
Formula (2a-2)

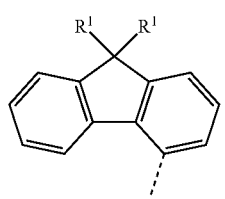
Formula (2a-3)

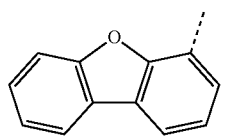
Formula (2a-4)

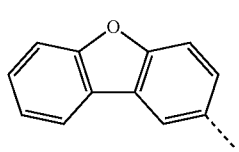

Formula (2a-5)

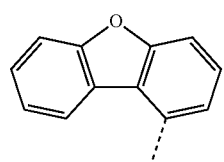

Formula (2a-6)

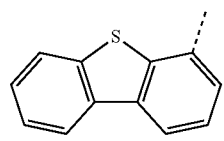

Formula (2a-7)

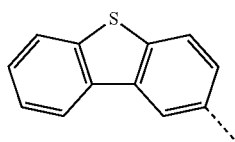

Formula (2a-8)

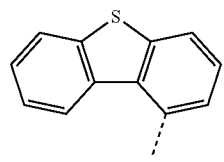

Formula (2a-9)

where the dotted bond represents the linkage of this group to the nitrogen atom and the further symbols used have the definitions given above.

Analogously, groups of the formulae (2b) and (2c) are possible, where these differ from the structures of the formulae (2a-1) to (2a-9) merely in that another meta- or para-phenylene group is present between the fluorene group or dibenzofuran group or dibenzothiophene group and the nitrogen atom of the amine.

Preferably, in the group of the formula (2) or the preferred embodiments, X is $C(R^1)_2$ or O, more preferably $C(R^1)_2$.

When X is $C(R^1)_2$, the $Ar^3$ group is preferably a group of the abovementioned formula (2a-1) or (2a-3), more preferably a group of the abovementioned formula (2a-3). When X is O, the $Ar^3$ group is preferably a group of the abovementioned formula (2a-4) or (2a-6). When X is S, the $Ar^3$ group is preferably a group of the abovementioned formula (2a-7) or (2a-9).

In a preferred embodiment of the invention, the $R^1$ radicals which, when $X = C(R^1)_2$, bind to the fluorene of the formula (2) or the preferred embodiments are the same or different at each instance and are selected from the group consisting of a straight-chain alkyl group having 1 to 10 carbon atoms or a branched or cyclic alkyl group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, or an aromatic or heteroaromatic ring system which has 6 to 24 aromatic ring atoms and may be substituted in each case by one or more $R^2$ radicals, preferably nonaromatic $R^2$ radicals; at the same time, the two $R^1$ substituents may form a monocyclic or polycyclic, aliphatic, aromatic or heteroaromatic ring system which may be substituted by one or more $R^2$ radicals. More preferably, the $R^1$ radicals are the same or different at each instance and are selected from the group consisting of a straight-chain alkyl group having 1 to 4 carbon atoms or a branched or cyclic alkyl group having 3 to 10 carbon atoms, each of which may be substituted by one or more $R^2$ radicals, but is preferably unsubstituted, where one or more hydrogen atoms may be replaced by D or F, or an aromatic ring system which has 6 to 24 aromatic ring atoms and may be substituted by one or more nonaromatic $R^2$ radicals, but is preferably unsubstituted; at the same time, the two $R^1$ substituents may form a monocyclic or polycyclic, aliphatic or aromatic ring system which may be substituted by one or more $R^2$ radicals, but is preferably unsubstituted. Most preferably, the $R^1$ radicals are the same or different at each instance and are selected from methyl, phenyl and two phenyl groups which together form a ring system and hence a spiro system. Especially preferably, either both $R^1$ radicals are methyl or both $R^1$ radicals are phenyl groups which together form a ring system and hence a spirobifluorene.

In a further preferred embodiment of the invention, R is the same or different at each instance and is selected from the group consisting of H, D, F, CN, $N(R^2)_2$, $OR^2$, a straight-chain alkyl group having 1 to 10 carbon atoms or a branched or cyclic alkyl group having 3 to 10 carbon atoms or an alkenyl group having 2 to 10 carbon atoms, each of which may be substituted by one or more $R^2$ radicals, where one or more nonadjacent $CH_2$ groups may be replaced by O and where one or more hydrogen atoms may be replaced by D or F, or an aromatic or heteroaromatic ring system which has 5 to 30 aromatic ring atoms and may be substituted in each case by one or more $R^2$ radicals. More preferably, R is the same or different at each instance and is selected from the group consisting of H, $N(R^2)_2$, a straight-chain alkyl group having 1 to 6 carbon atoms, especially having 1 to 4 carbon atoms, or a branched or cyclic alkyl group having 3 to 8 carbon atoms, especially having 3 to 6 carbon atoms, each of which may be substituted by one or more $R^2$ radicals, but is preferably unsubstituted, or an aromatic or heteroaromatic ring system which has 5 to 24 aromatic ring atoms and may be substituted in each case by one or more $R^2$ radicals, but is preferably unsubstituted.

When R is an aromatic or heteroaromatic ring system, this R radical is preferably the same or different at each instance and is selected from the same groups as specified above as suitable groups for $Ar^1$ and $Ar^2$.

At the same time, in compounds which are processed by vacuum evaporation, the alkyl groups preferably have not more than five carbon atoms, more preferably not more than 4 carbon atoms, most preferably not more than 1 carbon atom. For compounds which are processed from solution, suitable compounds are also those substituted by alkyl groups, especially branched alkyl groups, having up to 10 carbon atoms or those substituted by oligoarylene groups, for example ortho-, meta-, para- or branched terphenyl or quaterphenyl groups.

When the compound of the formula (1) or the preferred embodiments is/are used as matrix material for a phosphorescent emitter or in a layer directly adjoining a phosphorescent layer, it is further preferable when the triplet energy of the compound is equally high or higher than that of the phosphorescent emitter. This may especially be achieved for green- and blue-phosphorescing emitters having a higher triplet energy than red-phosphorescing emitters by virtue of the compound of the invention containing no fused aryl or heteroaryl groups in which more than two six-membered rings are fused directly to one another. Such compounds are therefore a further preferred embodiment of the invention. It is especially preferable for this use that the R, $R^1$, $R^2$, $Ar^1$ and $Ar^2$ radicals do not contain any fused aryl or heteroaryl groups in which two or more six-membered rings are fused directly to one another. Optionally, these groups may also contain phenanthrene or triphenylene, since these aryl groups, in spite of the three or four fused six-membered rings, have a sufficiently high triplet energy.

The abovementioned preferred embodiments may be combined with one another as desired. In a particularly preferred embodiment of the invention, the abovementioned preferences occur simultaneously.

Examples of suitable compounds according to the above-detailed embodiments are the compounds detailed in the following table:

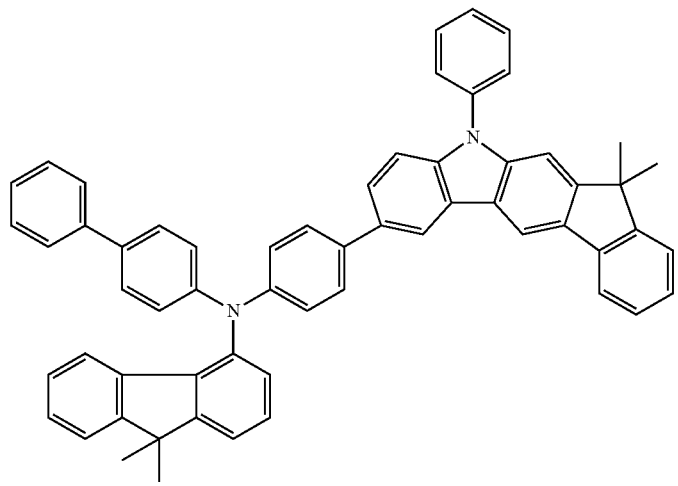 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccccc4)c3cc21]

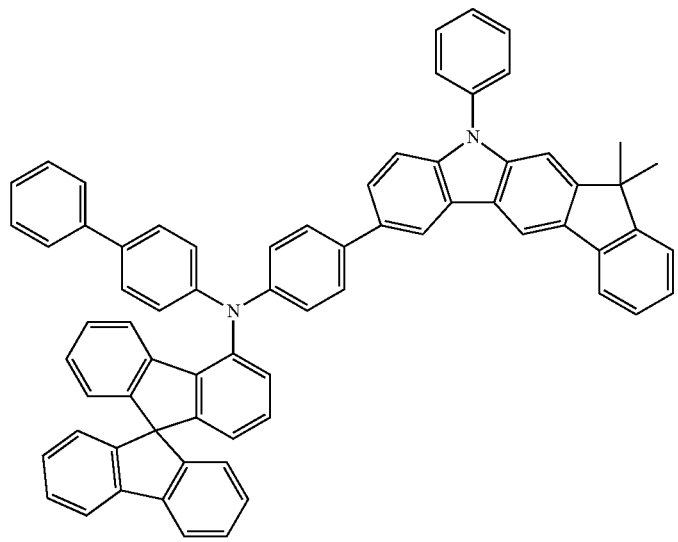 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccccc4)c3cc21]

-continued
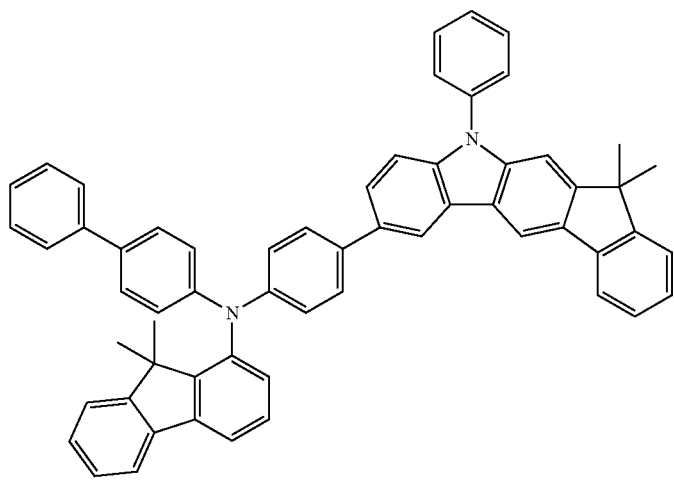 [SMILES: CC1(C)c2ccccc2-c2cc3c4cc(-c5ccc(N(c6ccc(-c7ccccc7)cc6)c6cccc7c6C(C)(C)c6ccccc6-7)cc5)ccc4n(-c4ccccc4)c3cc21]
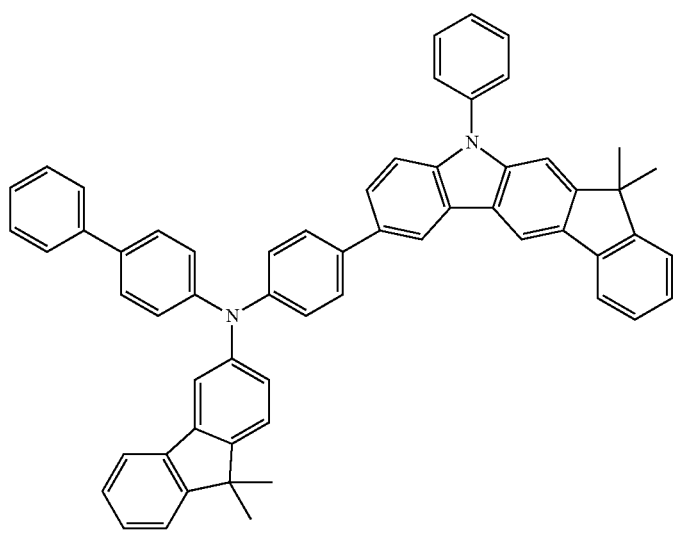 [SMILES: CC1(C)c2ccccc2-c2cc(N(c3ccc(-c4ccccc4)cc3)c3ccc(-c4ccc5c(c4)c4cc6c(cc4n5-c4ccccc4)C(C)(C)c4ccccc4-6)cc3)ccc21]
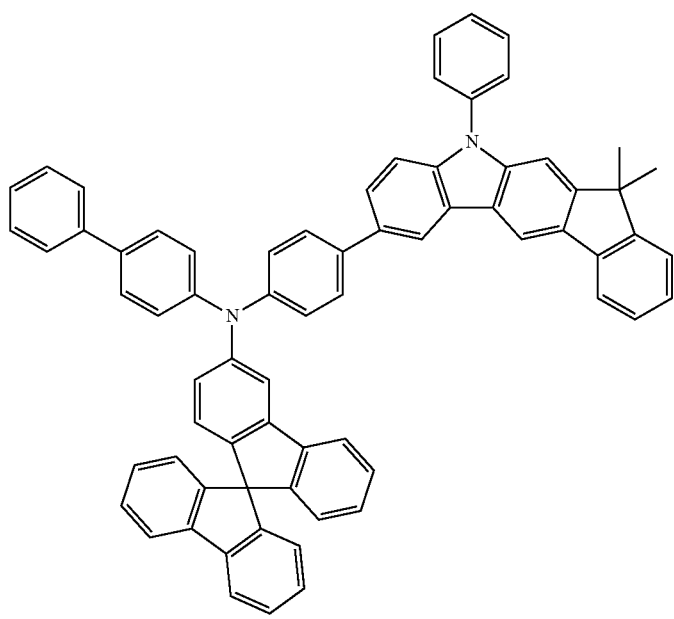 [SMILES: CC1(C)c2ccccc2-c2cc3c4cc(-c5ccc(N(c6ccc(-c7ccccc7)cc6)c6ccc7c(c6)-c6ccccc6C76c7ccccc7-c7ccccc76)cc5)ccc4n(-c4ccccc4)c3cc21]

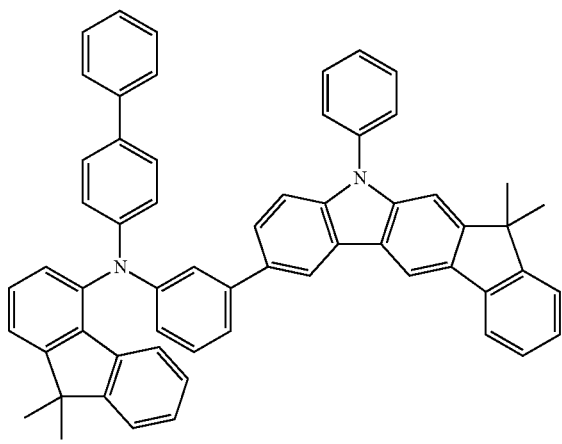 [SMILES: CC1(C)c2ccccc2-c2cc3c4cc(-c5cccc(N(c6ccc(-c7ccccc7)cc6)c6cccc7c6-c6ccccc6C7(C)C)c5)ccc4n(-c4ccccc4)c3cc21]
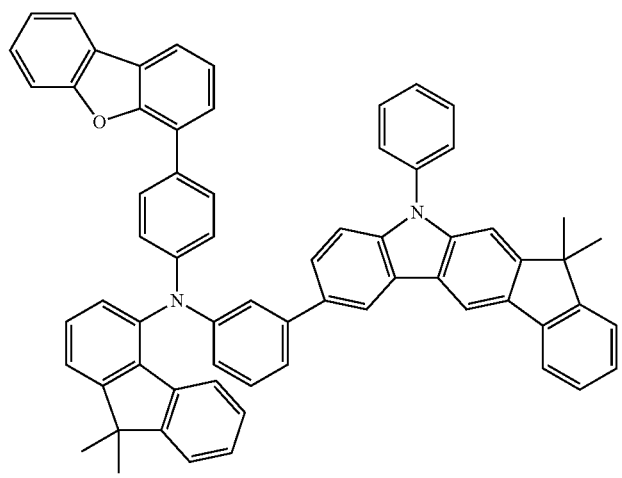 [SMILES: CC1(C)c2ccccc2-c2cc3c4cc(-c5cccc(N(c6ccc(-c7cccc8c7oc7ccccc78)cc6)c6cccc7c6-c6ccccc6C7(C)C)c5)ccc4n(-c4ccccc4)c3cc21]
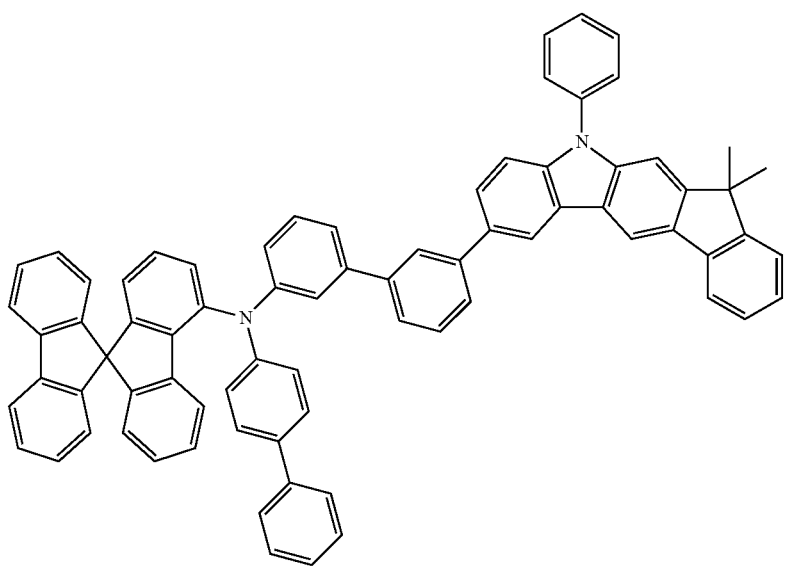 [SMILES: CC1(C)c2ccccc2-c2cc3c4cc(-c5cccc(-c6cccc(N(c7ccc(-c8ccccc8)cc7)c7cccc8c7-c7ccccc7C87c8ccccc8-c8ccccc87)c6)c5)ccc4n(-c4ccccc4)c3cc21]

-continued
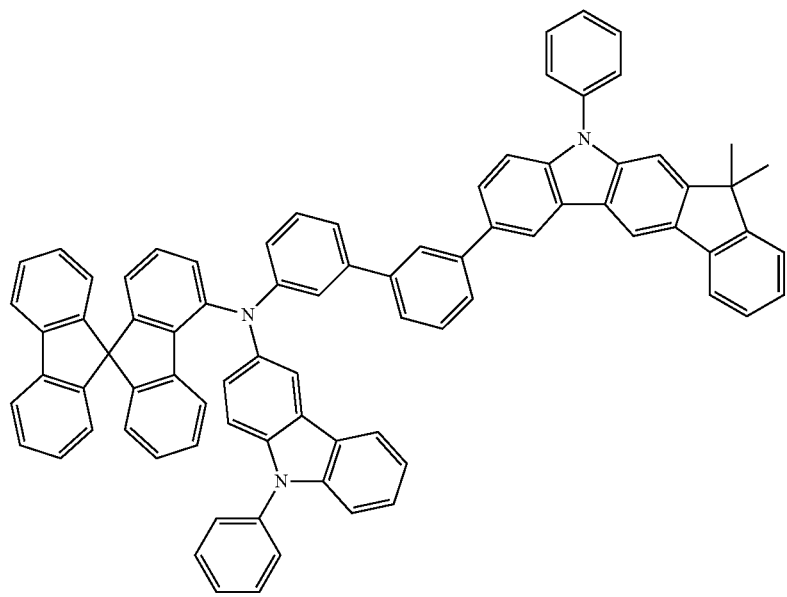 [SMILES: CC1(C)c2ccccc2-c2cc3c4cc(-c5cccc(-c6cccc(N(c7ccc8c(c7)c7ccccc7n8-c7ccccc7)c7cccc8c7-c7ccccc7C87c8ccccc8-c8ccccc87)c6)c5)ccc4n(-c4ccccc4)c3cc21]
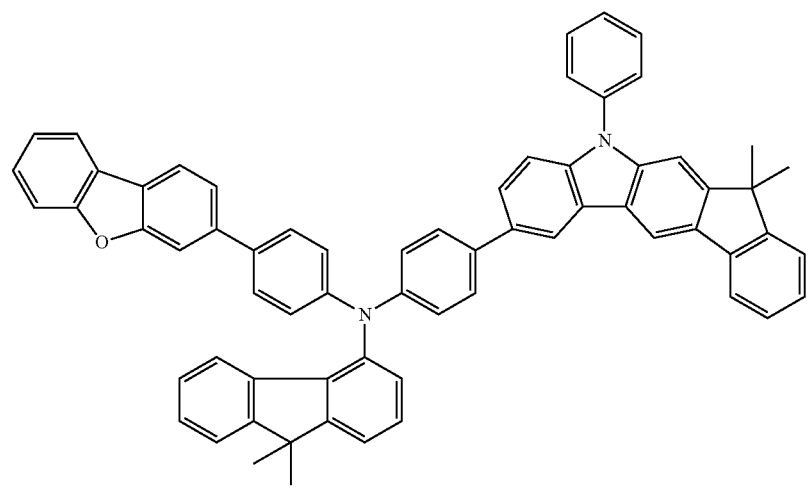 [SMILES: CC1(C)c2ccccc2-c2cc3c4cc(-c5ccc(N(c6ccc(-c7ccc8c(c7)oc7ccccc78)cc6)c6cccc7c6-c6ccccc6C7(C)C)cc5)ccc4n(-c4ccccc4)c3cc21]
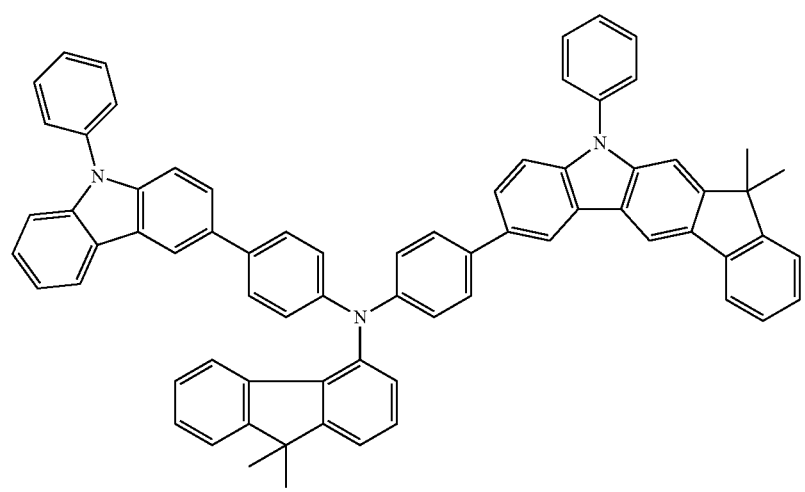 [SMILES: CC1(C)c2ccccc2-c2cc3c4cc(-c5ccc(N(c6ccc(-c7ccc8c(c7)c7ccccc7n8-c7ccccc7)cc6)c6cccc7c6-c6ccccc6C7(C)C)cc5)ccc4n(-c4ccccc4)c3cc21]

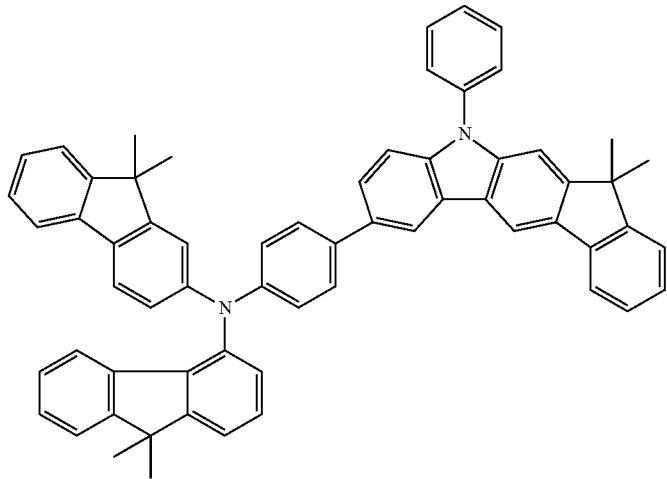 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C4(C)C)cc21]
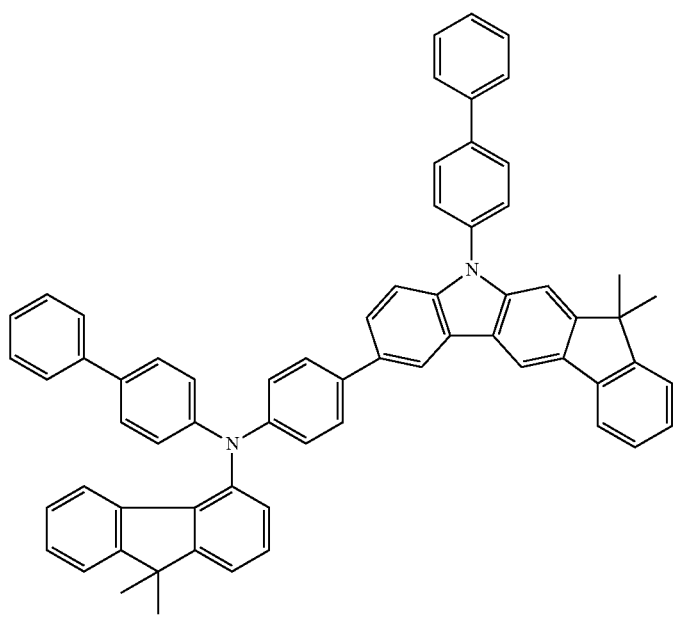 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccc(-c5ccccc5)cc4)c3cc21]

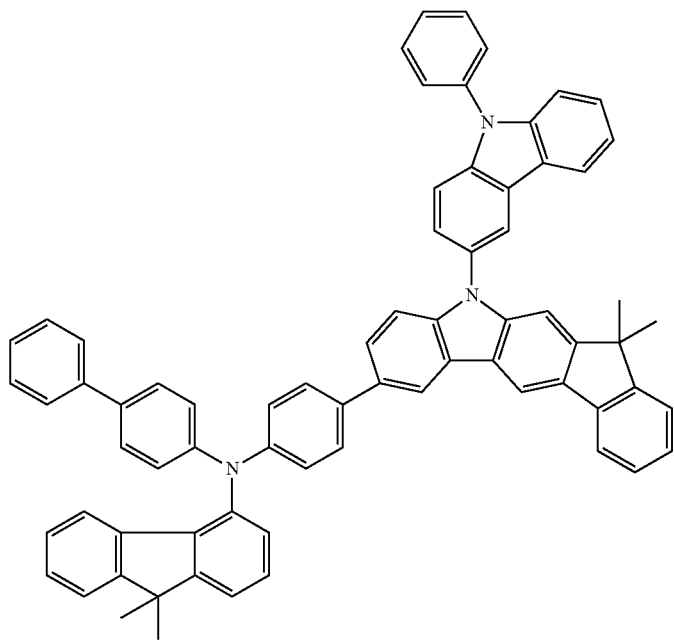 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccc5c(c4)c4ccccc4n5-c4ccccc4)c3cc21]
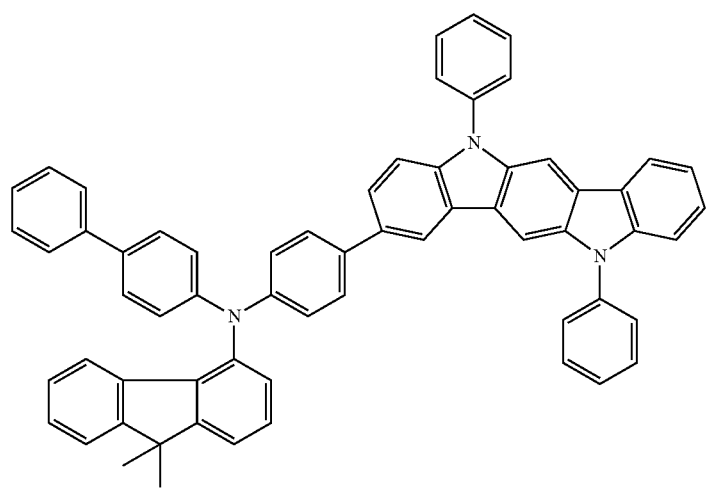 [SMILES: CC1(C)c2ccccc2-c2c(N(c3ccc(-c4ccccc4)cc3)c3ccc(-c4ccc5c(c4)c4cc6c(cc4n5-c4ccccc4)c4ccccc4n6-c4ccccc4)cc3)cccc21]

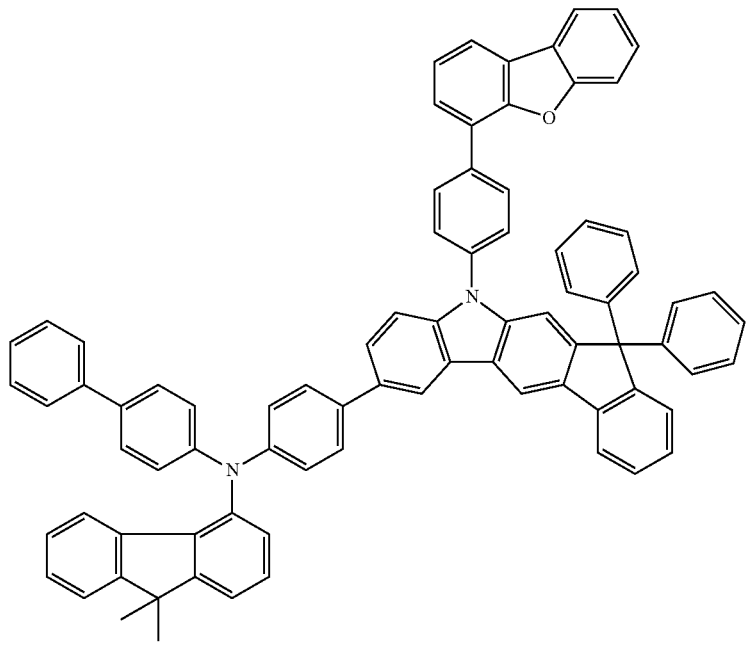 [SMILES: CC1(C)c2ccccc2-c2c(N(c3ccc(-c4ccccc4)cc3)c3ccc(-c4ccc5c(c4)c4cc6c(cc4n5-c4ccc(-c5cccc7c5oc5ccccc57)cc4)C(c4ccccc4)(c4ccccc4)c4ccccc4-6)cc3)cccc21]
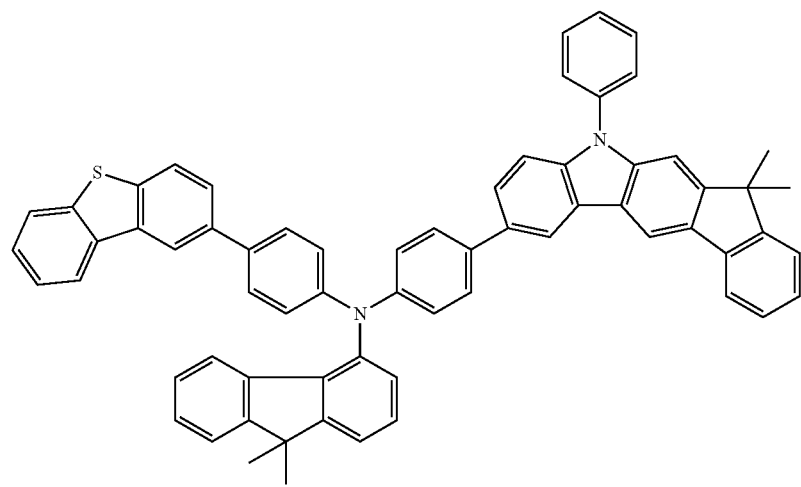 [SMILES: CC1(C)c2ccccc2-c2cc3c4cc(-c5ccc(N(c6ccc(-c7ccc8sc9ccccc9c8c7)cc6)c6cccc7c6-c6ccccc6C7(C)C)cc5)ccc4n(-c4ccccc4)c3cc21]
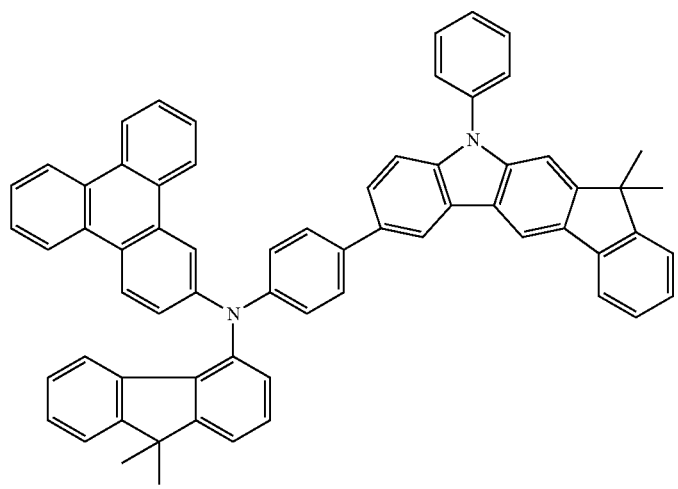 [SMILES: CC1(C)c2ccccc2-c2cc3c4cc(-c5ccc(N(c6ccc7c8ccccc8c8ccccc8c7c6)c6cccc7c6-c6ccccc6C7(C)C)cc5)ccc4n(-c4ccccc4)c3cc21]

-continued
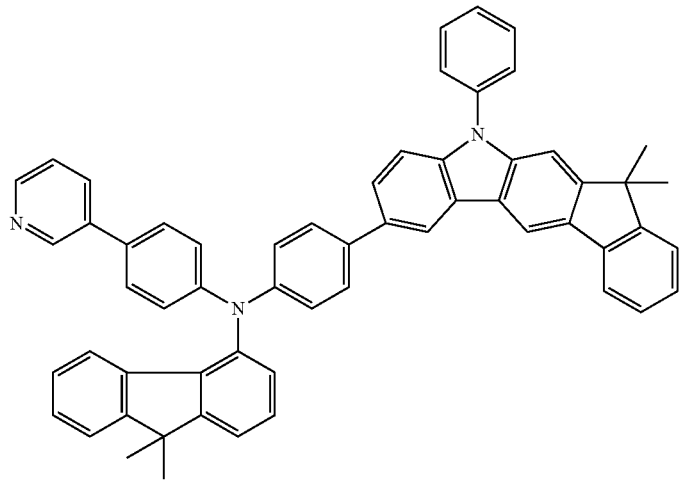 [SMILES: CC1(C)c2ccccc2-c2cc3c4cc(-c5ccc(N(c6ccc(-c7cccnc7)cc6)c6cccc7c6-c6ccccc6C7(C)C)cc5)ccc4n(-c4ccccc4)c3cc21]
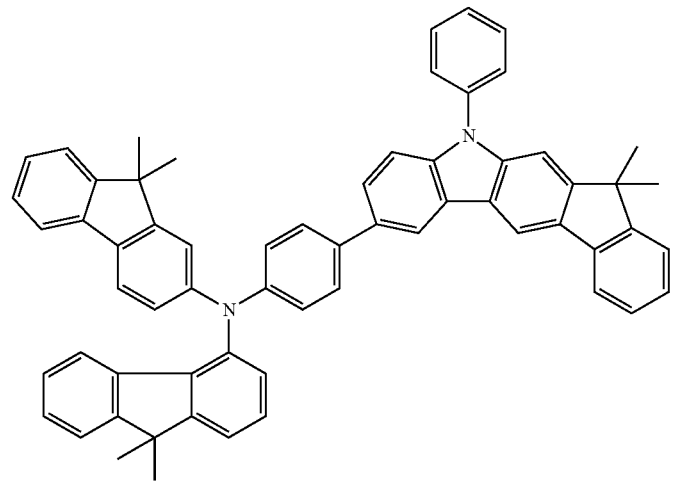 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C4(C)C)cc21]
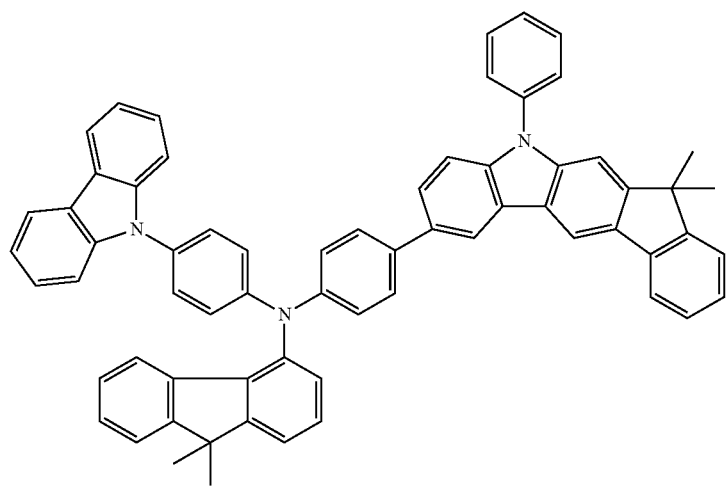 [SMILES: CC1(C)c2ccccc2-c2cc3c4cc(-c5ccc(N(c6ccc(-n7c8ccccc8c8ccccc87)cc6)c6cccc7c6-c6ccccc6C7(C)C)cc5)ccc4n(-c4ccccc4)c3cc21]

-continued
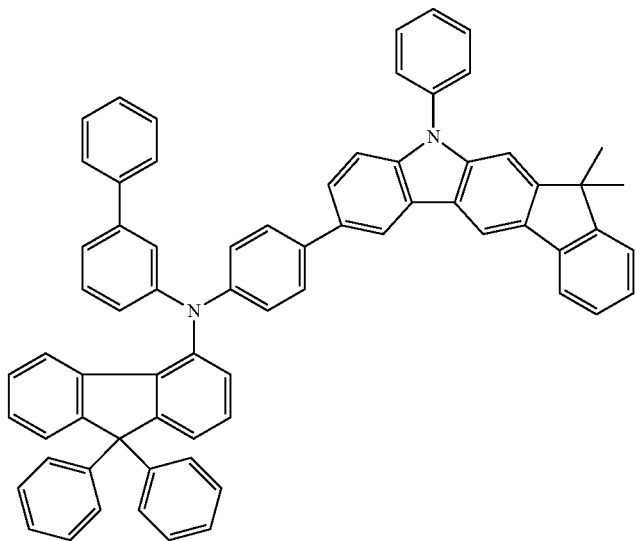 [SMILES: CC1(C)c2ccccc2-c2cc3c4cc(-c5ccc(N(c6cccc(-c7ccccc7)c6)c6cccc7c6-c6ccccc6C7(c6ccccc6)c6ccccc6)cc5)ccc4n(-c4ccccc4)c3cc21]
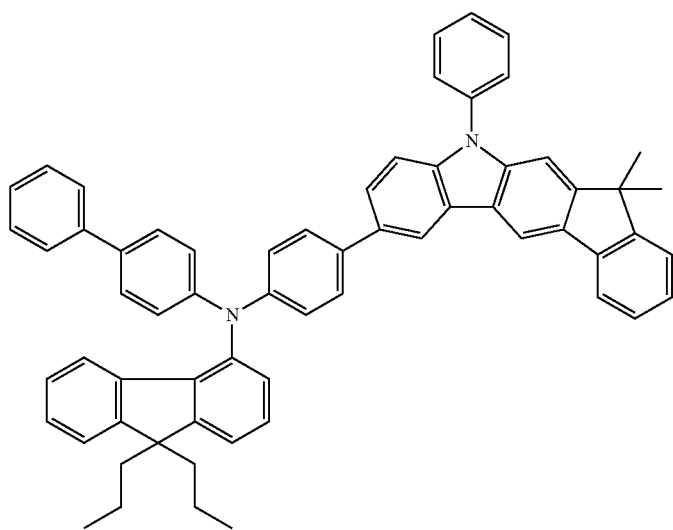 [SMILES: CCCC1(CCC)c2ccccc2-c2c(N(c3ccc(-c4ccccc4)cc3)c3ccc(-c4ccc5c(c4)c4cc6c(cc4n5-c4ccccc4)C(C)(C)c4ccccc4-6)cc3)cccc21]
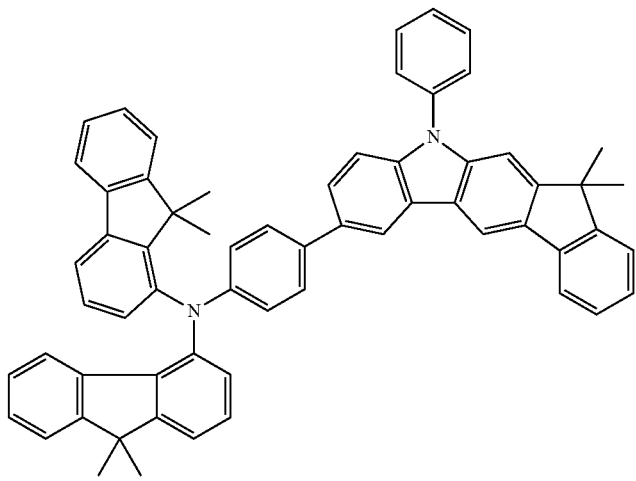 [SMILES: CC1(C)c2ccccc2-c2cc3c4cc(-c5ccc(N(c6cccc7c6-c6ccccc6C7(C)C)c6cccc7c6C(C)(C)c6ccccc6-7)cc5)ccc4n(-c4ccccc4)c3cc21]

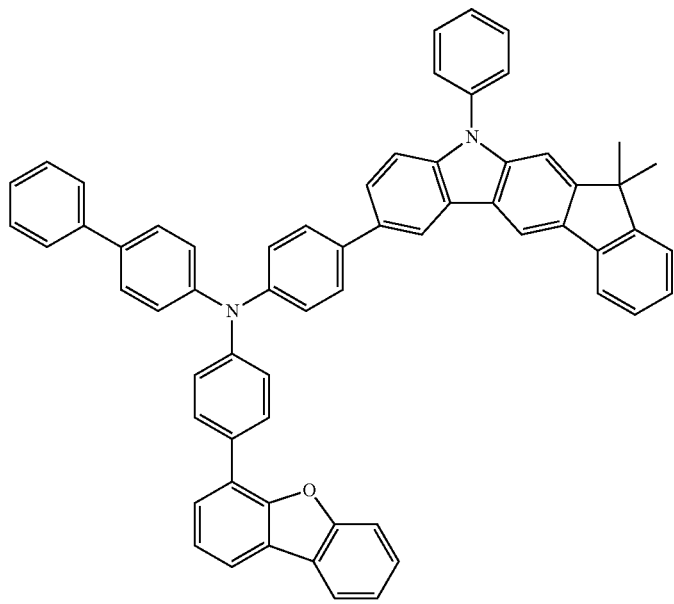 [SMILES: CC1(C)c2ccccc2-c2cc3c4cc(-c5ccc(N(c6ccc(-c7ccccc7)cc6)c6ccc(-c7cccc8c7oc7ccccc78)cc6)cc5)ccc4n(-c4ccccc4)c3cc21]
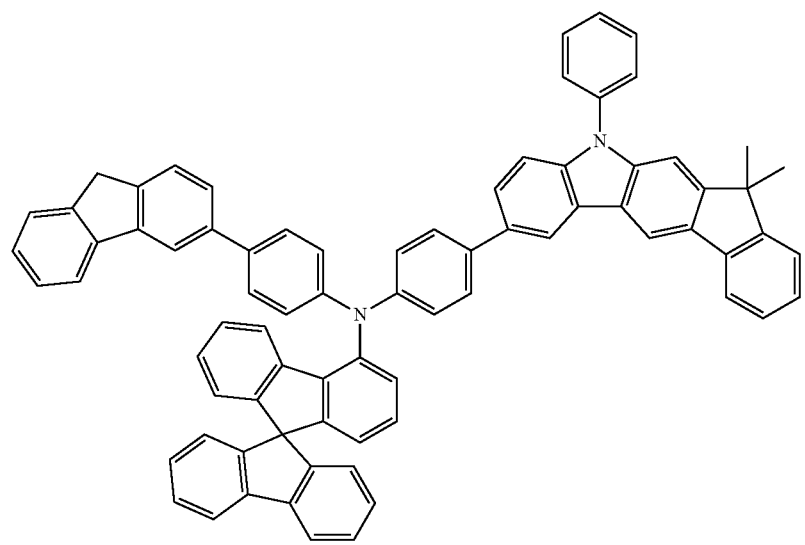 [SMILES: CC1(C)c2ccccc2-c2cc3c4cc(-c5ccc(N(c6ccc(-c7ccc8c(c7)-c7ccccc7C8)cc6)c6cccc7c6-c6ccccc6C76c7ccccc7-c7ccccc76)cc5)ccc4n(-c4ccccc4)c3cc21]

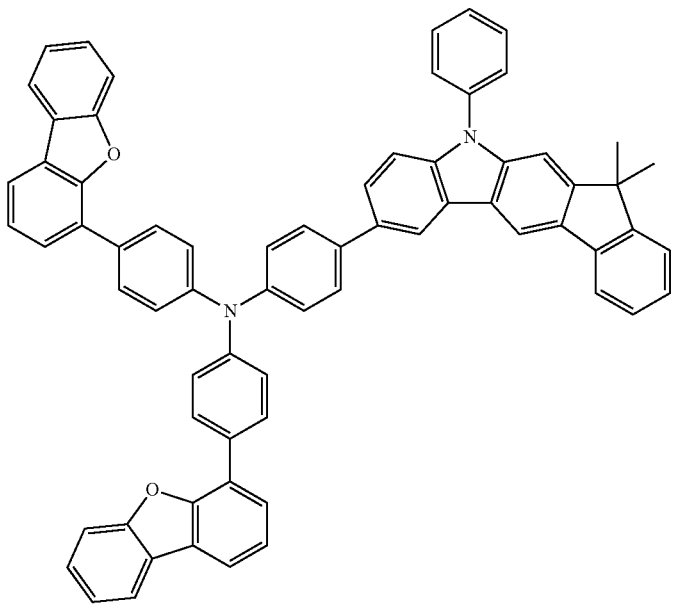 [SMILES: CC1(C)c2ccccc2-c2cc3c4cc(-c5ccc(N(c6ccc(-c7cccc8c7oc7ccccc78)cc6)c6ccc(-c7cccc8c7oc7ccccc78)cc6)cc5)ccc4n(-c4ccccc4)c3cc21]
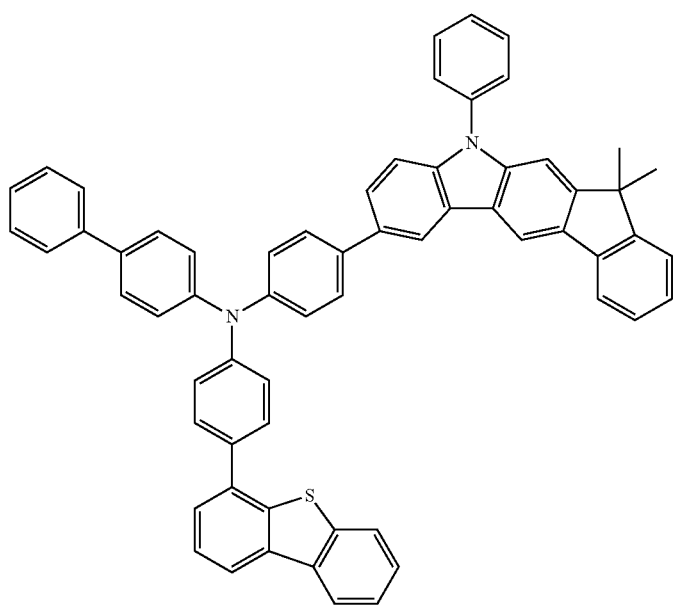 [SMILES: CC1(C)c2ccccc2-c2cc3c4cc(-c5ccc(N(c6ccc(-c7ccccc7)cc6)c6ccc(-c7cccc8c7sc7ccccc78)cc6)cc5)ccc4n(-c4ccccc4)c3cc21]

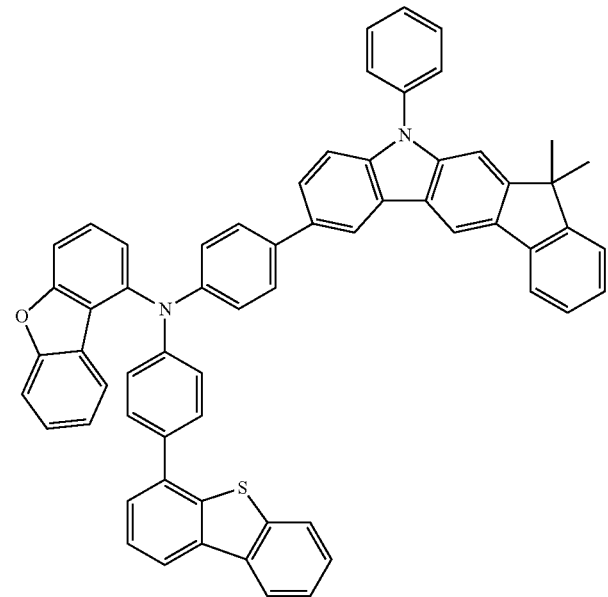 [SMILES: CC1(C)c2ccccc2-c2cc3c4cc(-c5ccc(N(c6ccc(-c7cccc8c7sc7ccccc78)cc6)c6cccc7oc8ccccc8c67)cc5)ccc4n(-c4ccccc4)c3cc21]
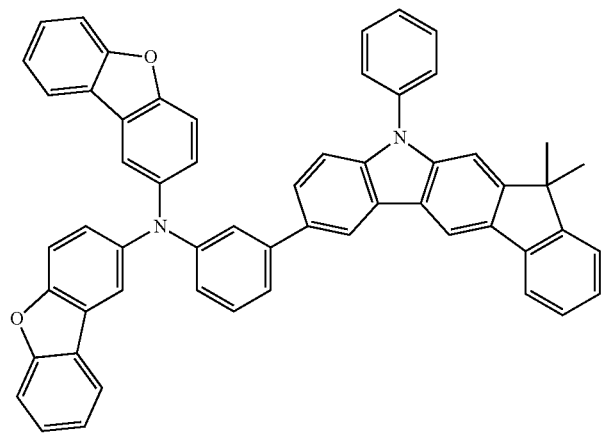 [SMILES: CC1(C)c2ccccc2-c2cc3c4cc(-c5cccc(N(c6ccc7oc8ccccc8c7c6)c6ccc7oc8ccccc8c7c6)c5)ccc4n(-c4ccccc4)c3cc21]
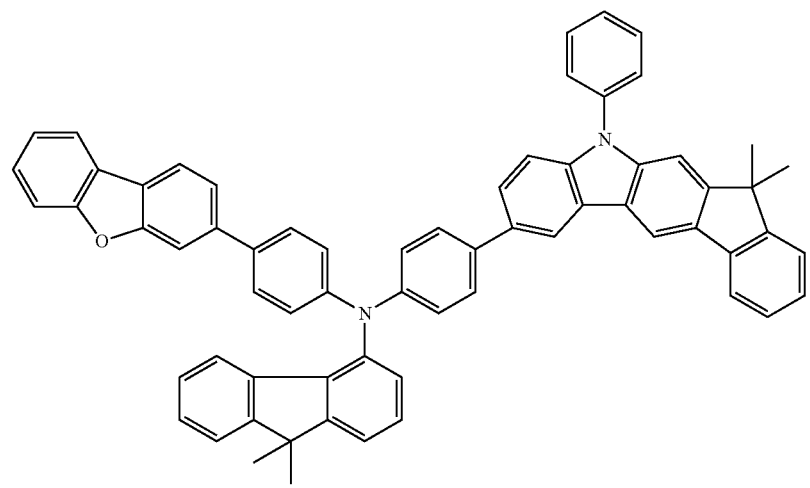 [SMILES: CC1(C)c2ccccc2-c2cc3c4cc(-c5ccc(N(c6ccc(-c7ccc8c(c7)oc7ccccc78)cc6)c6cccc7c6-c6ccccc6C7(C)C)cc5)ccc4n(-c4ccccc4)c3cc21]

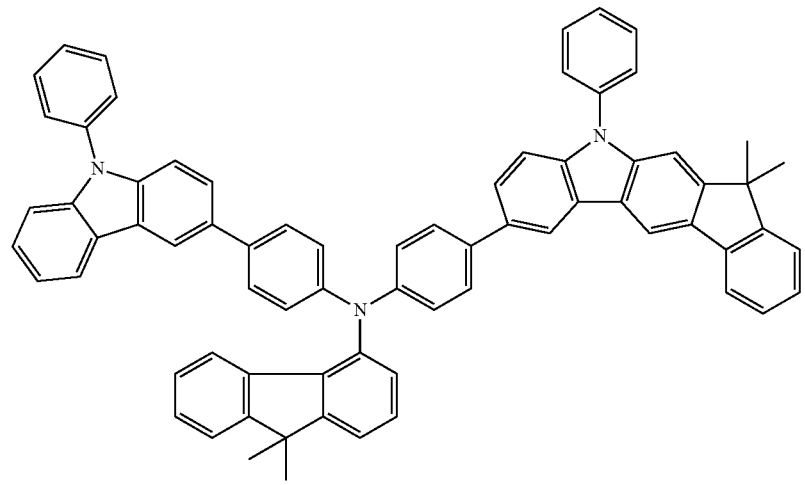 [SMILES: CC1(C)c2ccccc2-c2cc3c4cc(-c5ccc(N(c6ccc(-c7ccc8c(c7)c7ccccc7n8-c7ccccc7)cc6)c6cccc7c6-c6ccccc6C7(C)C)cc5)ccc4n(-c4ccccc4)c3cc21]
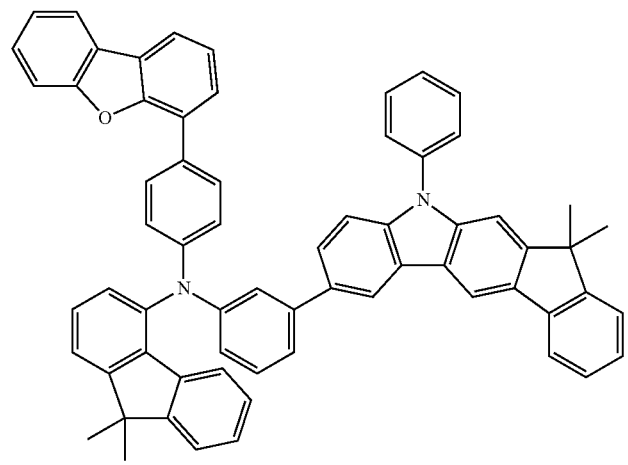 [SMILES: CC1(C)c2ccccc2-c2cc3c4cc(-c5cccc(N(c6ccc(-c7cccc8c7oc7ccccc78)cc6)c6cccc7c6-c6ccccc6C7(C)C)c5)ccc4n(-c4ccccc4)c3cc21]
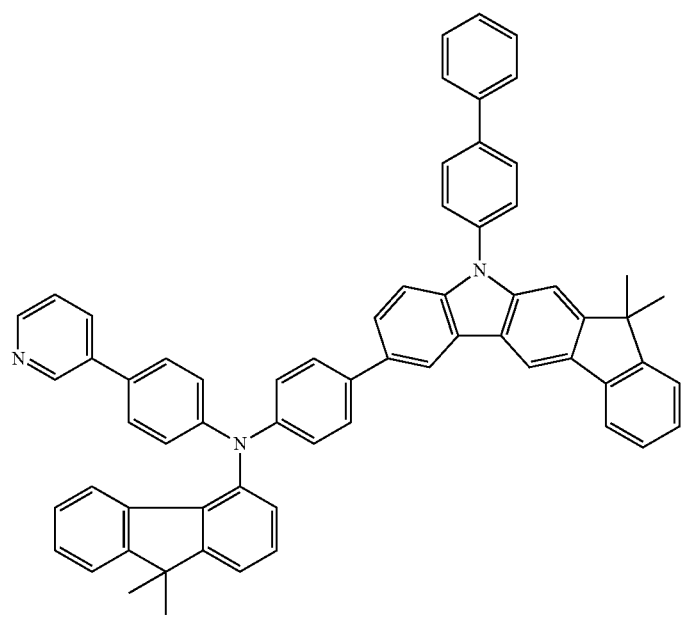 [SMILES: CC1(C)c2ccccc2-c2cc3c4cc(-c5ccc(N(c6ccc(-c7cccnc7)cc6)c6cccc7c6-c6ccccc6C7(C)C)cc5)ccc4n(-c4ccc(-c5ccccc5)cc4)c3cc21]

-continued
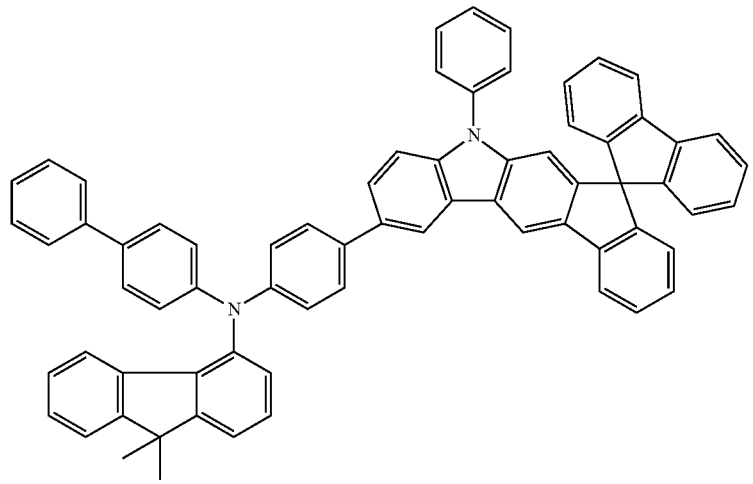 [SMILES: CC1(C)c2ccccc2-c2c(N(c3ccc(-c4ccccc4)cc3)c3ccc(-c4ccc5c(c4)c4cc6c(cc4n5-c4ccccc4)C4(c5ccccc5-c5ccccc54)c4ccccc4-6)cc3)cccc21]
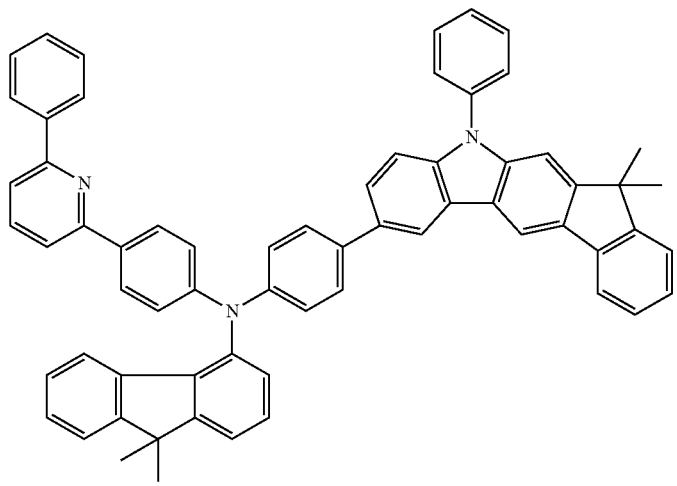 [SMILES: CC1(C)c2ccccc2-c2cc3c4cc(-c5ccc(N(c6ccc(-c7cccc(-c8ccccc8)n7)cc6)c6cccc7c6-c6ccccc6C7(C)C)cc5)ccc4n(-c4ccccc4)c3cc21]
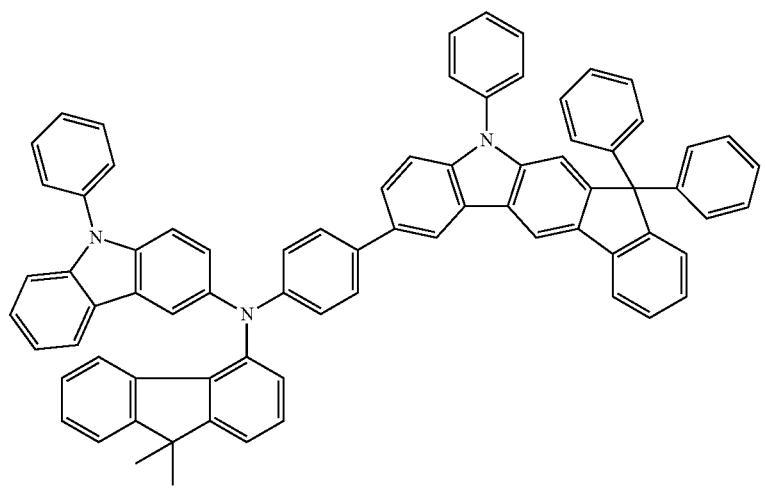 [SMILES: CC1(C)c2ccccc2-c2c(N(c3ccc(-c4ccc5c(c4)c4cc6c(cc4n5-c4ccccc4)C(c4ccccc4)(c4ccccc4)c4ccccc4-6)cc3)c3ccc4c(c3)c3ccccc3n4-c3ccccc3)cccc21]

-continued
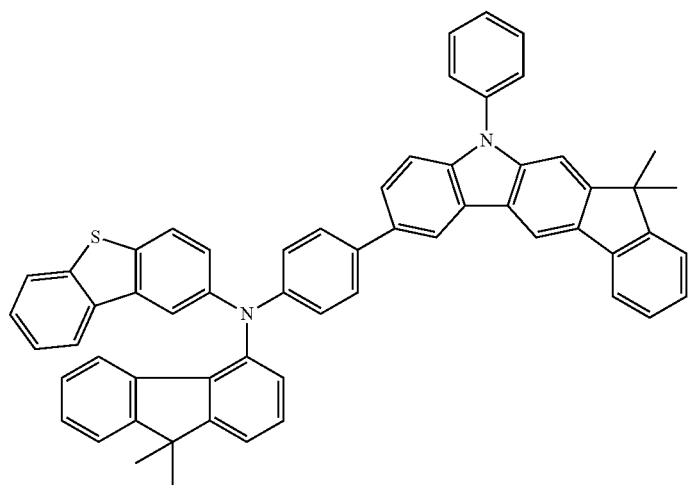 [SMILES: CC1(C)c2ccccc2-c2cc3c4cc(-c5ccc(N(c6ccc7sc8ccccc8c7c6)c6cccc7c6-c6ccccc6C7(C)C)cc5)ccc4n(-c4ccccc4)c3cc21]
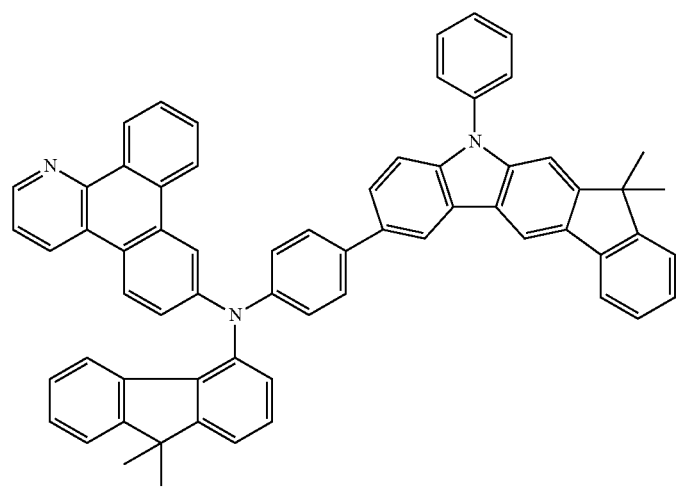 [SMILES: CC1(C)c2ccccc2-c2cc3c4cc(-c5ccc(N(c6ccc7c(c6)c6ccccc6c6ncccc76)c6cccc7c6-c6ccccc6C7(C)C)cc5)ccc4n(-c4ccccc4)c3cc21]
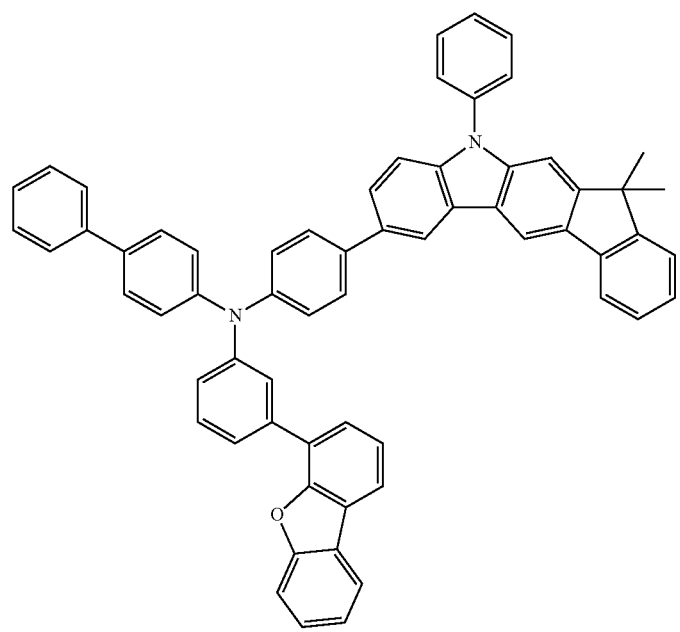 [SMILES: CC1(C)c2ccccc2-c2cc3c4cc(-c5ccc(N(c6ccc(-c7ccccc7)cc6)c6cccc(-c7cccc8c7oc7ccccc78)c6)cc5)ccc4n(-c4ccccc4)c3cc21]

-continued
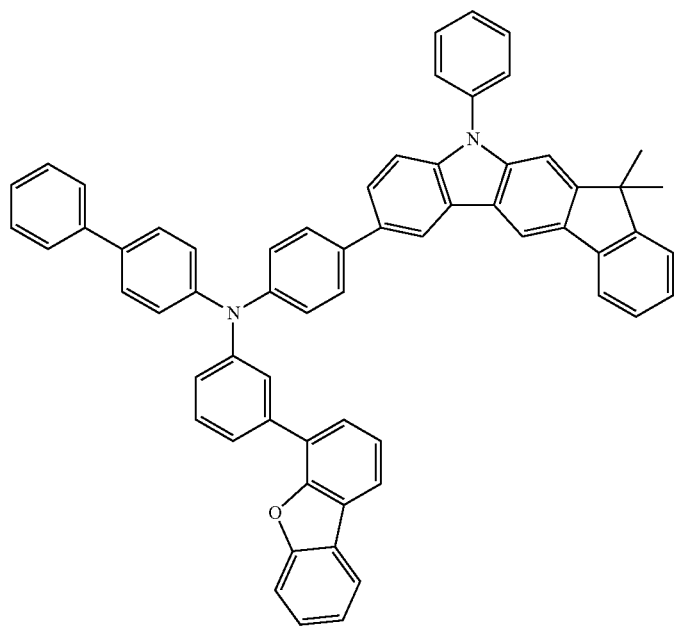 [SMILES: CC1(C)c2ccccc2-c2cc3c4cc(-c5ccc(N(c6ccc(-c7ccccc7)cc6)c6cccc(-c7cccc8c7oc7ccccc78)c6)cc5)ccc4n(-c4ccccc4)c3cc21]
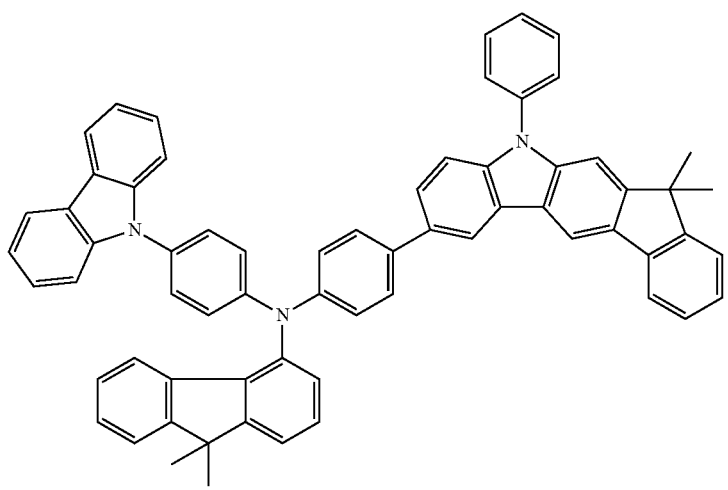 [SMILES: CC1(C)c2ccccc2-c2cc3c4cc(-c5ccc(N(c6ccc(-n7c8ccccc8c8ccccc87)cc6)c6cccc7c6-c6ccccc6C7(C)C)cc5)ccc4n(-c4ccccc4)c3cc21]
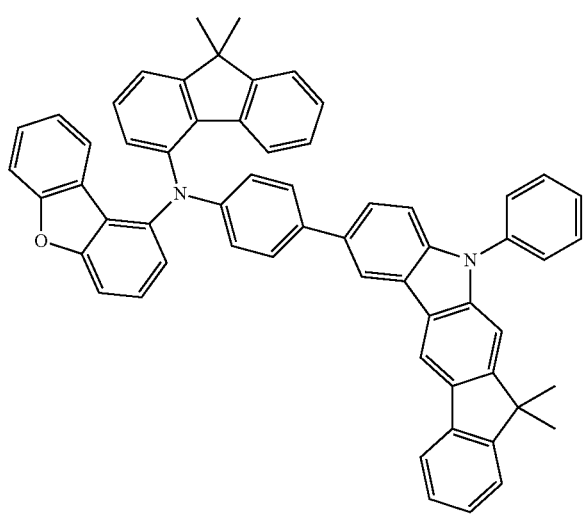 [SMILES: CC1(C)c2ccccc2-c2cc3c4cc(-c5ccc(N(c6cccc7c6-c6ccccc6C7(C)C)c6cccc7oc8ccccc8c67)cc5)ccc4n(-c4ccccc4)c3cc21]

-continued
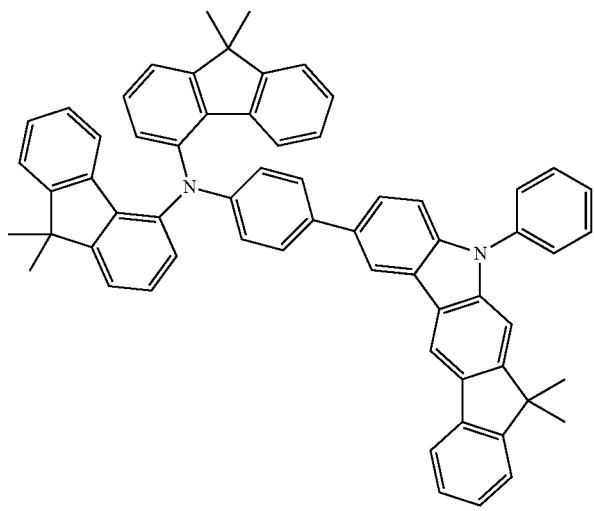 [SMILES: CC1(C)c2ccccc2-c2cc3c4cc(-c5ccc(N(c6cccc7c6-c6ccccc6C7(C)C)c6cccc7c6-c6ccccc6C7(C)C)cc5)ccc4n(-c4ccccc4)c3cc21]
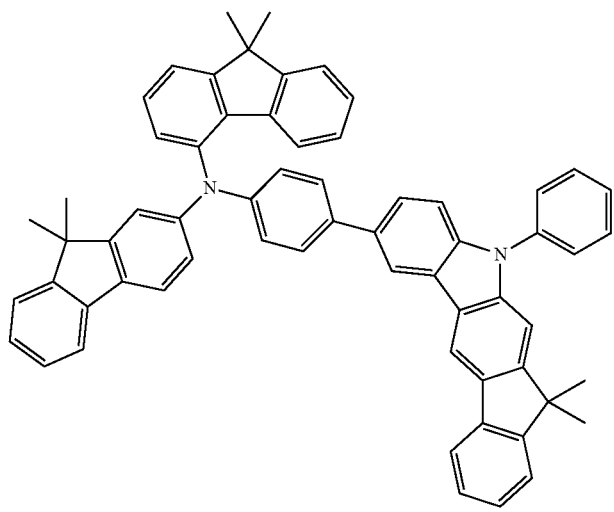 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C4(C)C)cc21]
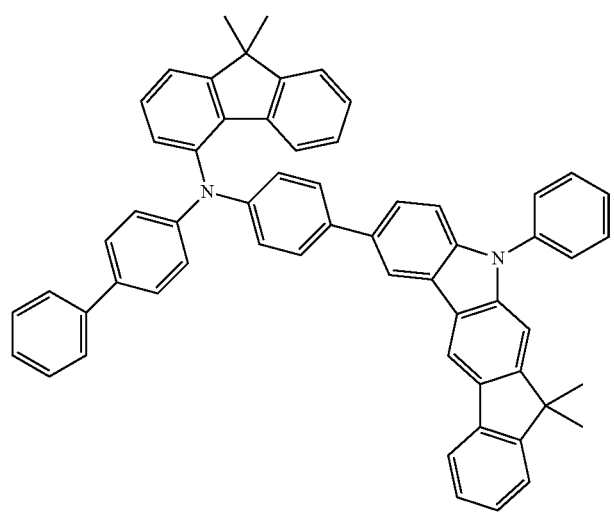 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4ccccc4)c3cc21]

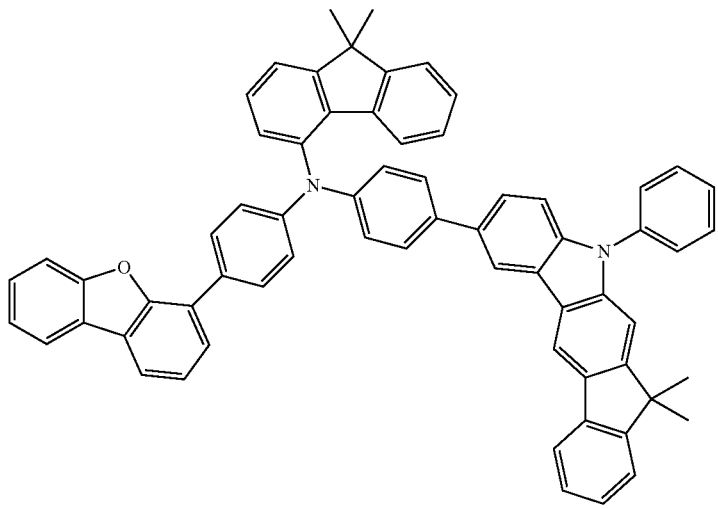 [SMILES: CC1(C)c2ccccc2-c2cc3c4cc(-c5ccc(N(c6ccc(-c7cccc8c7sc7ccccc78)cc6)c6cccc7c6-c6ccccc6C7(C)C)cc5)ccc4n(-c4ccccc4)c3cc21]
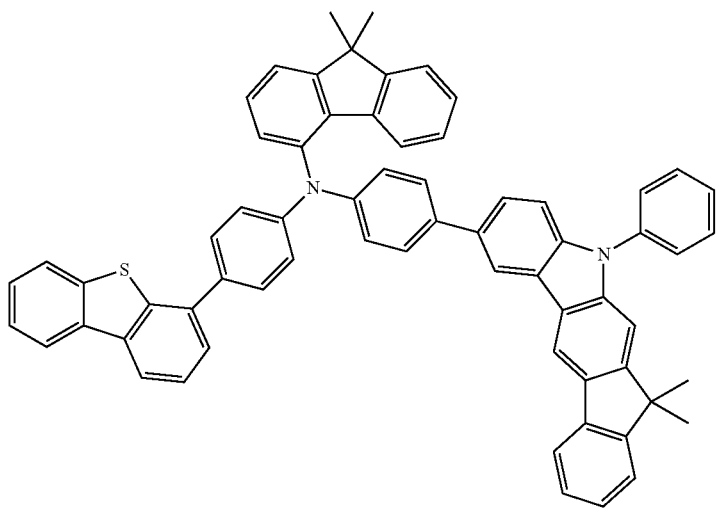
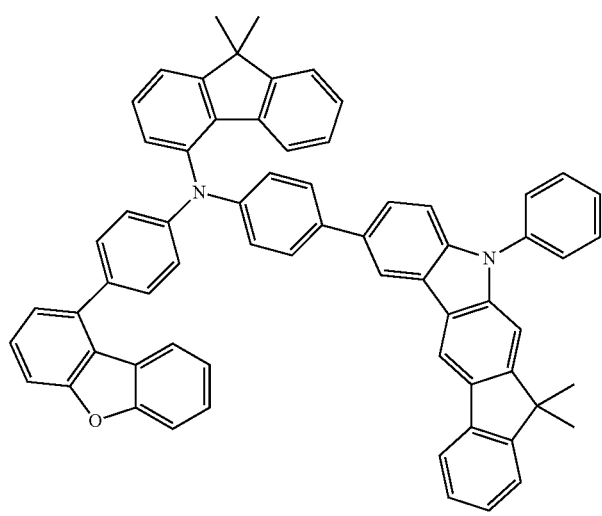 [SMILES: CC1(C)c2ccccc2-c2cc3c4cc(-c5ccc(N(c6ccc(-c7cccc8oc9ccccc9c78)cc6)c6cccc7c6-c6ccccc6C7(C)C)cc5)ccc4n(-c4ccccc4)c3cc21]

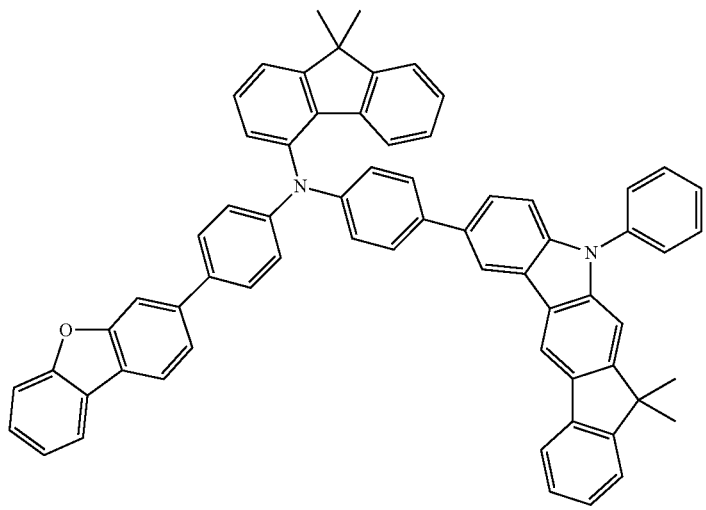 [SMILES: CC1(C)c2ccccc2-c2cc3c4cc(-c5ccc(N(c6ccc(-c7ccc8c(c7)oc7ccccc78)cc6)c6cccc7c6-c6ccccc6C7(C)C)cc5)ccc4n(-c4ccccc4)c3cc21]
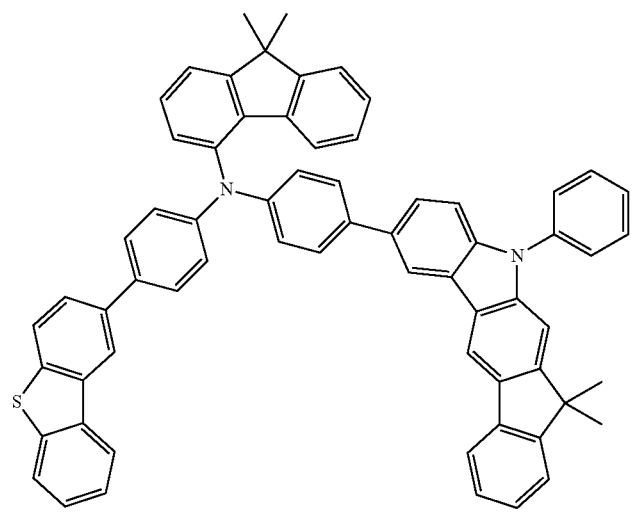 [SMILES: CC1(C)c2ccccc2-c2cc3c4cc(-c5ccc(N(c6ccc(-c7ccc8sc9ccccc9c8c7)cc6)c6cccc7c6-c6ccccc6C7(C)C)cc5)ccc4n(-c4ccccc4)c3cc21]
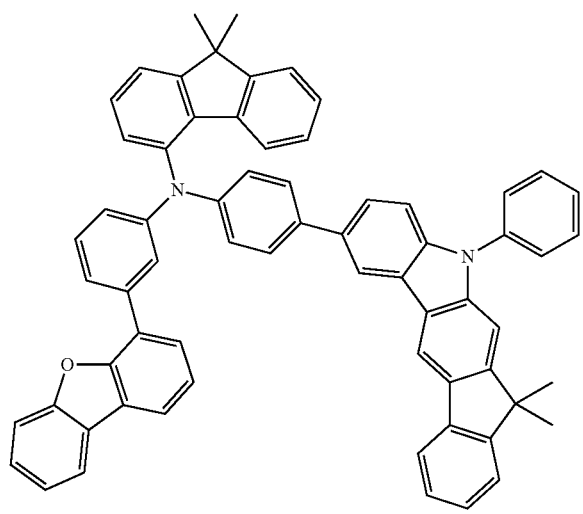 [SMILES: CC1(C)c2ccccc2-c2cc3c4cc(-c5ccc(N(c6cccc(-c7cccc8c7oc7ccccc78)c6)c6cccc7c6-c6ccccc6C7(C)C)cc5)ccc4n(-c4ccccc4)c3cc21]

-continued
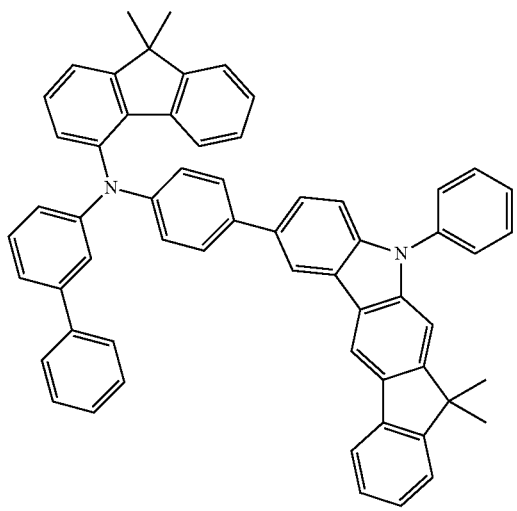 [SMILES: CC1(C)c2ccccc2-c2cc3c4cc(-c5ccc(N(c6cccc(-c7ccccc7)c6)c6cccc7c6-c6ccccc6C7(C)C)cc5)ccc4n(-c4ccccc4)c3cc21]
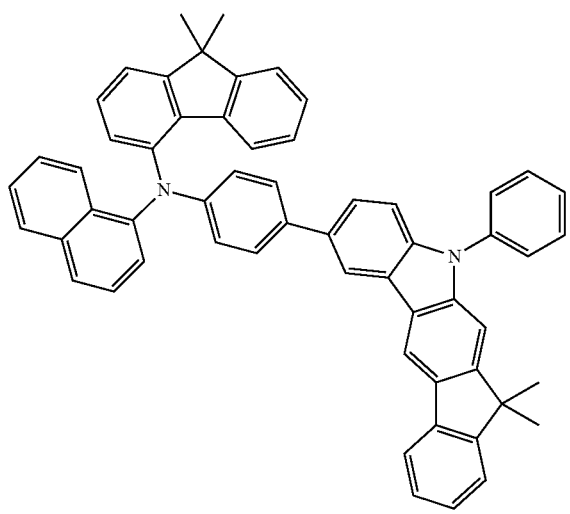 [SMILES: CC1(C)c2ccccc2-c2cc3c4cc(-c5ccc(N(c6cccc7c6-c6ccccc6C7(C)C)c6cccc7ccccc67)cc5)ccc4n(-c4ccccc4)c3cc21]
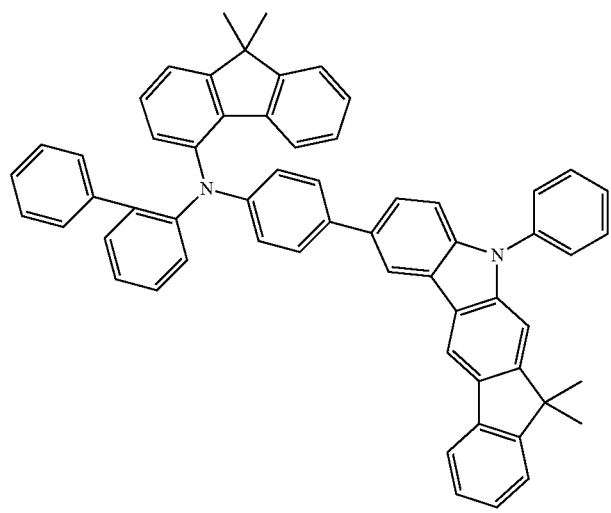 [SMILES: CC1(C)c2ccccc2-c2cc3c4cc(-c5ccc(N(c6ccccc6-c6ccccc6)c6cccc7c6-c6ccccc6C7(C)C)cc5)ccc4n(-c4ccccc4)c3cc21]

-continued
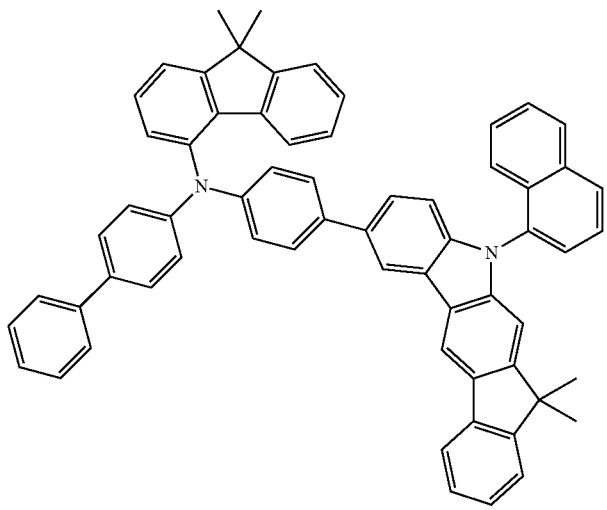 [SMILES: CC1(C)c2ccccc2-c2cc3c4cc(-c5ccc(N(c6ccc(-c7ccccc7)cc6)c6cccc7c6-c6ccccc6C7(C)C)cc5)ccc4n(-c4cccc5ccccc45)c3cc21]
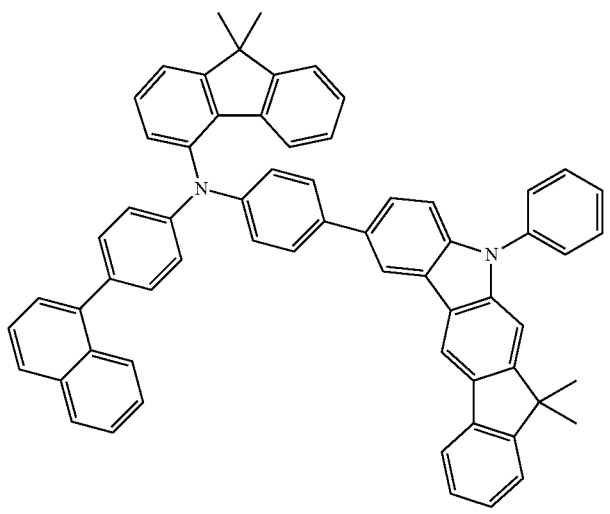 [SMILES: CC1(C)c2ccccc2-c2cc3c4cc(-c5ccc(N(c6ccc(-c7cccc8ccccc78)cc6)c6cccc7c6-c6ccccc6C7(C)C)cc5)ccc4n(-c4ccccc4)c3cc21]
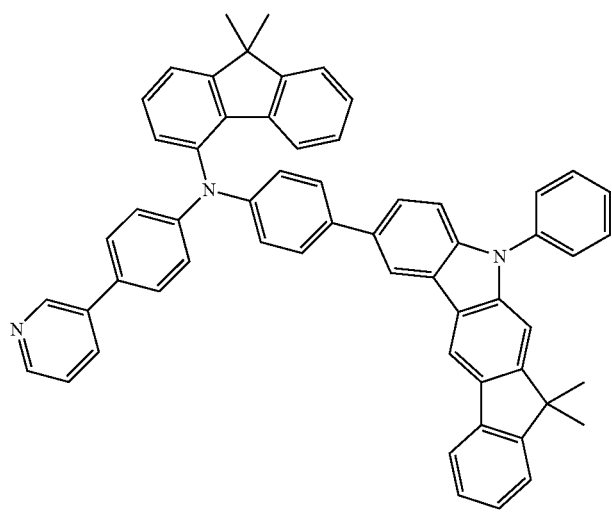 [SMILES: CC1(C)c2ccccc2-c2cc3c4cc(-c5ccc(N(c6ccc(-c7cccnc7)cc6)c6cccc7c6-c6ccccc6C7(C)C)cc5)ccc4n(-c4ccccc4)c3cc21]

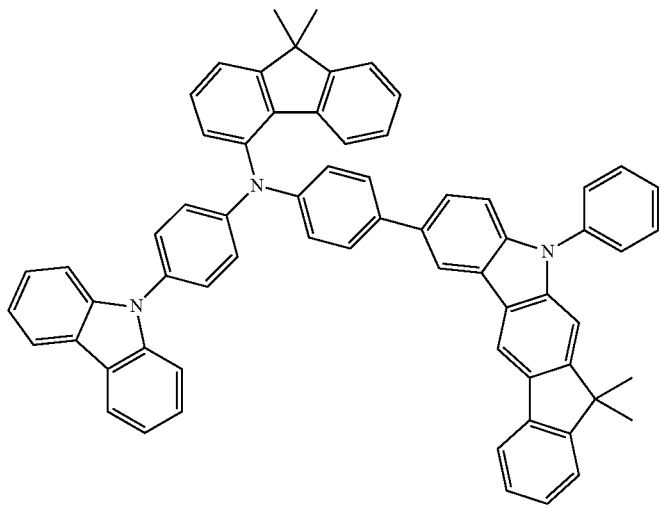 [SMILES: CC1(C)c2ccccc2-c2cc3c4cc(-c5ccc(N(c6ccc(-n7c8ccccc8c8ccccc87)cc6)c6cccc7c6-c6ccccc6C7(C)C)cc5)ccc4n(-c4ccccc4)c3cc21]
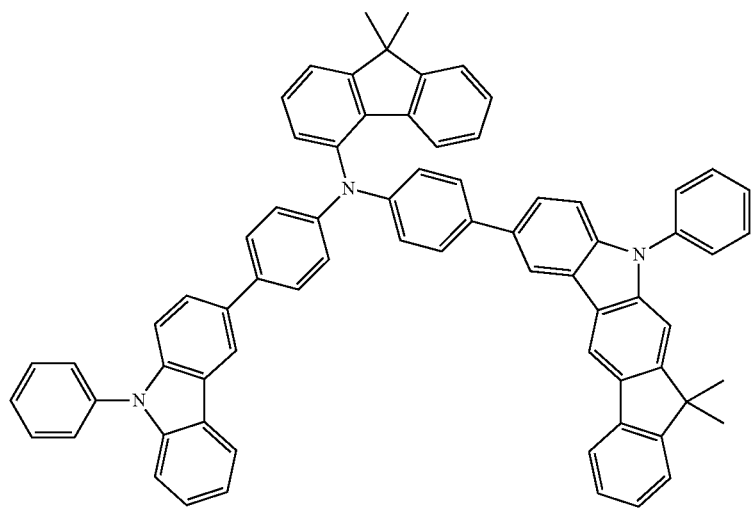 [SMILES: CC1(C)c2ccccc2-c2cc3c4cc(-c5ccc(N(c6ccc(-c7ccc8c(c7)c7ccccc7n8-c7ccccc7)cc6)c6cccc7c6-c6ccccc6C7(C)C)cc5)ccc4n(-c4ccccc4)c3cc21]
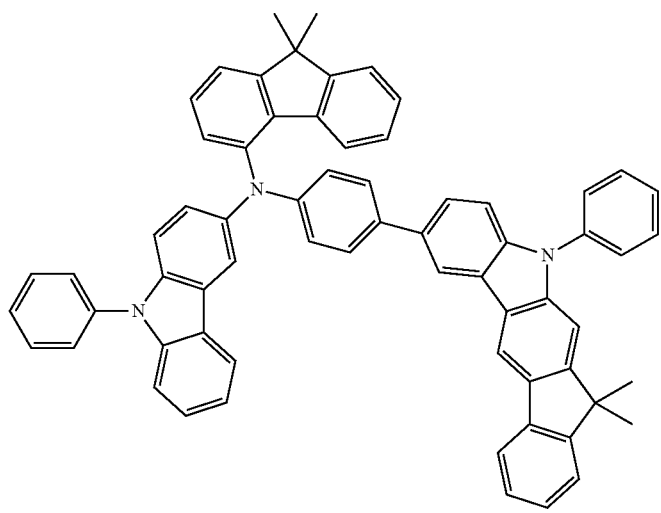 [SMILES: CC1(C)c2ccccc2-c2cc3c4cc(-c5ccc(N(c6ccc7c(c6)c6ccccc6n7-c6ccccc6)c6cccc7c6-c6ccccc6C7(C)C)cc5)ccc4n(-c4ccccc4)c3cc21]

-continued
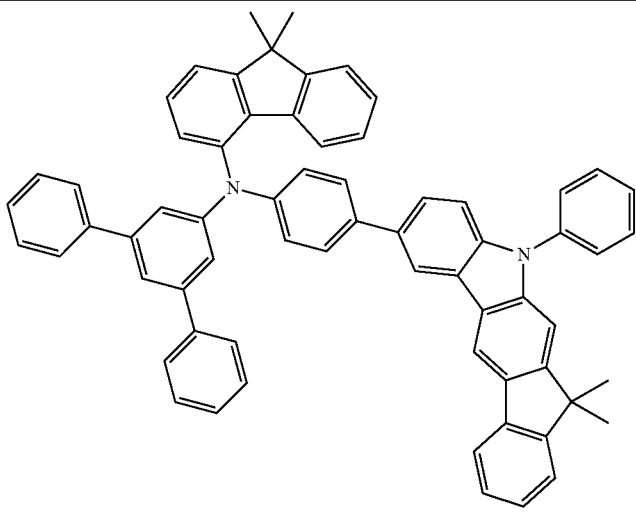
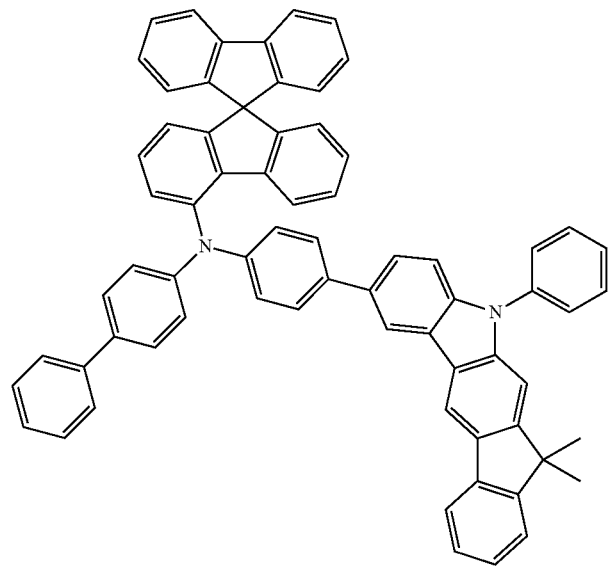 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccccc4)c3cc21]
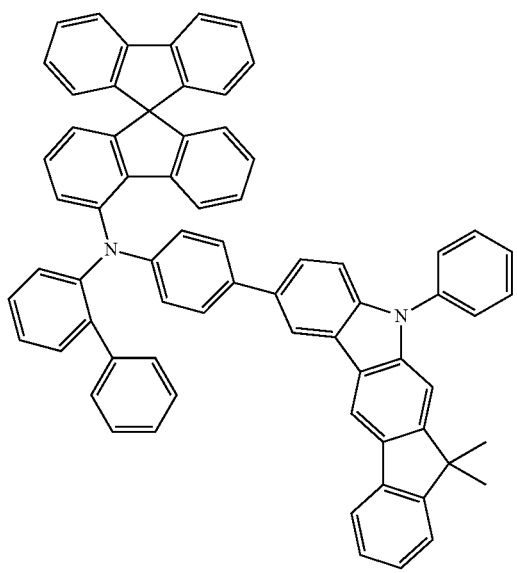 [SMILES: CC1(C)c2ccccc2-c2cc3c4cc(-c5ccc(N(c6ccccc6-c6ccccc6)c6cccc7c6-c6ccccc6C76c7ccccc7-c7ccccc76)cc5)ccc4n(-c4ccccc4)c3cc21]

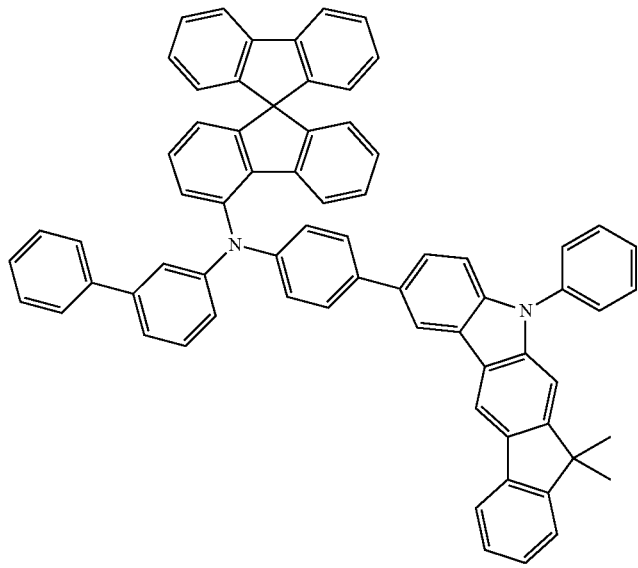 [SMILES: CC1(C)c2ccccc2-c2cc3c4cc(-c5ccc(N(c6cccc(-c7ccccc7)c6)c6cccc7c6-c6ccccc6C76c7ccccc7-c7ccccc76)cc5)ccc4n(-c4ccccc4)c3cc21]
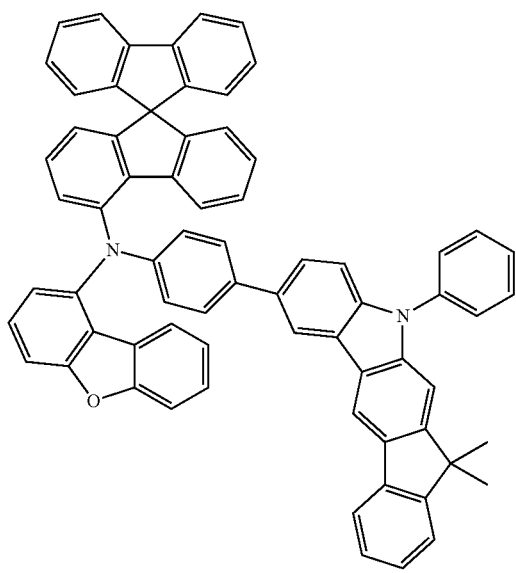 [SMILES: CC1(C)c2ccccc2-c2cc3c4cc(-c5ccc(N(c6cccc7c6-c6ccccc6C76c7ccccc7-c7ccccc76)c6cccc7oc8ccccc8c67)cc5)ccc4n(-c4ccccc4)c3cc21]

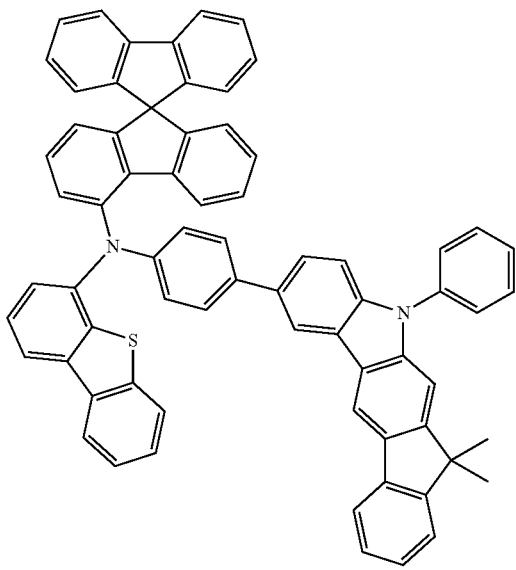 [SMILES: CC1(C)c2ccccc2-c2cc3c4cc(-c5ccc(N(c6cccc7c6-c6ccccc6C76c7ccccc7-c7ccccc76)c6cccc7c6sc6ccccc67)cc5)ccc4n(-c4ccccc4)c3cc21]
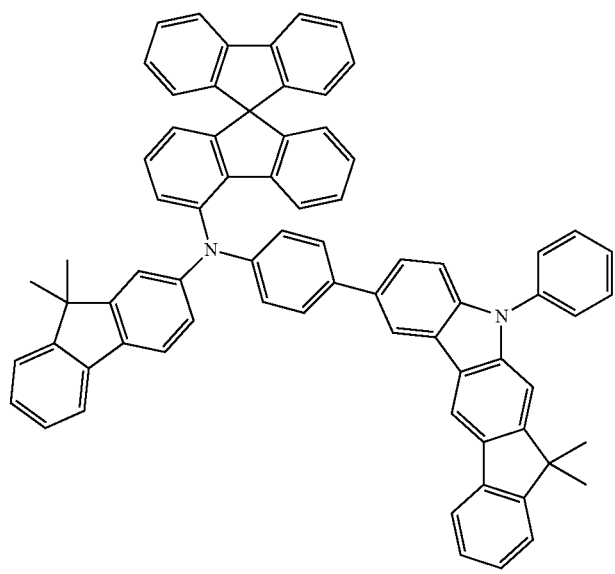 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3-c3ccccc3C43c4ccccc4-c4ccccc43)cc21]

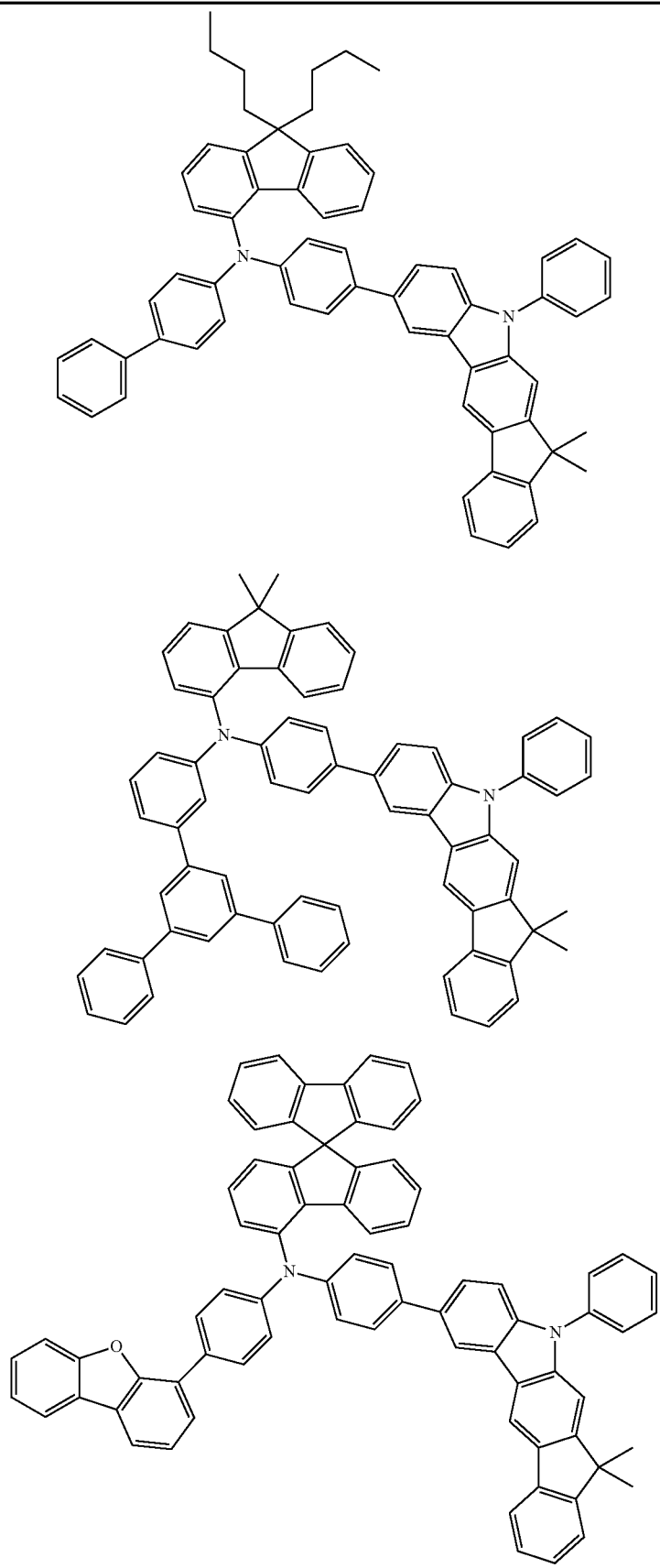

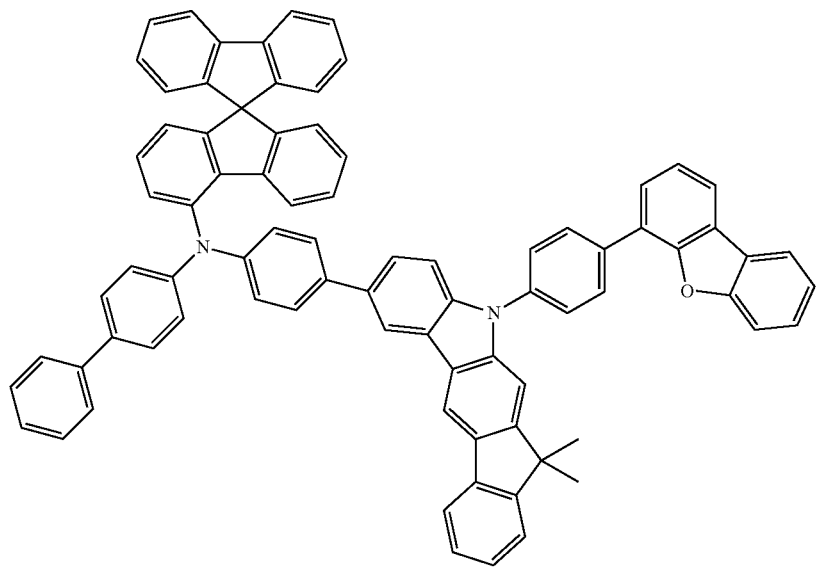 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccc(-c5cccc6c5oc5ccccc56)cc4)c3cc21]
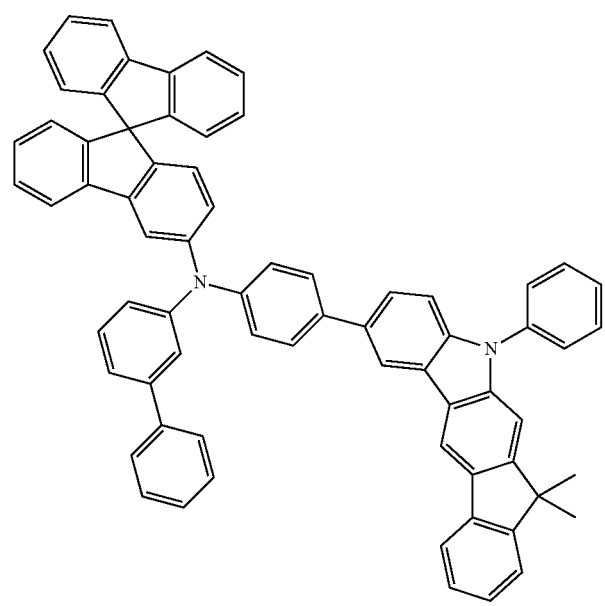 [SMILES: CC1(C)c2ccccc2-c2cc3c4cc(-c5ccc(N(c6cccc(-c7ccccc7)c6)c6ccc7c(c6)-c6ccccc6C76c7ccccc7-c7ccccc76)cc5)ccc4n(-c4ccccc4)c3cc21]

-continued
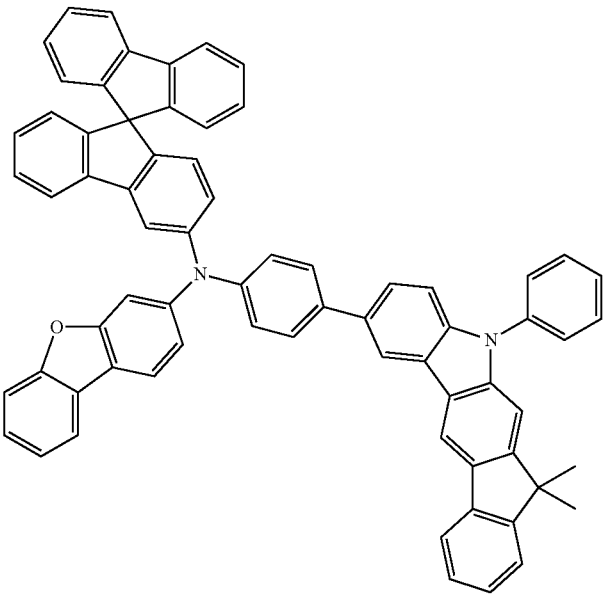 [SMILES: CC1(C)c2ccccc2-c2cc3c4cc(-c5ccc(N(c6ccc7c(c6)-c6ccccc6C76c7ccccc7-c7ccccc76)c6ccc7c(c6)oc6ccccc67)cc5)ccc4n(-c4ccccc4)c3cc21]
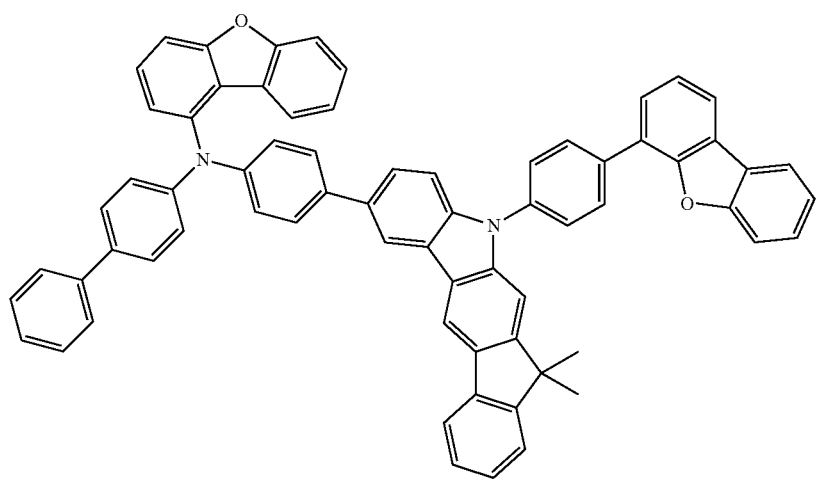 [SMILES: CC1(C)c2ccccc2-c2cc3c4cc(-c5ccc(N(c6ccc(-c7ccccc7)cc6)c6cccc7oc8ccccc8c67)cc5)ccc4n(-c4ccc(-c5cccc6c5oc5ccccc56)cc4)c3cc21]
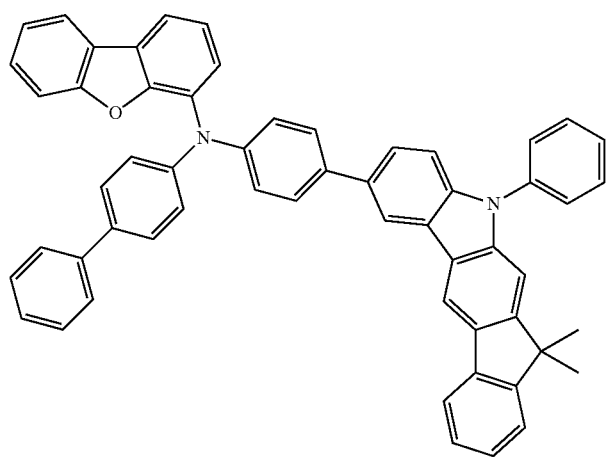 [SMILES: CC1(C)c2ccccc2-c2cc3c4cc(-c5ccc(N(c6ccc(-c7ccccc7)cc6)c6cccc7c6oc6ccccc67)cc5)ccc4n(-c4ccccc4)c3cc21]

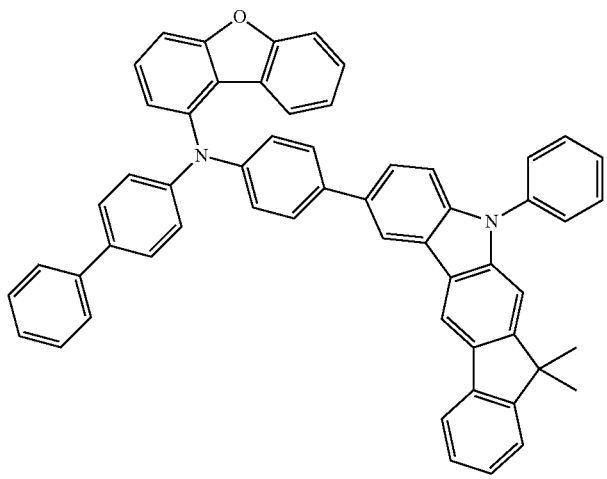
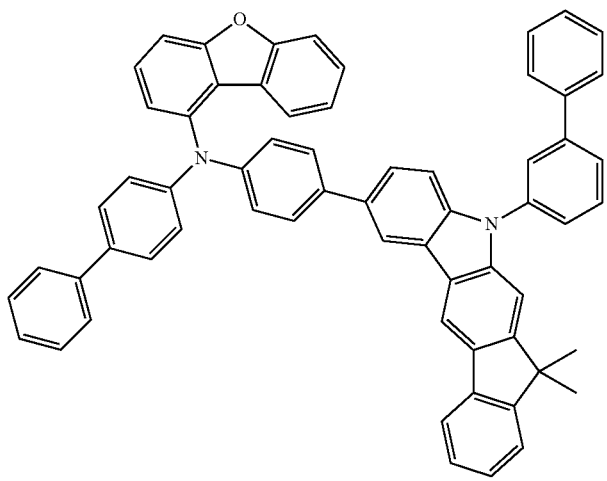 [SMILES: CC1(C)c2ccccc2-c2cc3c4cc(-c5ccc(N(c6ccc(-c7ccccc7)cc6)c6cccc7oc8ccccc8c67)cc5)ccc4n(-c4cccc(-c5ccccc5)c4)c3cc21]
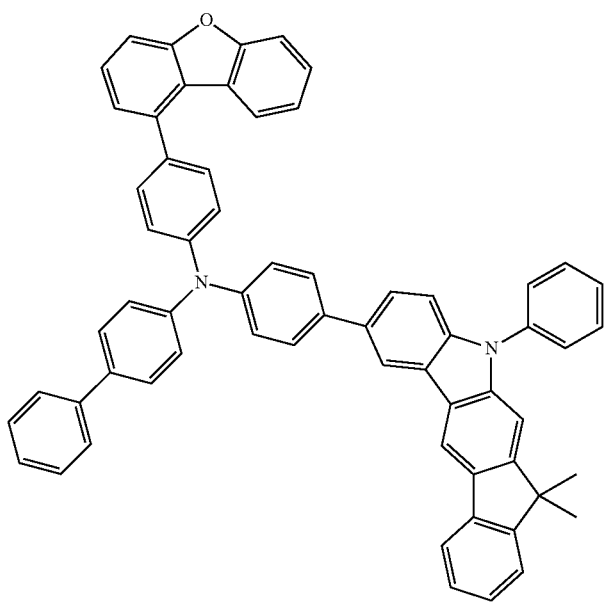 [SMILES: CC1(C)c2ccccc2-c2cc3c4cc(-c5ccc(N(c6ccc(-c7ccccc7)cc6)c6ccc(-c7cccc8oc9ccccc9c78)cc6)cc5)ccc4n(-c4ccccc4)c3cc21]

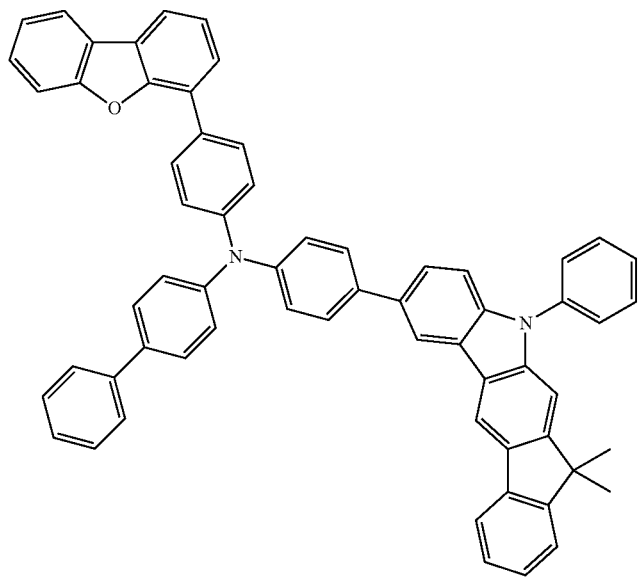 [SMILES: CC1(C)c2ccccc2-c2cc3c4cc(-c5ccc(N(c6ccc(-c7ccccc7)cc6)c6ccc(-c7cccc8c7oc7ccccc78)cc6)cc5)ccc4n(-c4ccccc4)c3cc21]
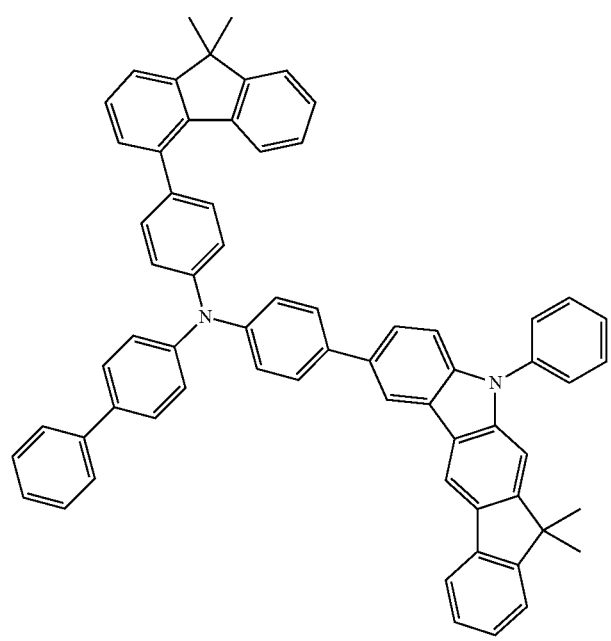 [SMILES: CC1(C)c2ccccc2-c2cc3c4cc(-c5ccc(N(c6ccc(-c7ccccc7)cc6)c6ccc(-c7cccc8c7-c7ccccc7C8(C)C)cc6)cc5)ccc4n(-c4ccccc4)c3cc21]

-continued
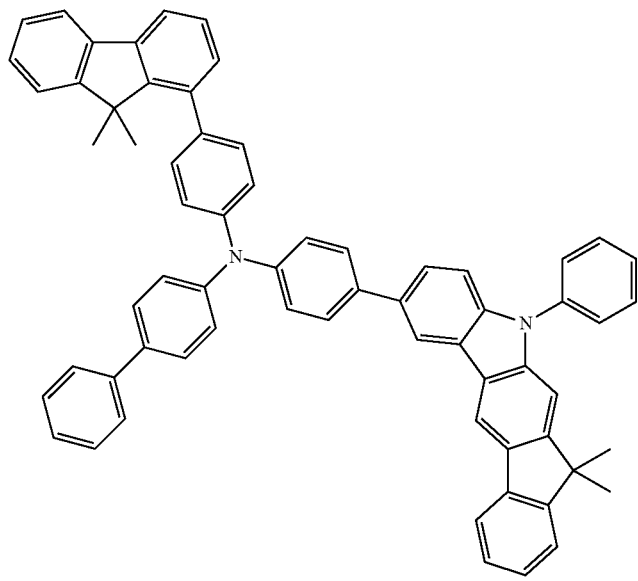 [SMILES: CC1(C)c2ccccc2-c2cc3c4cc(-c5ccc(N(c6ccc(-c7ccccc7)cc6)c6ccc(-c7cccc8c7C(C)(C)c7ccccc7-8)cc6)cc5)ccc4n(-c4ccccc4)c3cc21]
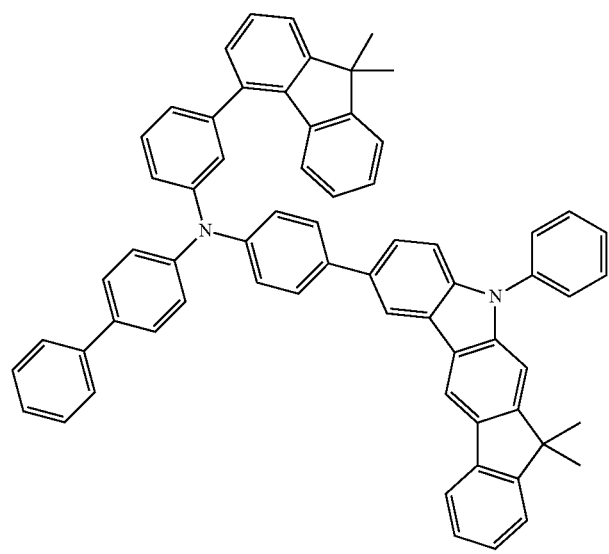 [SMILES: CC1(C)c2ccccc2-c2cc3c4cc(-c5ccc(N(c6ccc(-c7ccccc7)cc6)c6cccc(-c7cccc8c7-c7ccccc7C8(C)C)c6)cc5)ccc4n(-c4ccccc4)c3cc21]

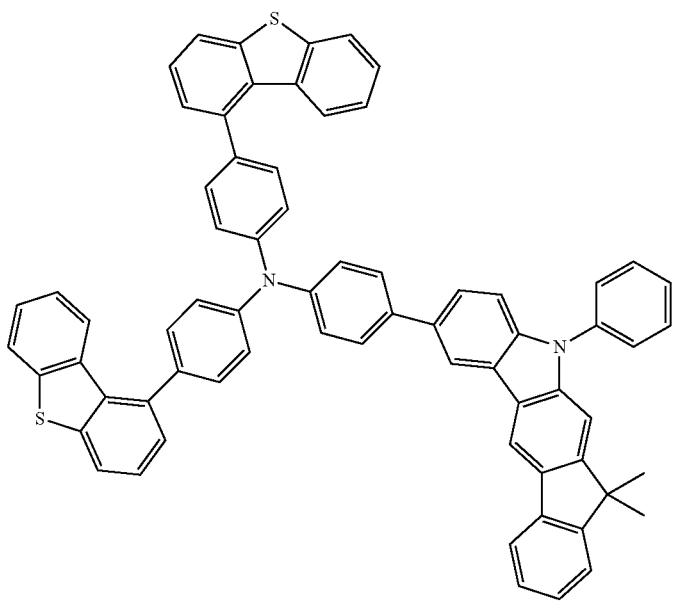 [SMILES: CC1(C)c2ccccc2-c2cc3c4cc(-c5ccc(N(c6ccc(-c7cccc8sc9ccccc9c78)cc6)c6ccc(-c7cccc8sc9ccccc9c78)cc6)cc5)ccc4n(-c4ccccc4)c3cc21]
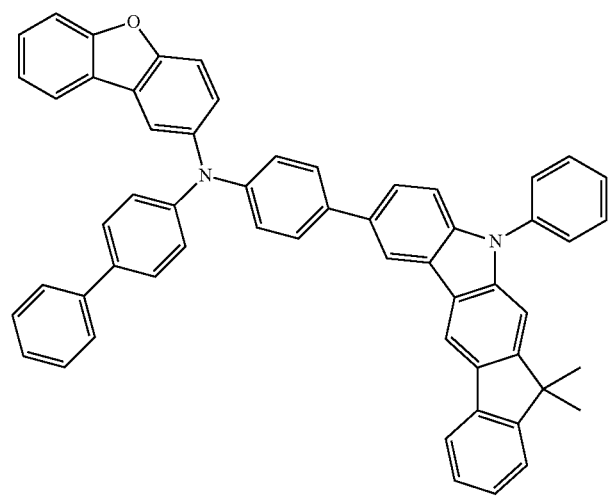 [SMILES: CC1(C)c2ccccc2-c2cc3c4cc(-c5ccc(N(c6ccc(-c7ccccc7)cc6)c6ccc7oc8ccccc8c7c6)cc5)ccc4n(-c4ccccc4)c3cc21]

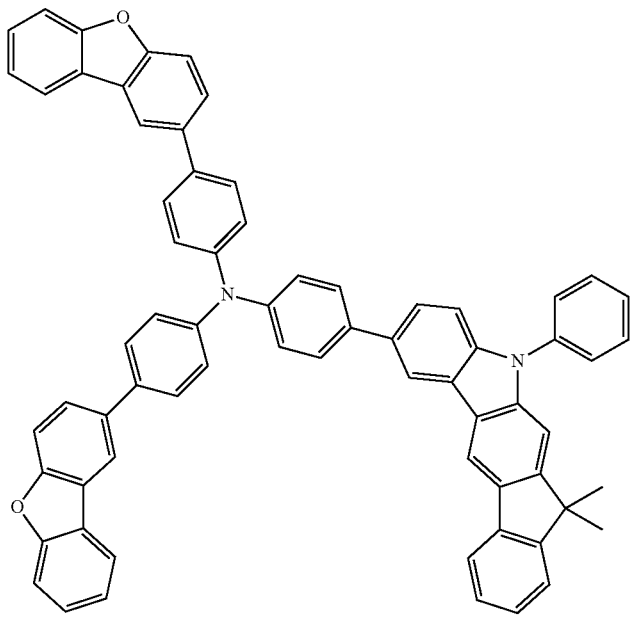 [SMILES: CC1(C)c2ccccc2-c2cc3c4cc(-c5ccc(N(c6ccc(-c7ccc8oc9ccccc9c8c7)cc6)c6ccc(-c7ccc8oc9ccccc9c8c7)cc6)cc5)ccc4n(-c4ccccc4)c3cc21]
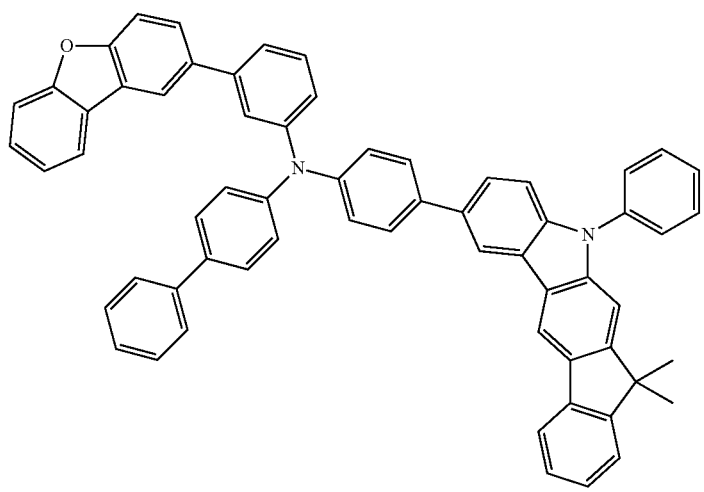 [SMILES: CC1(C)c2ccccc2-c2cc3c4cc(-c5ccc(N(c6ccc(-c7ccccc7)cc6)c6cccc(-c7ccc8oc9ccccc9c8c7)c6)cc5)ccc4n(-c4ccccc4)c3cc21]

-continued
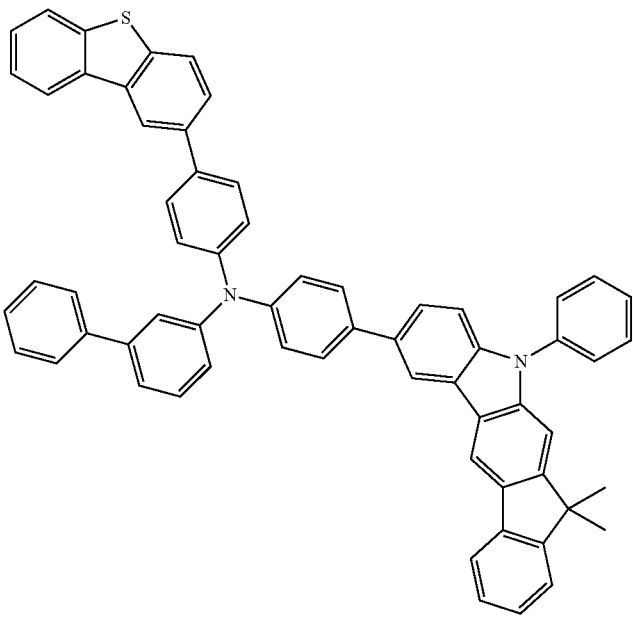 [SMILES: CC1(C)c2ccccc2-c2cc3c4cc(-c5ccc(N(c6ccc(-c7ccc8sc9ccccc9c8c7)cc6)c6cccc(-c7ccccc7)c6)cc5)ccc4n(-c4ccccc4)c3cc21]
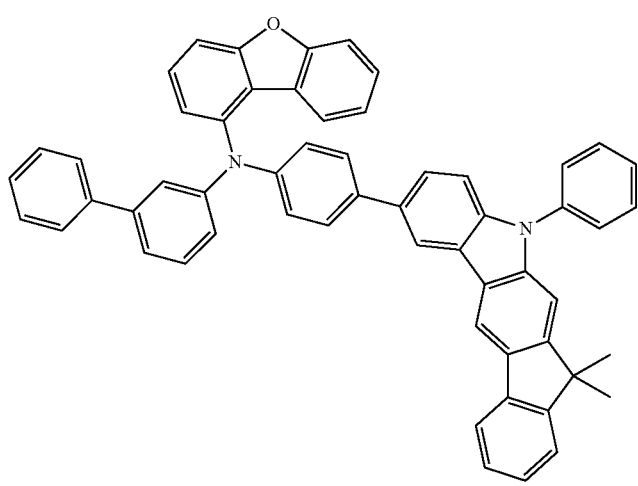 [SMILES: CC1(C)c2ccccc2-c2cc3c4cc(-c5ccc(N(c6cccc(-c7ccccc7)c6)c6cccc7oc8ccccc8c67)cc5)ccc4n(-c4ccccc4)c3cc21]
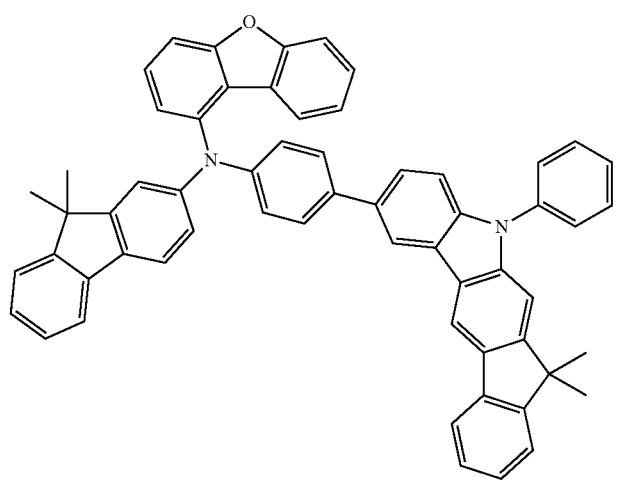 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4oc5ccccc5c34)cc21]

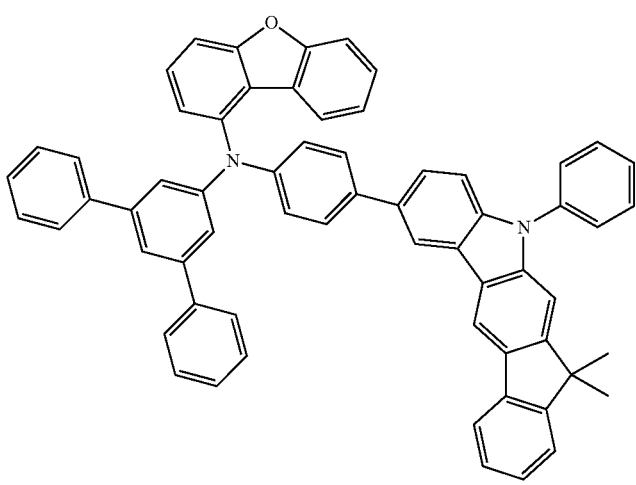 [SMILES: CC1(C)c2ccccc2-c2cc3c4cc(-c5ccc(N(c6cc(-c7ccccc7)cc(-c7ccccc7)c6)c6cccc7oc8ccccc8c67)cc5)ccc4n(-c4ccccc4)c3cc21]

-continued
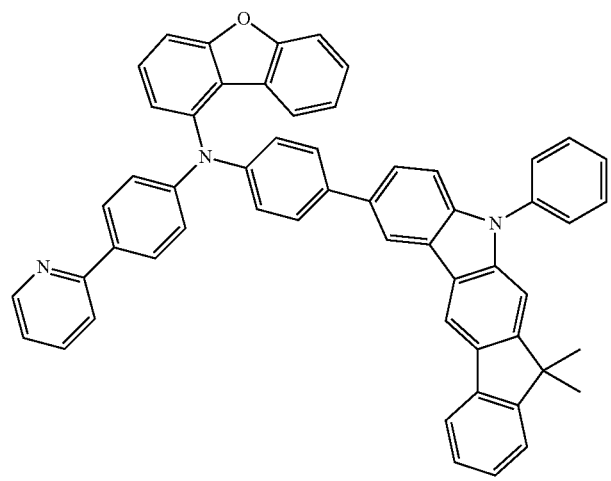 [SMILES: CC1(C)c2ccccc2-c2cc3c4cc(-c5ccc(N(c6ccc(-c7ccccn7)cc6)c6cccc7oc8ccccc8c67)cc5)ccc4n(-c4ccccc4)c3cc21]
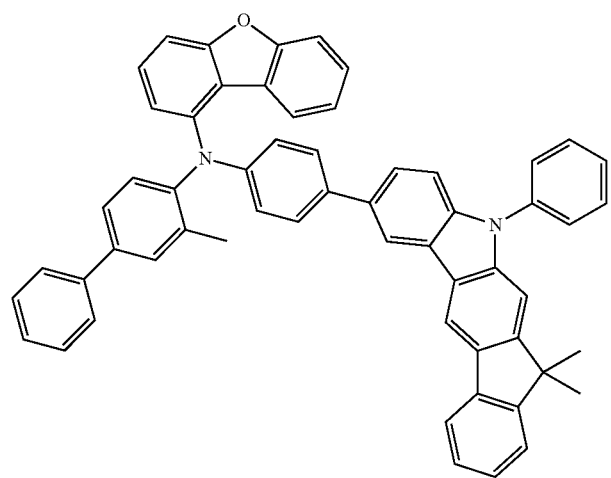 [SMILES: Cc1cc(-c2ccccc2)ccc1N(c1ccc(-c2ccc3c(c2)c2cc4c(cc2n3-c2ccccc2)C(C)(C)c2ccccc2-4)cc1)c1cccc2oc3ccccc3c12]
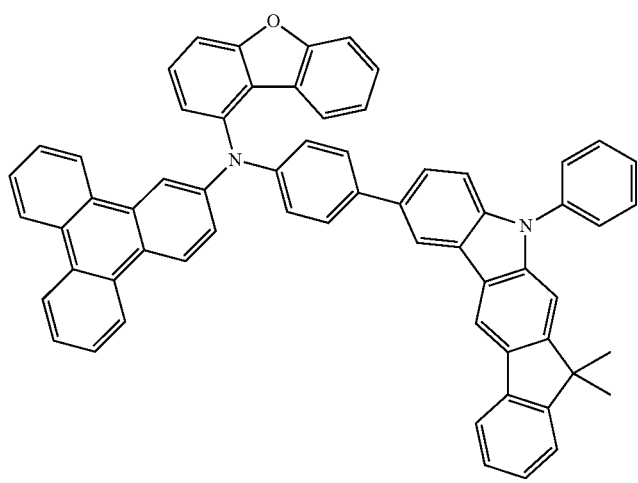 [SMILES: CC1(C)c2ccccc2-c2cc3c4cc(-c5ccc(N(c6ccc7c8ccccc8c8ccccc8c7c6)c6cccc7oc8ccccc8c67)cc5)ccc4n(-c4ccccc4)c3cc21]

-continued
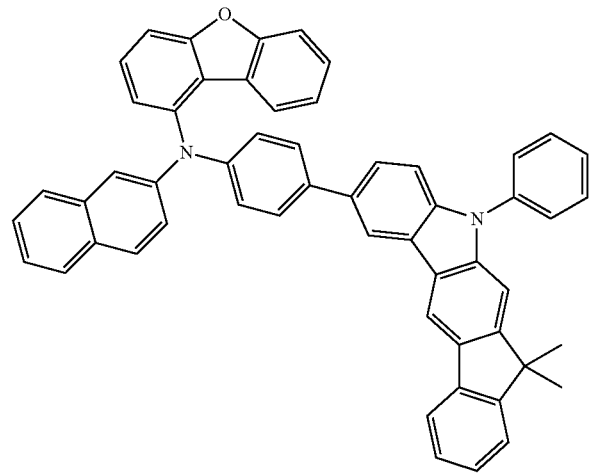 [SMILES: CC1(C)c2ccccc2-c2cc3c4cc(-c5ccc(N(c6ccc7ccccc7c6)c6cccc7oc8ccccc8c67)cc5)ccc4n(-c4ccccc4)c3cc21]
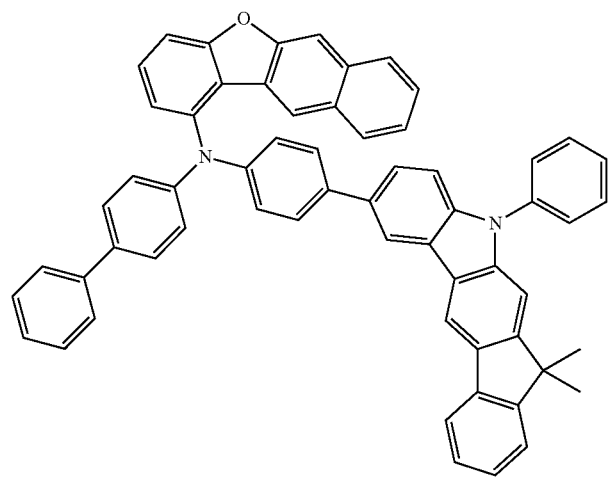 [SMILES: CC1(C)c2ccccc2-c2cc3c4cc(-c5ccc(N(c6ccc(-c7ccccc7)cc6)c6cccc7oc8cc9ccccc9cc8c67)cc5)ccc4n(-c4ccccc4)c3cc21]
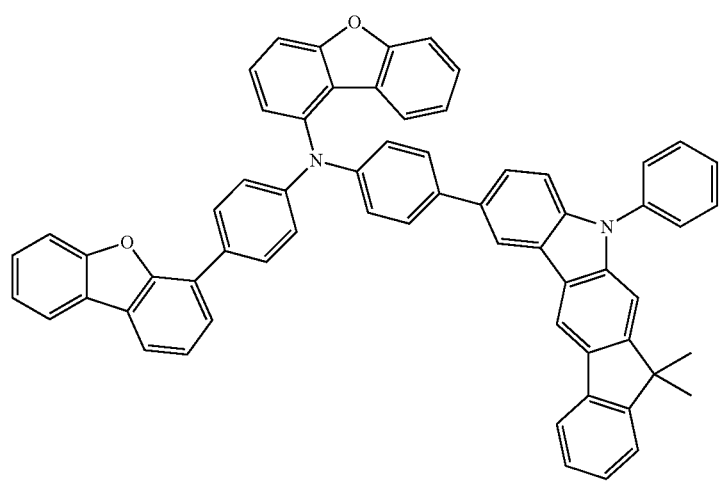

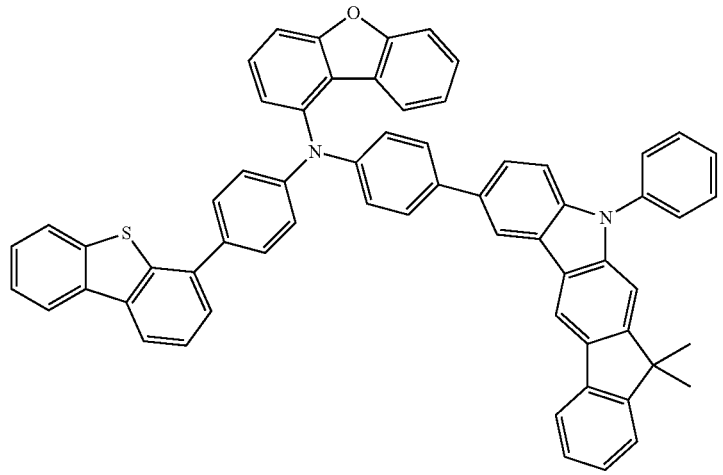 [SMILES: CC1(C)c2ccccc2-c2cc3c4cc(-c5ccc(N(c6ccc(-c7cccc8c7sc7ccccc78)cc6)c6cccc7oc8ccccc8c67)cc5)ccc4n(-c4ccccc4)c3cc21]
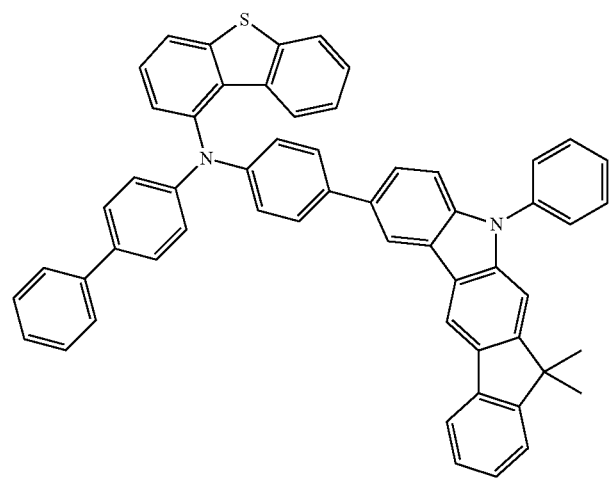 [SMILES: CC1(C)c2ccccc2-c2cc3c4cc(-c5ccc(N(c6ccc(-c7ccccc7)cc6)c6cccc7sc8ccccc8c67)cc5)ccc4n(-c4ccccc4)c3cc21]
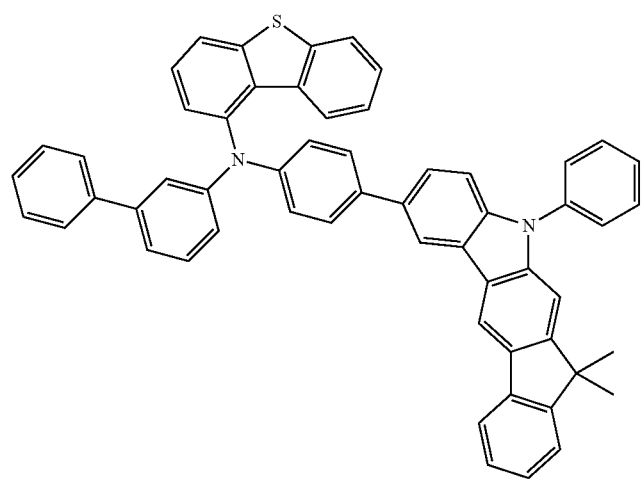

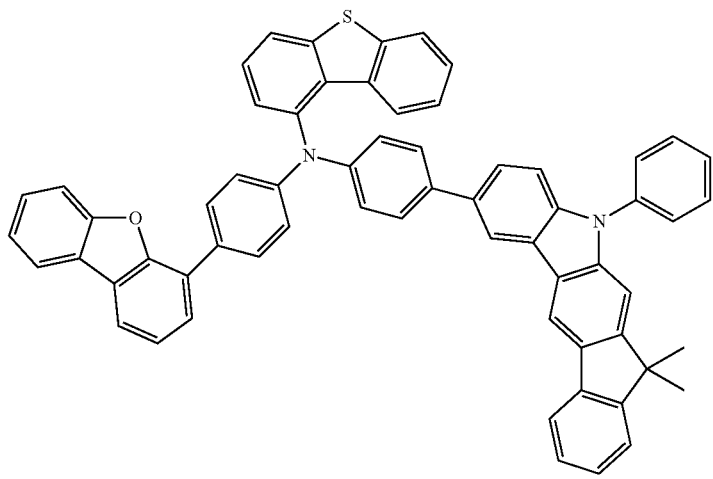 [SMILES: CC1(C)c2ccccc2-c2cc3c4cc(-c5ccc(N(c6ccc(-c7cccc8c7oc7ccccc78)cc6)c6cccc7sc8ccccc8c67)cc5)ccc4n(-c4ccccc4)c3cc21]
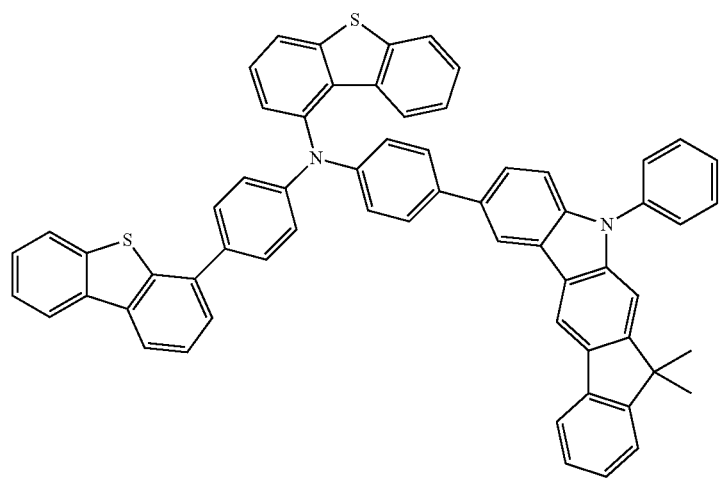
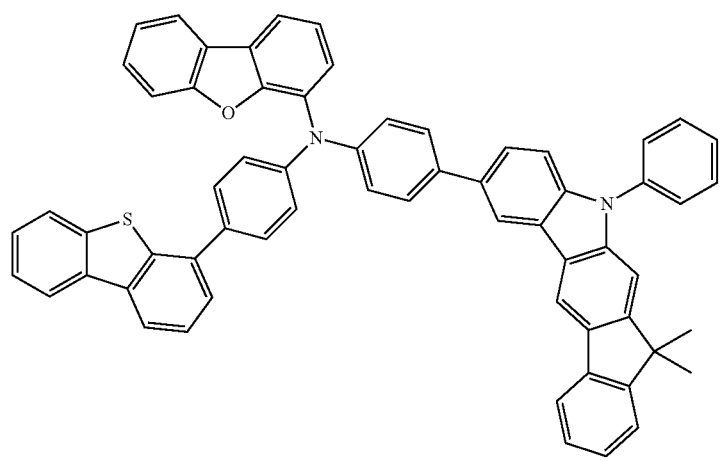 [SMILES: CC1(C)c2ccccc2-c2cc3c4cc(-c5ccc(N(c6ccc(-c7cccc8c7sc7ccccc78)cc6)c6cccc7c6oc6ccccc67)cc5)ccc4n(-c4ccccc4)c3cc21]

-continued
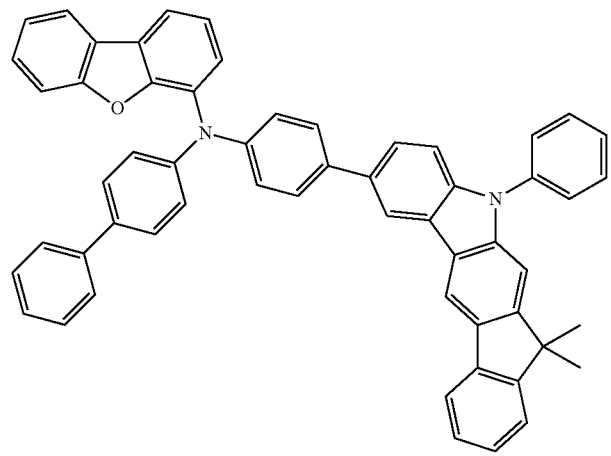 [SMILES: CC1(C)c2ccccc2-c2cc3c4cc(-c5ccc(N(c6ccc(-c7ccccc7)cc6)c6cccc7c6oc6ccccc67)cc5)ccc4n(-c4ccccc4)c3cc21]
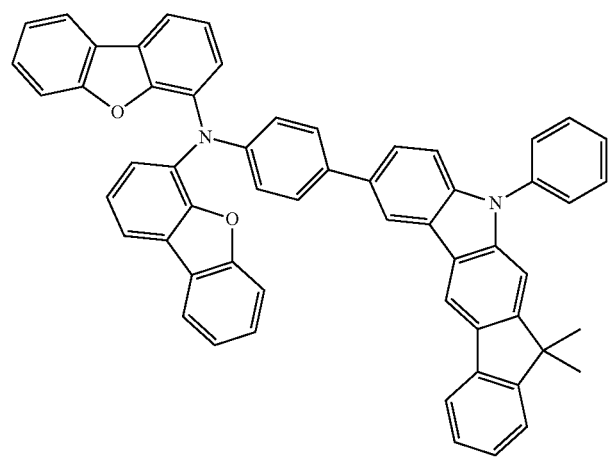 [SMILES: CC1(C)c2ccccc2-c2cc3c4cc(-c5ccc(N(c6cccc7c6oc6ccccc67)c6cccc7c6oc6ccccc67)cc5)ccc4n(-c4ccccc4)c3cc21]
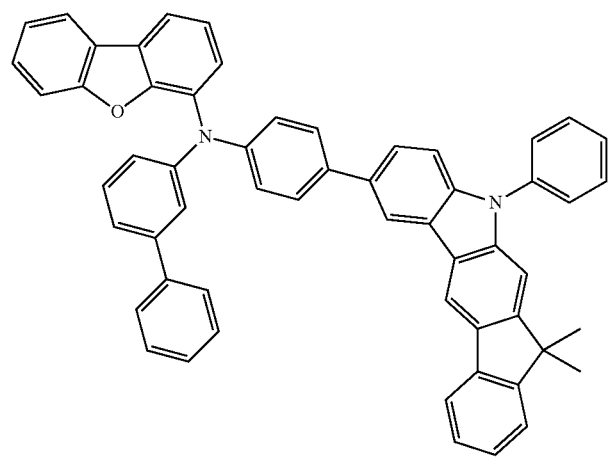 [SMILES: CC1(C)c2ccccc2-c2cc3c4cc(-c5ccc(N(c6cccc(-c7ccccc7)c6)c6cccc7c6oc6ccccc67)cc5)ccc4n(-c4ccccc4)c3cc21]

-continued
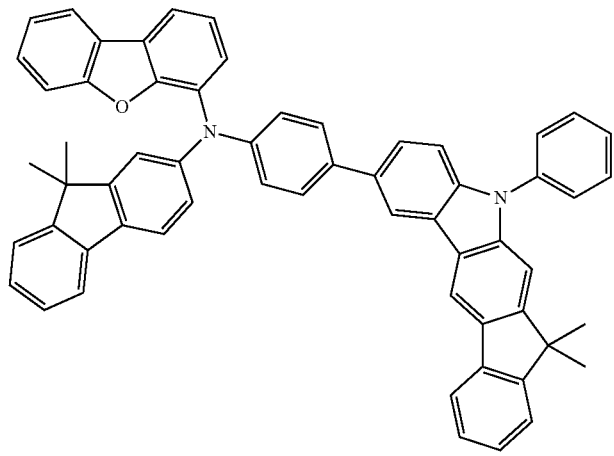 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3cccc4c3oc3ccccc34)cc21]
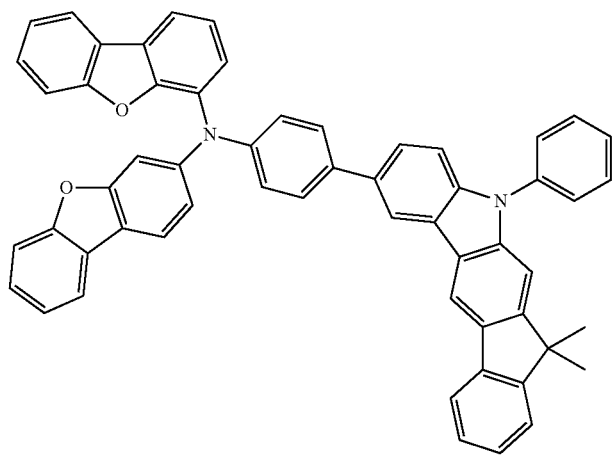 [SMILES: CC1(C)c2ccccc2-c2cc3c4cc(-c5ccc(N(c6ccc7c(c6)oc6ccccc67)c6cccc7c6oc6ccccc67)cc5)ccc4n(-c4ccccc4)c3cc21]
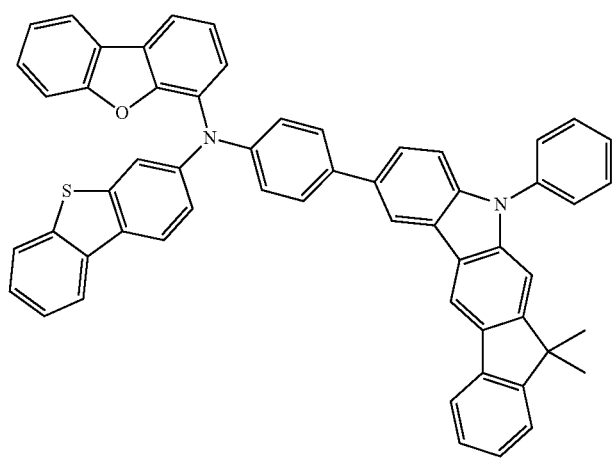

-continued
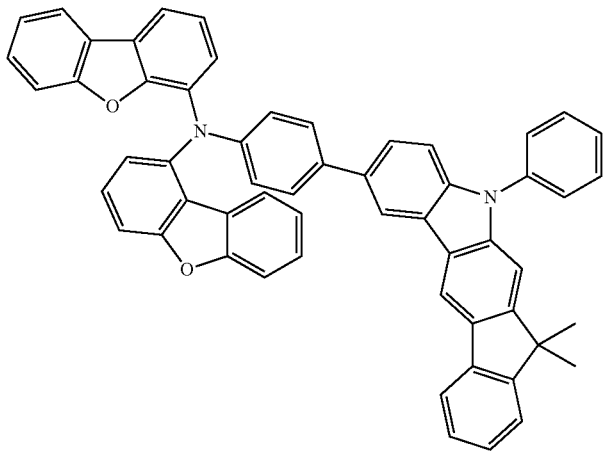 [SMILES: CC1(C)c2ccccc2-c2cc3c4cc(-c5ccc(N(c6cccc7c6oc6ccccc67)c6cccc7oc8ccccc8c67)cc5)ccc4n(-c4ccccc4)c3cc21]
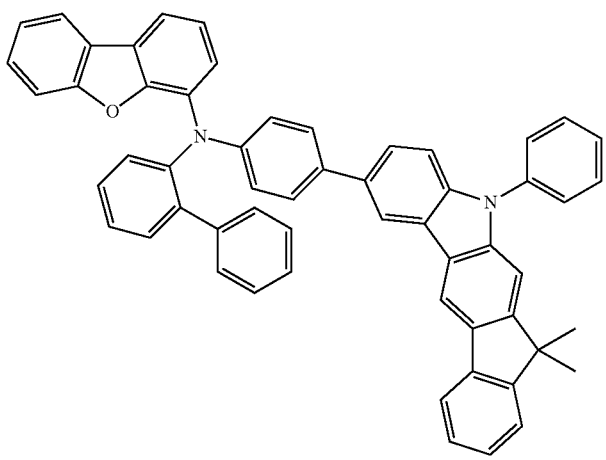 [SMILES: CC1(C)c2ccccc2-c2cc3c4cc(-c5ccc(N(c6ccccc6-c6ccccc6)c6cccc7c6oc6ccccc67)cc5)ccc4n(-c4ccccc4)c3cc21]
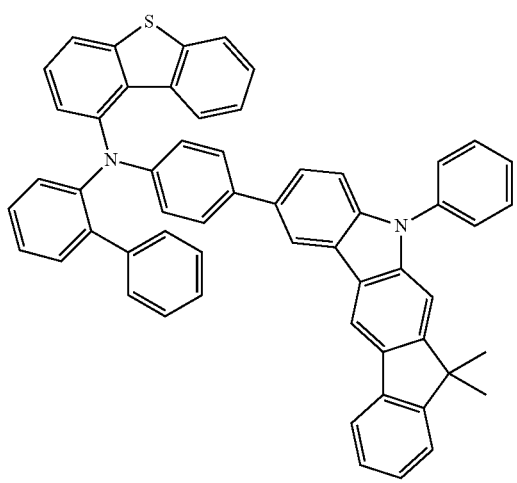 [SMILES: CC1(C)c2ccccc2-c2cc3c4cc(-c5ccc(N(c6ccccc6-c6ccccc6)c6cccc7sc8ccccc8c67)cc5)ccc4n(-c4ccccc4)c3cc21]

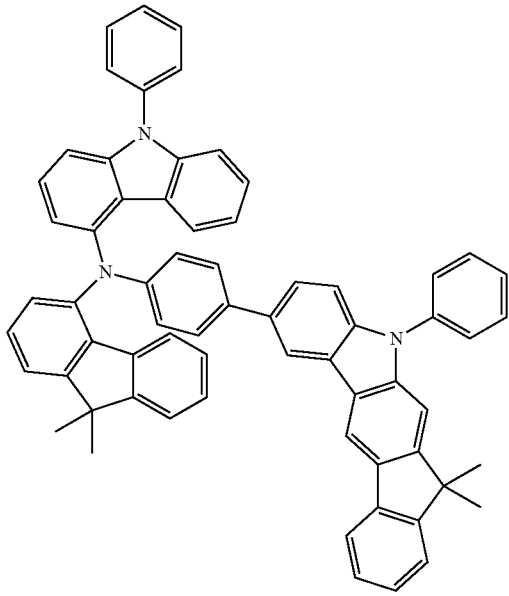 [SMILES: CC1(C)c2ccccc2-c2cc3c4cc(-c5ccc(N(c6cccc7c6-c6ccccc6C7(C)C)c6cccc7c6c6ccccc6n7-c6ccccc6)cc5)ccc4n(-c4ccccc4)c3cc21]
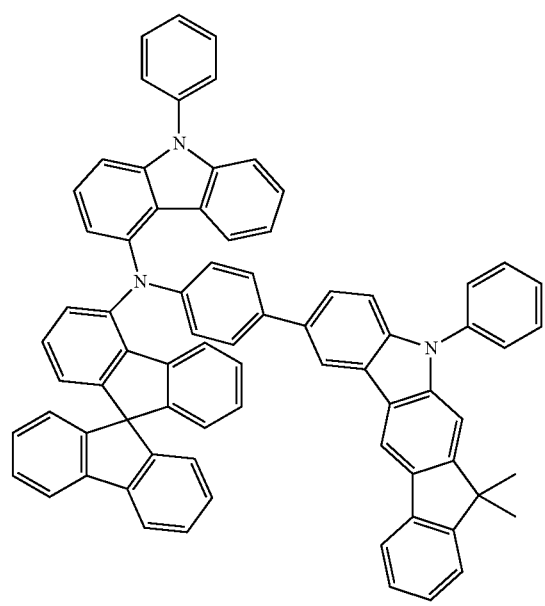 [SMILES: CC1(C)c2ccccc2-c2cc3c4cc(-c5ccc(N(c6cccc7c6-c6ccccc6C76c7ccccc7-c7ccccc76)c6cccc7c6c6ccccc6n7-c6ccccc6)cc5)ccc4n(-c4ccccc4)c3cc21]

-continued
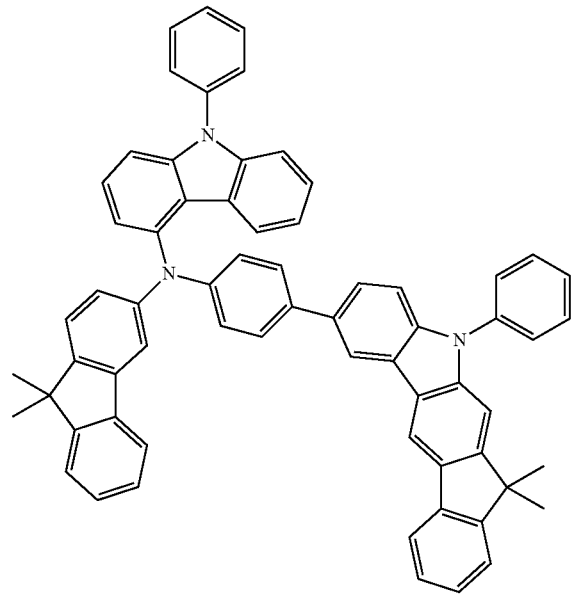 [SMILES: CC1(C)c2ccccc2-c2cc(N(c3ccc(-c4ccc5c(c4)c4cc6c(cc4n5-c4ccccc4)C(C)(C)c4ccccc4-6)cc3)c3cccc4c3c3ccccc3n4-c3ccccc3)ccc21]
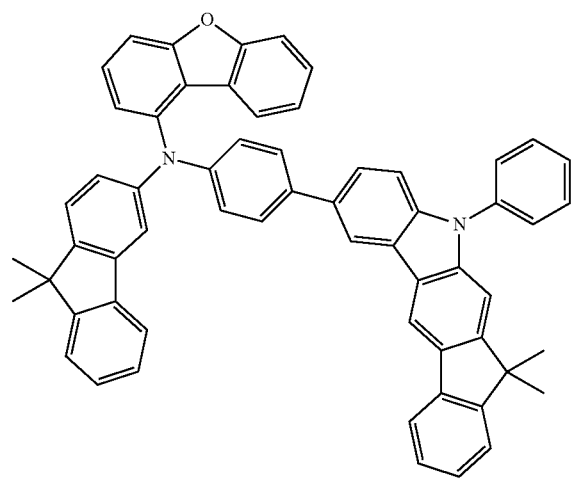 [SMILES: CC1(C)c2ccccc2-c2cc(N(c3ccc(-c4ccc5c(c4)c4cc6c(cc4n5-c4ccccc4)C(C)(C)c4ccccc4-6)cc3)c3cccc4oc5ccccc5c34)ccc21]
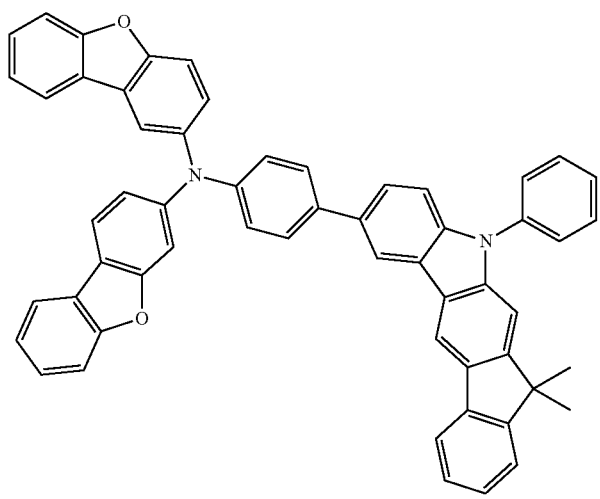 [SMILES: CC1(C)c2ccccc2-c2cc3c4cc(-c5ccc(N(c6ccc7c(c6)oc6ccccc67)c6ccc7oc8ccccc8c7c6)cc5)ccc4n(-c4ccccc4)c3cc21]

-continued
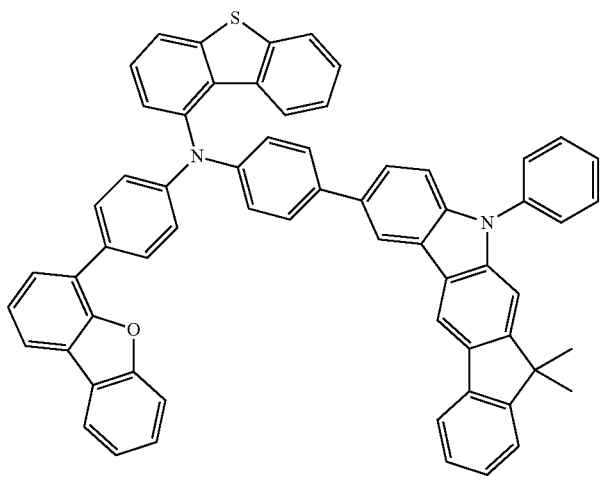 [SMILES: CC1(C)c2ccccc2-c2cc3c4cc(-c5ccc(N(c6ccc(-c7cccc8c7oc7ccccc78)cc6)c6cccc7sc8ccccc8c67)cc5)ccc4n(-c4ccccc4)c3cc21]
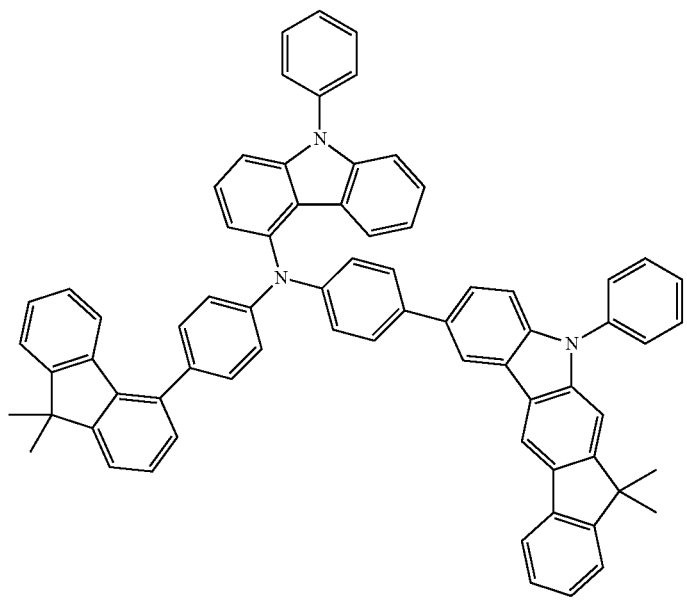 [SMILES: CC1(C)c2ccccc2-c2cc3c4cc(-c5ccc(N(c6ccc(-c7cccc8c7-c7ccccc7C8(C)C)cc6)c6cccc7c6c6ccccc6n7-c6ccccc6)cc5)ccc4n(-c4ccccc4)c3cc21]
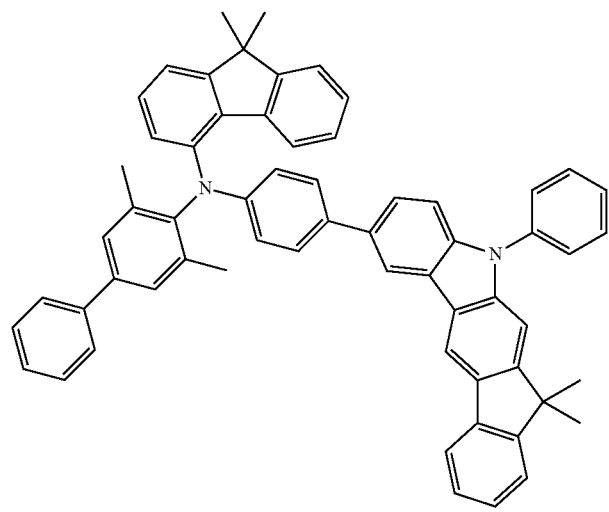 [SMILES: Cc1cc(-c2ccccc2)cc(C)c1N(c1ccc(-c2ccc3c(c2)c2cc4c(cc2n3-c2ccccc2)C(C)(C)c2ccccc2-4)cc1)c1cccc2c1-c1ccccc1C2(C)C]

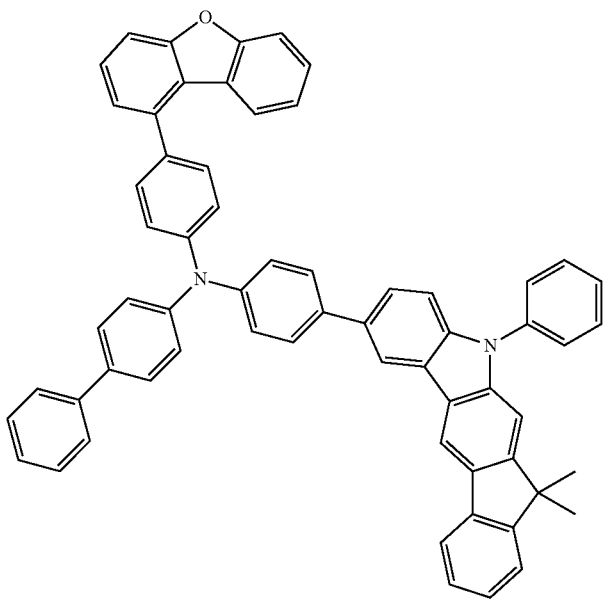 [SMILES: CC1(C)c2ccccc2-c2cc3c4cc(-c5ccc(N(c6ccc(-c7ccccc7)cc6)c6ccc(-c7cccc8oc9ccccc9c78)cc6)cc5)ccc4n(-c4ccccc4)c3cc21]
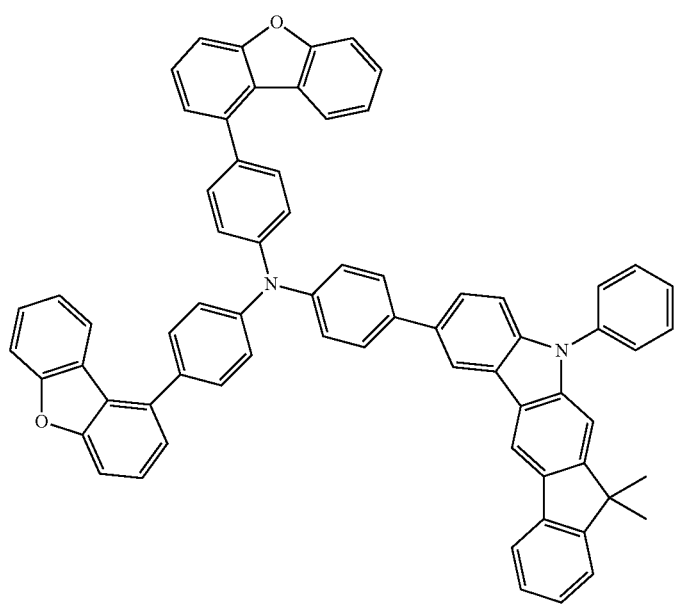 [SMILES: CC1(C)c2ccccc2-c2cc3c4cc(-c5ccc(N(c6ccc(-c7cccc8oc9ccccc9c78)cc6)c6ccc(-c7cccc8oc9ccccc9c78)cc6)cc5)ccc4n(-c4ccccc4)c3cc21]

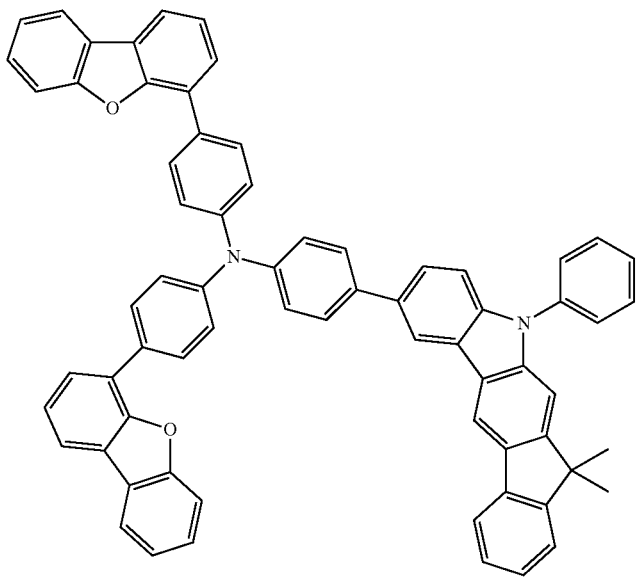 [SMILES: CC1(C)c2ccccc2-c2cc3c4cc(-c5ccc(N(c6ccc(-c7cccc8c7sc7ccccc78)cc6)c6ccc(-c7cccc8c7sc7ccccc78)cc6)cc5)ccc4n(-c4ccccc4)c3cc21]
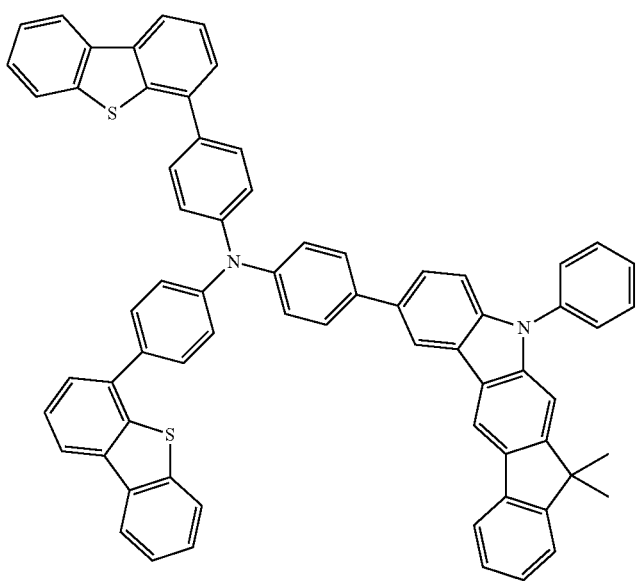

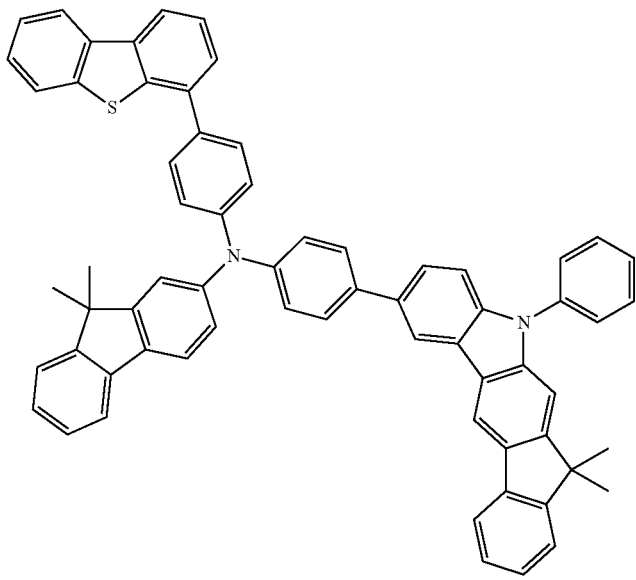 [SMILES: CC1(C)c2ccccc2-c2ccc(N(c3ccc(-c4ccc5c(c4)c4cc6c(cc4n5-c4ccccc4)C(C)(C)c4ccccc4-6)cc3)c3ccc(-c4cccc5c4sc4ccccc45)cc3)cc21]
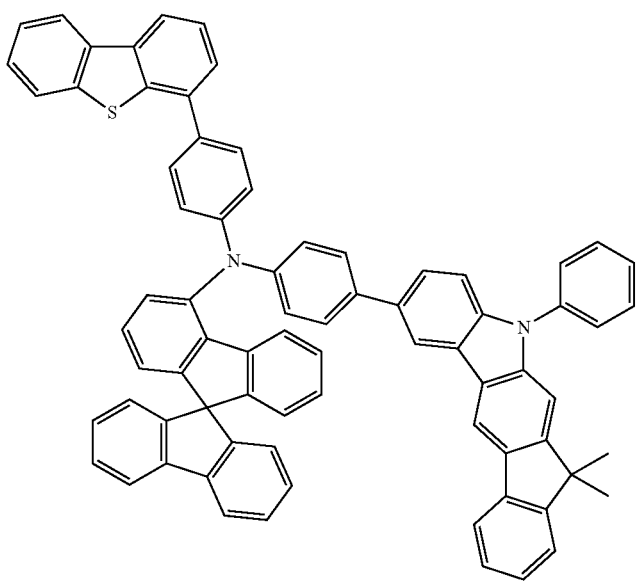 [SMILES: CC1(C)c2ccccc2-c2cc3c4cc(-c5ccc(N(c6ccc(-c7cccc8c7sc7ccccc78)cc6)c6cccc7c6-c6ccccc6C76c7ccccc7-c7ccccc76)cc5)ccc4n(-c4ccccc4)c3cc21]

-continued
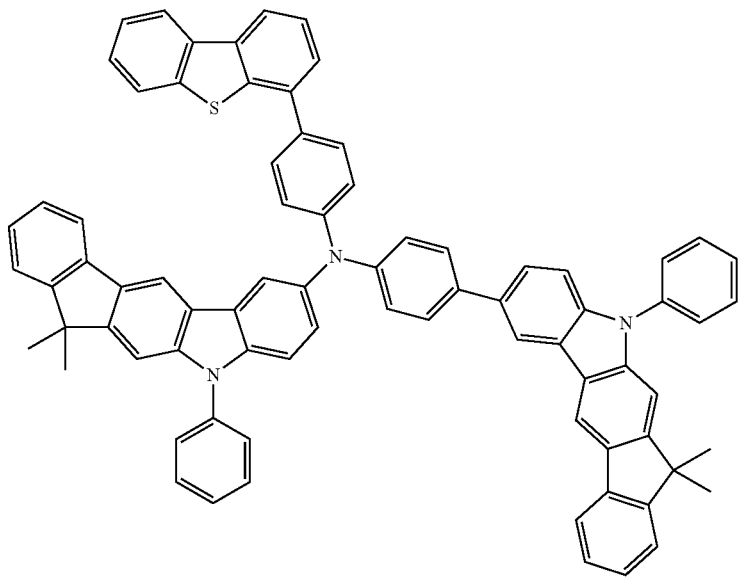 [SMILES: CC1(C)c2ccccc2-c2cc3c4cc(-c5ccc(N(c6ccc(-c7cccc8c7sc7ccccc78)cc6)c6ccc7c(c6)c6cc8c(cc6n7-c6ccccc6)C(C)(C)c6ccccc6-8)cc5)ccc4n(-c4ccccc4)c3cc21]
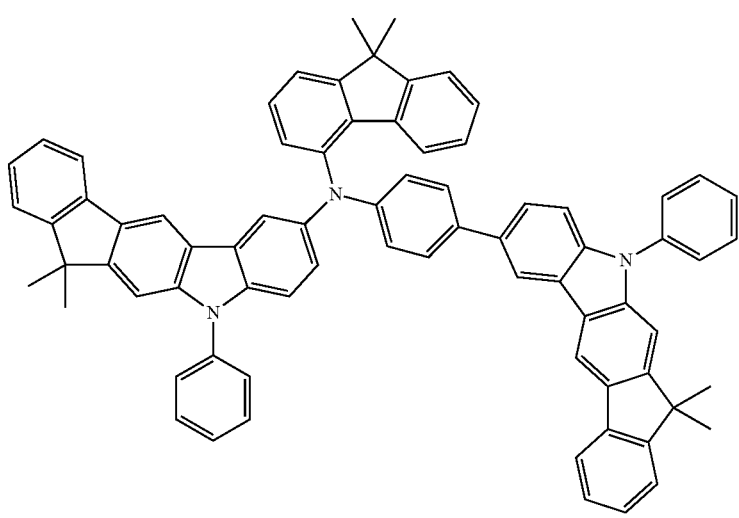 [SMILES: CC1(C)c2ccccc2-c2cc3c4cc(-c5ccc(N(c6ccc7c(c6)c6cc8c(cc6n7-c6ccccc6)C(C)(C)c6ccccc6-8)c6cccc7c6-c6ccccc6C7(C)C)cc5)ccc4n(-c4ccccc4)c3cc21]
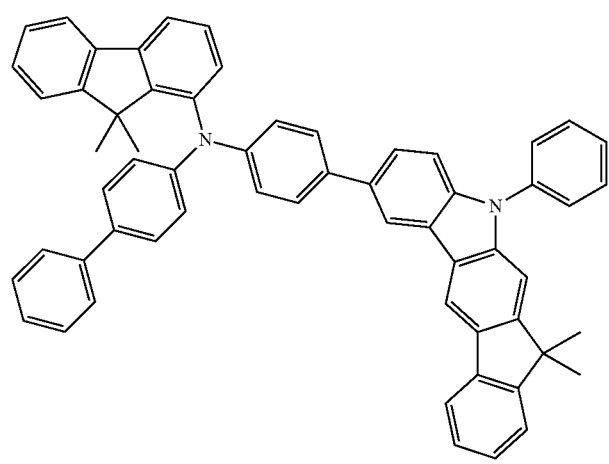 [SMILES: CC1(C)c2ccccc2-c2cc3c4cc(-c5ccc(N(c6ccc(-c7ccccc7)cc6)c6cccc7c6C(C)(C)c6ccccc6-7)cc5)ccc4n(-c4ccccc4)c3cc21]

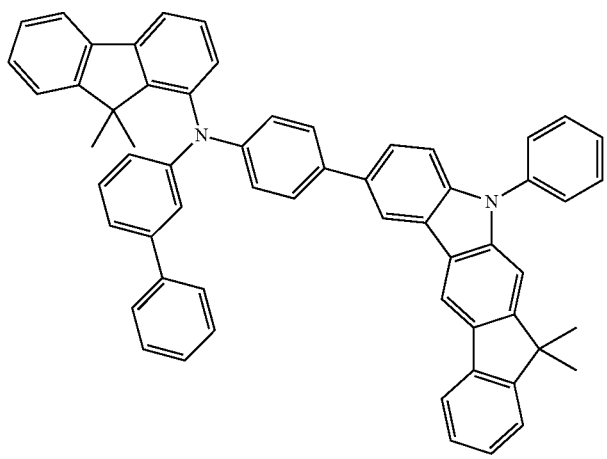 [SMILES: CC1(C)c2ccccc2-c2cc3c4cc(-c5ccc(N(c6cccc(-c7ccccc7)c6)c6cccc7c6C(C)(C)c6ccccc6-7)cc5)ccc4n(-c4ccccc4)c3cc21]
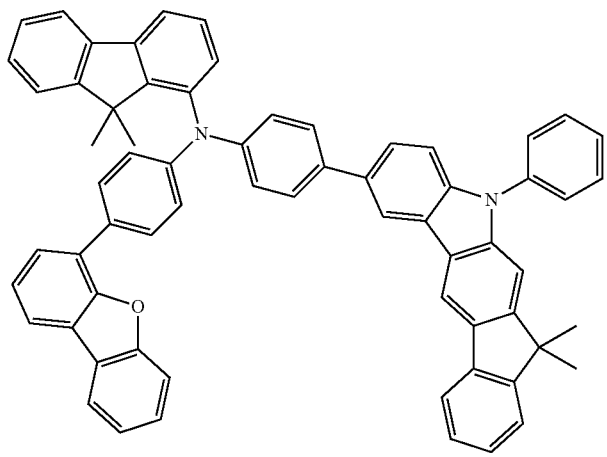
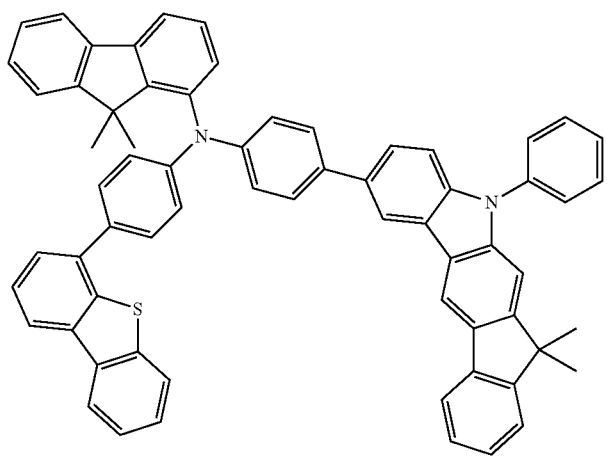 [SMILES: CC1(C)c2ccccc2-c2cc3c4cc(-c5ccc(N(c6ccc(-c7cccc8c7oc7ccccc78)cc6)c6cccc7c6C(C)(C)c6ccccc6-7)cc5)ccc4n(-c4ccccc4)c3cc21]

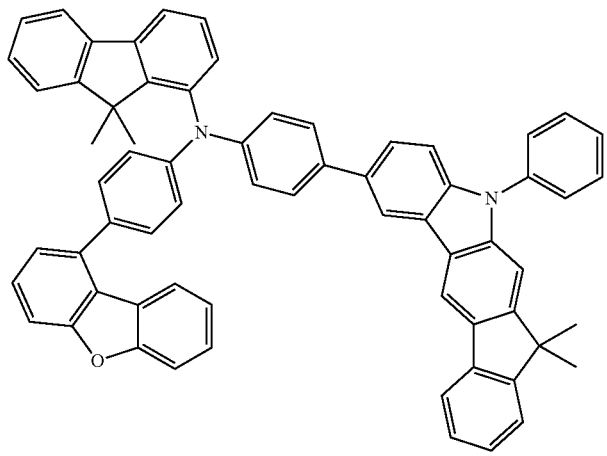 [SMILES: CC1(C)c2ccccc2-c2cc3c4cc(-c5ccc(N(c6ccc(-c7cccc8oc9ccccc9c78)cc6)c6cccc7c6C(C)(C)c6ccccc6-7)cc5)ccc4n(-c4ccccc4)c3cc21]
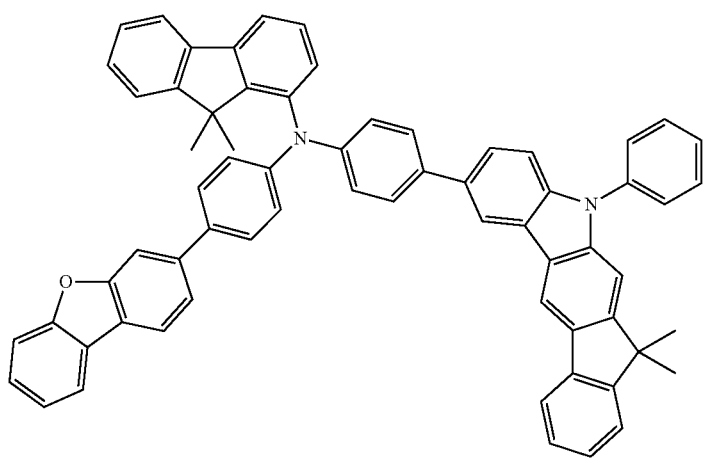 [SMILES: CC1(C)c2ccccc2-c2cc3c4cc(-c5ccc(N(c6ccc(-c7ccc8c(c7)oc7ccccc78)cc6)c6cccc7c6C(C)(C)c6ccccc6-7)cc5)ccc4n(-c4ccccc4)c3cc21]
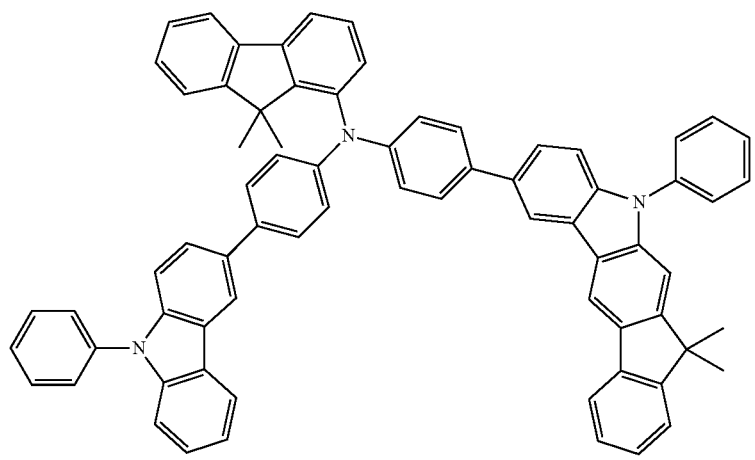 [SMILES: CC1(C)c2ccccc2-c2cc3c4cc(-c5ccc(N(c6ccc(-c7ccc8c(c7)c7ccccc7n8-c7ccccc7)cc6)c6cccc7c6C(C)(C)c6ccccc6-7)cc5)ccc4n(-c4ccccc4)c3cc21]

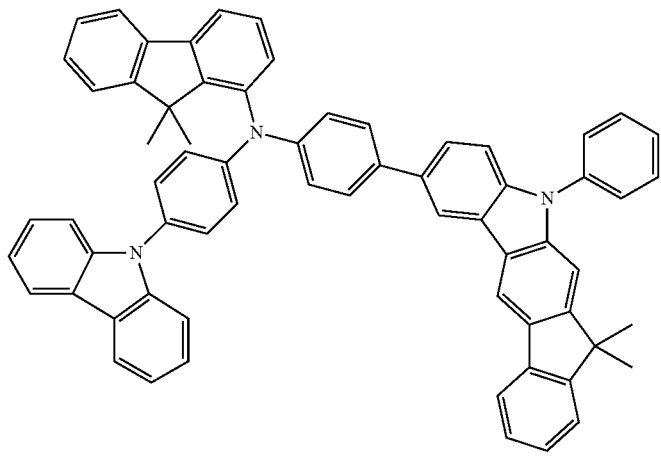 [SMILES: CC1(C)c2ccccc2-c2cc3c4cc(-c5ccc(N(c6ccc(-n7c8ccccc8c8ccccc87)cc6)c6cccc7c6C(C)(C)c6ccccc6-7)cc5)ccc4n(-c4ccccc4)c3cc21]
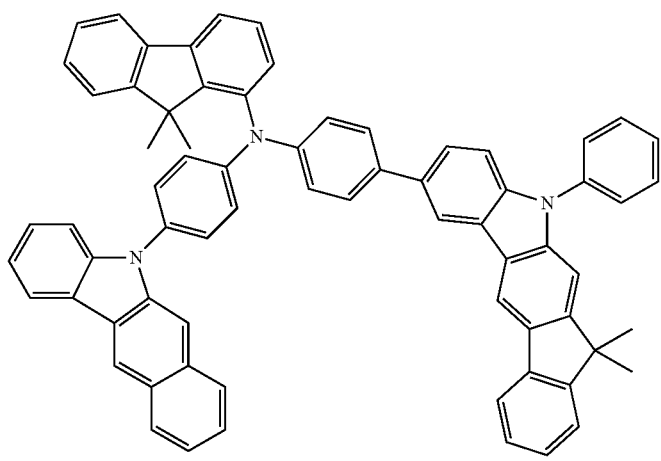 [SMILES: CC1(C)c2ccccc2-c2cc3c4cc(-c5ccc(N(c6ccc(-n7c8ccccc8c8cc9ccccc9cc87)cc6)c6cccc7c6C(C)(C)c6ccccc6-7)cc5)ccc4n(-c4ccccc4)c3cc21]
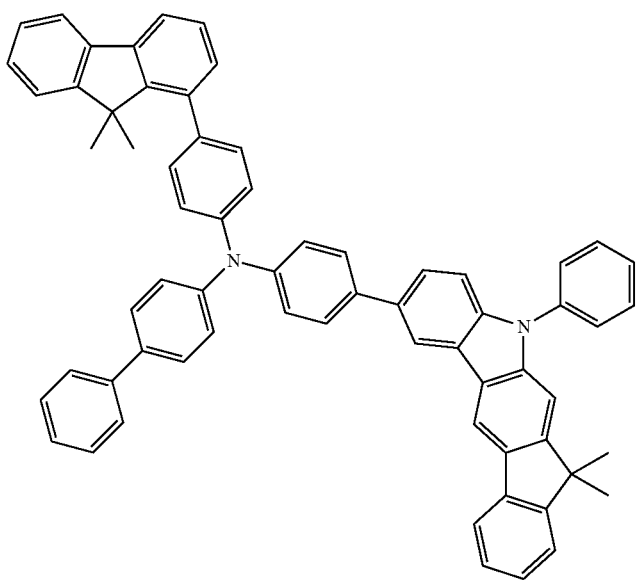 [SMILES: CC1(C)c2ccccc2-c2cc3c4cc(-c5ccc(N(c6ccc(-c7ccccc7)cc6)c6ccc(-c7cccc8c7C(C)(C)c7ccccc7-8)cc6)cc5)ccc4n(-c4ccccc4)c3cc21]

-continued
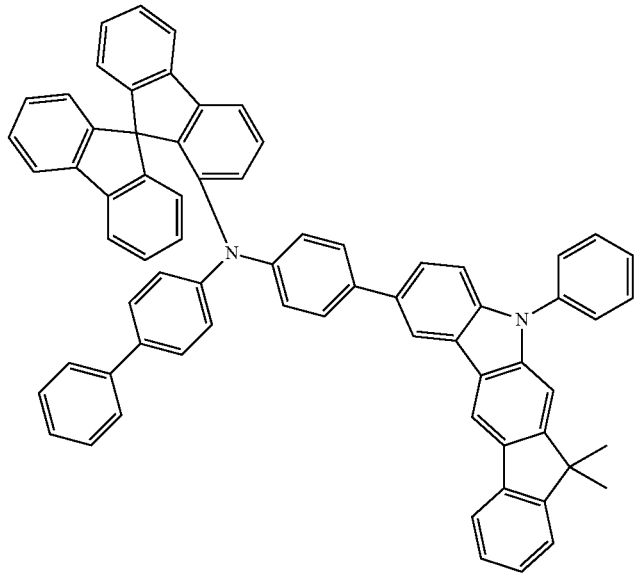 [SMILES: CC1(C)c2ccccc2-c2cc3c4cc(-c5ccc(N(c6ccc(-c7ccccc7)cc6)c6cccc7c6C6(c8ccccc8-c8ccccc86)c6ccccc6-7)cc5)ccc4n(-c4ccccc4)c3cc21]
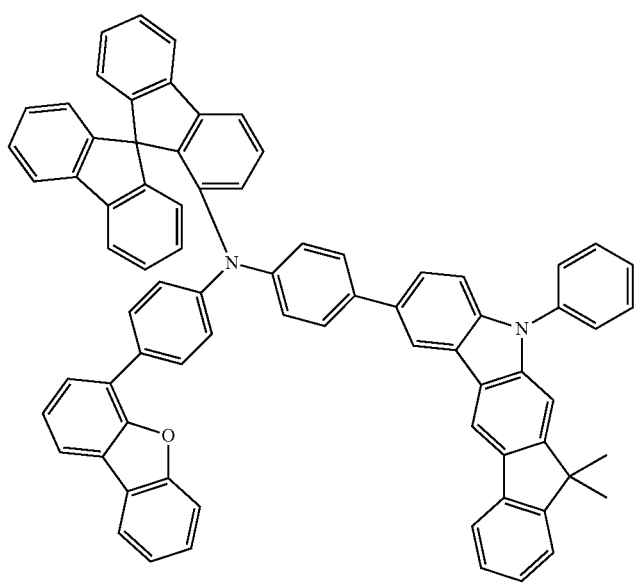 [SMILES: CC1(C)c2ccccc2-c2cc3c4cc(-c5ccc(N(c6ccc(-c7cccc8c7oc7ccccc78)cc6)c6cccc7c6C6(c8ccccc8-c8ccccc86)c6ccccc6-7)cc5)ccc4n(-c4ccccc4)c3cc21]

-continued
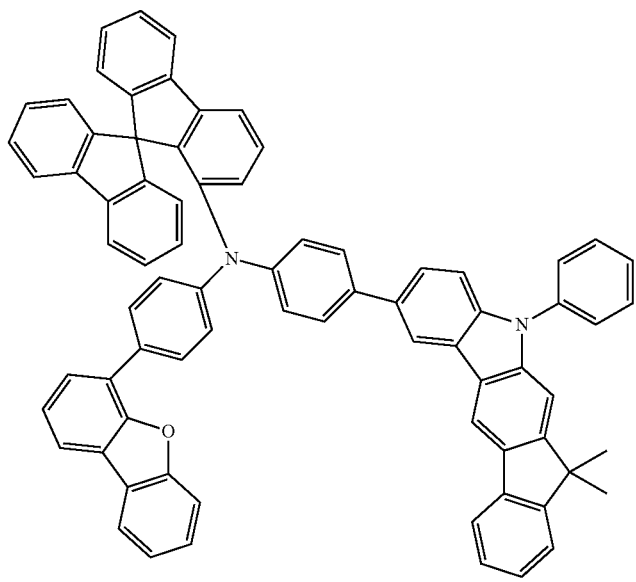 [SMILES: CC1(C)c2ccccc2-c2cc3c4cc(-c5ccc(N(c6ccc(-c7cccc8c7oc7ccccc78)cc6)c6cccc7c6C6(c8ccccc8-c8ccccc86)c6ccccc6-7)cc5)ccc4n(-c4ccccc4)c3cc21]
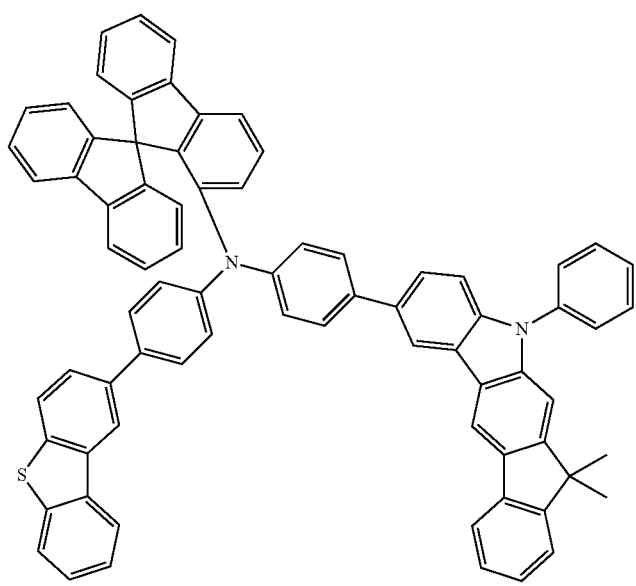 [SMILES: CC1(C)c2ccccc2-c2cc3c4cc(-c5ccc(N(c6ccc(-c7ccc8sc9ccccc9c8c7)cc6)c6cccc7c6C6(c8ccccc8-c8ccccc86)c6ccccc6-7)cc5)ccc4n(-c4ccccc4)c3cc21]

-continued
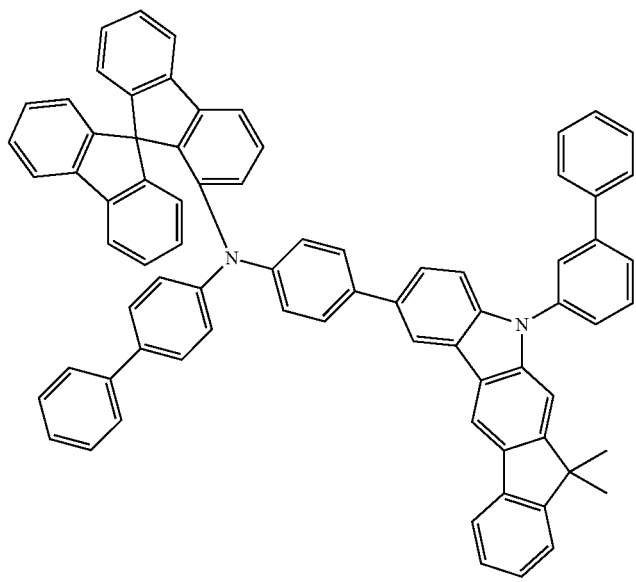 [SMILES: CC1(C)c2ccccc2-c2cc3c4cc(-c5ccc(N(c6ccc(-c7ccccc7)cc6)c6cccc7c6C6(c8ccccc8-c8ccccc86)c6ccccc6-7)cc5)ccc4n(-c4cccc(-c5ccccc5)c4)c3cc21]
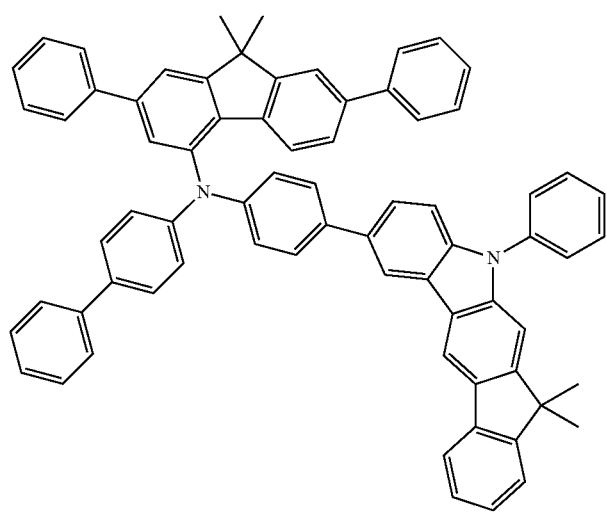 [SMILES: CC1(C)c2ccccc2-c2cc3c4cc(-c5ccc(N(c6ccc(-c7ccccc7)cc6)c6cc(-c7ccccc7)cc7c6-c6ccc(-c8ccccc8)cc6C7(C)C)cc5)ccc4n(-c4ccccc4)c3cc21]
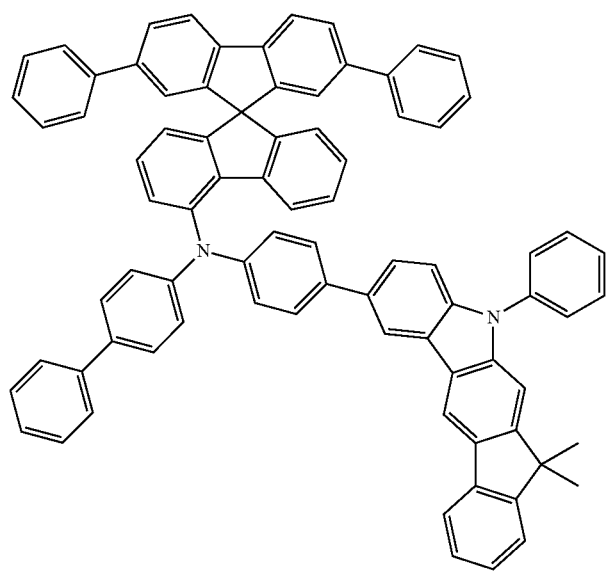 [SMILES: CC1(C)c2ccccc2-c2cc3c4cc(-c5ccc(N(c6ccc(-c7ccccc7)cc6)c6cccc7c6-c6ccccc6C76c7cc(-c8ccccc8)ccc7-c7ccc(-c8ccccc8)cc76)cc5)ccc4n(-c4ccccc4)c3cc21]

-continued
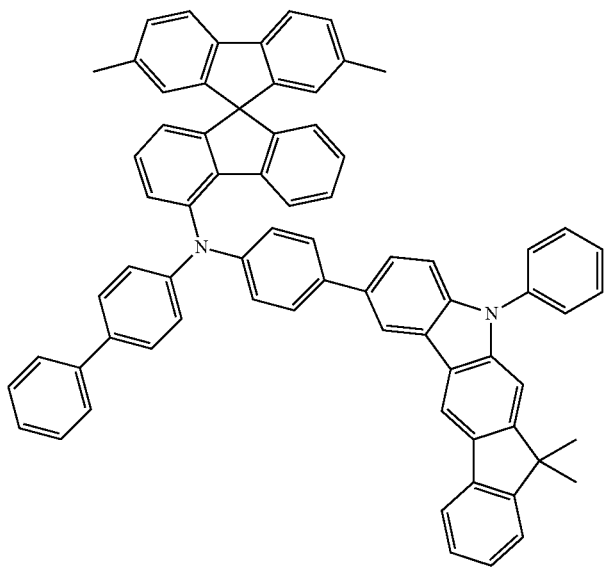 [SMILES: Cc1ccc2c(c1)C1(c3cc(C)ccc3-2)c2ccccc2-c2c(N(c3ccc(-c4ccccc4)cc3)c3ccc(-c4ccc5c(c4)c4cc6c(cc4n5-c4ccccc4)C(C)(C)c4ccccc4-6)cc3)cccc21]
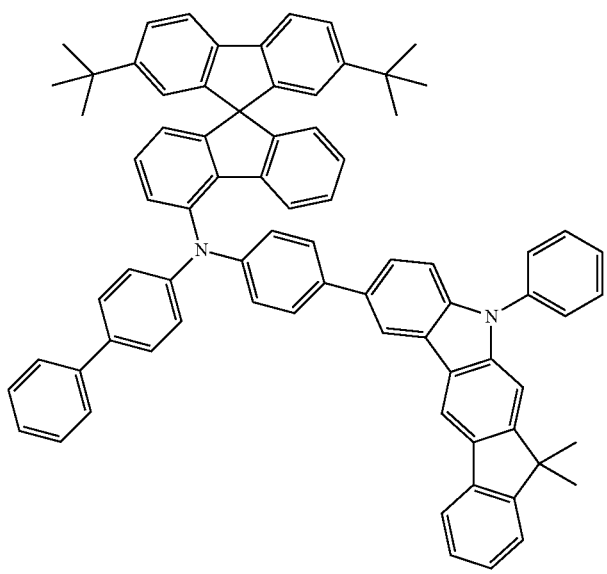 [SMILES: CC(C)(C)c1ccc2c(c1)C1(c3cc(C(C)(C)C)ccc3-2)c2ccccc2-c2c(N(c3ccc(-c4ccccc4)cc3)c3ccc(-c4ccc5c(c4)c4cc6c(cc4n5-c4ccccc4)C(C)(C)c4ccccc4-6)cc3)cccc21]

-continued
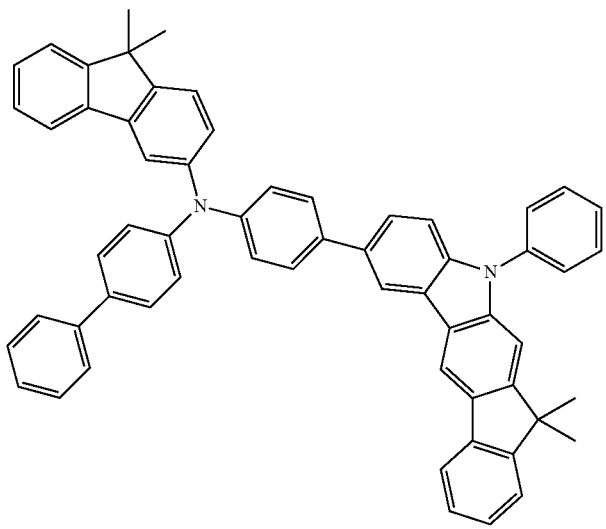 [SMILES: CC1(C)c2ccccc2-c2cc(N(c3ccc(-c4ccccc4)cc3)c3ccc(-c4ccc5c(c4)c4cc6c(cc4n5-c4ccccc4)C(C)(C)c4ccccc4-6)cc3)ccc21]
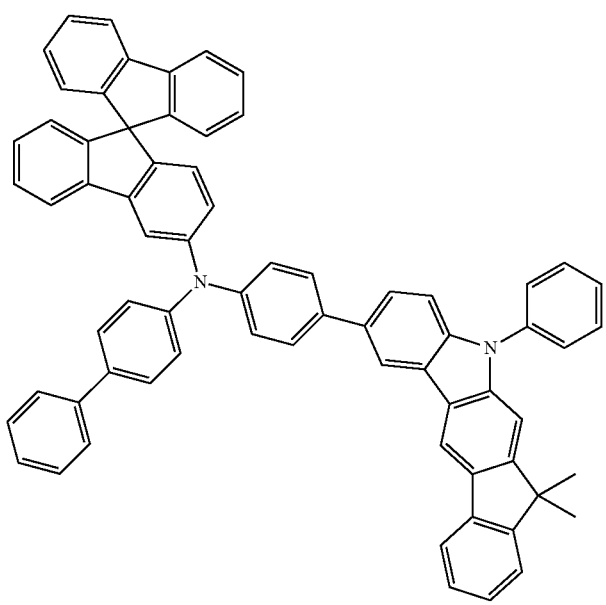 [SMILES: CC1(C)c2ccccc2-c2cc3c4cc(-c5ccc(N(c6ccc(-c7ccccc7)cc6)c6ccc7c(c6)-c6ccccc6C76c7ccccc7-c7ccccc76)cc5)ccc4n(-c4ccccc4)c3cc21]

-continued
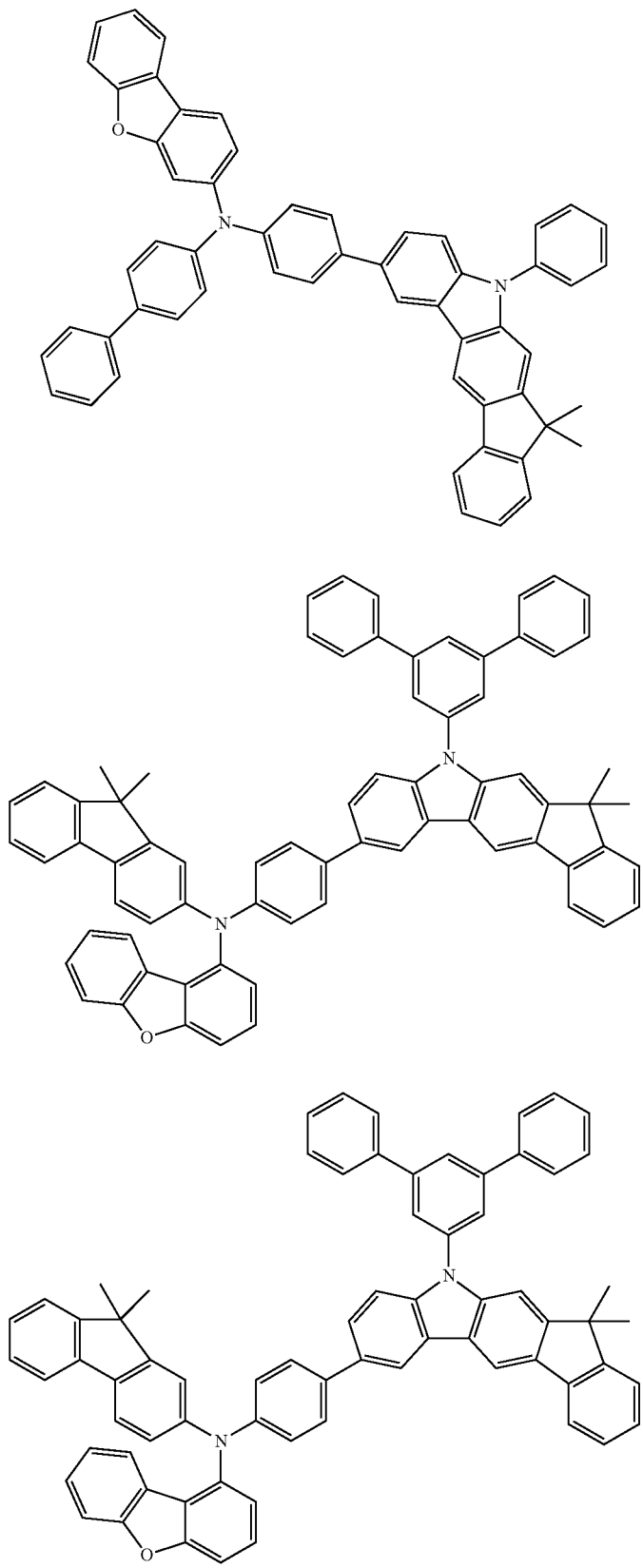

-continued
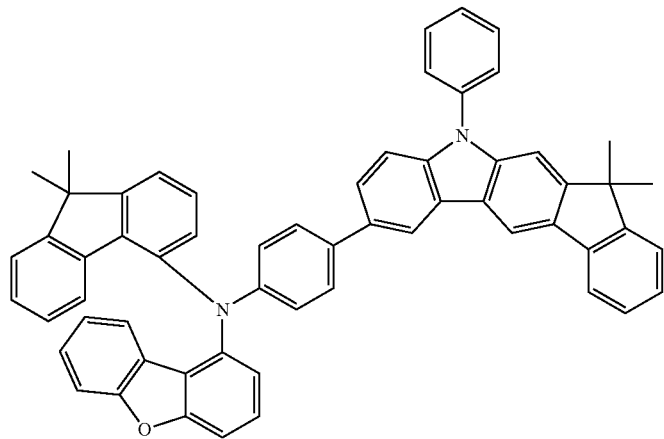
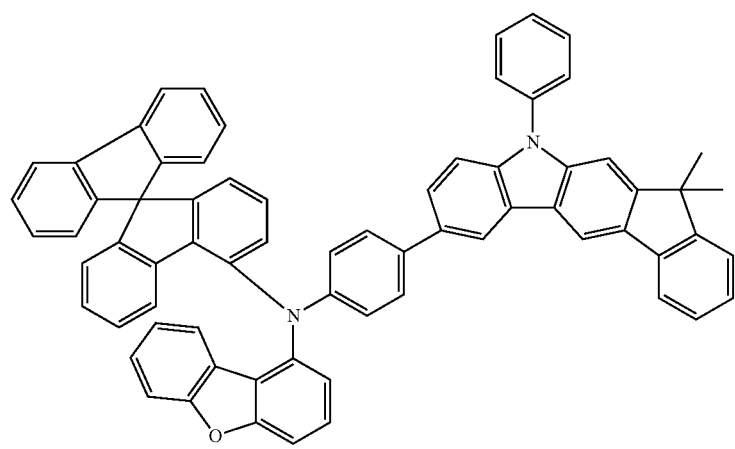 [SMILES: CC1(C)c2ccccc2-c2cc3c4cc(-c5ccc(N(c6cccc7c6-c6ccccc6C76c7ccccc7-c7ccccc76)c6cccc7oc8ccccc8c67)cc5)ccc4n(-c4ccccc4)c3cc21]
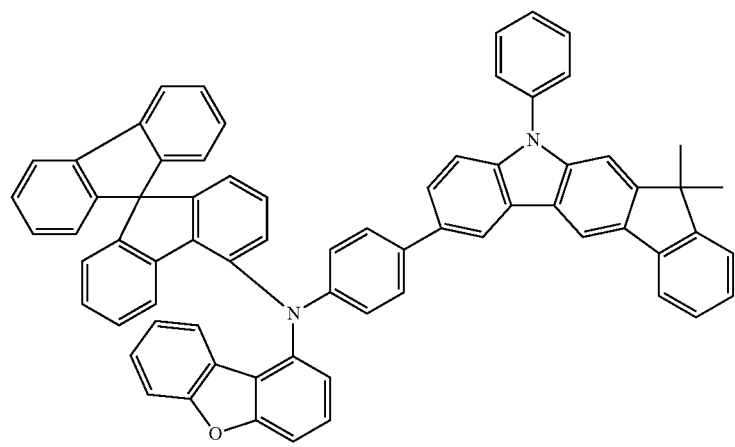 [SMILES: CC1(C)c2ccccc2-c2cc3c4cc(-c5ccc(N(c6cccc7c6-c6ccccc6C76c7ccccc7-c7ccccc76)c6cccc7oc8ccccc8c67)cc5)ccc4n(-c4ccccc4)c3cc21]

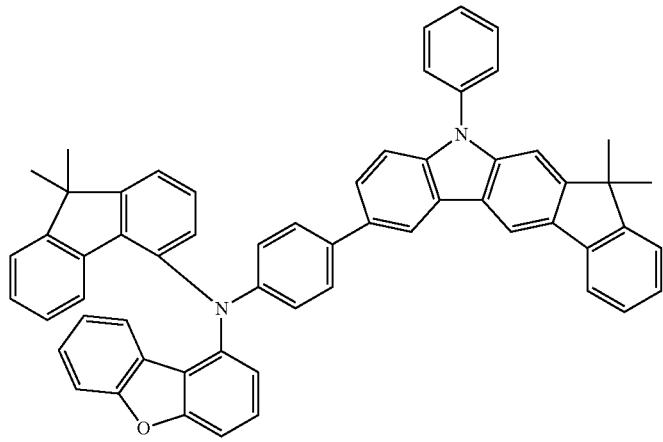 [SMILES: CC1(C)c2ccccc2-c2cc3c4cc(-c5ccc(N(c6cccc7c6-c6ccccc6C7(C)C)c6cccc7oc8ccccc8c67)cc5)ccc4n(-c4ccccc4)c3cc21]
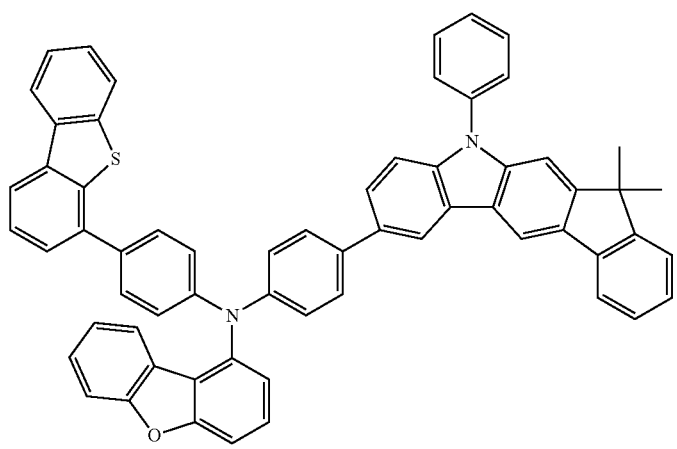 [SMILES: CC1(C)c2ccccc2-c2cc3c4cc(-c5ccc(N(c6ccc(-c7cccc8c7sc7ccccc78)cc6)c6cccc7oc8ccccc8c67)cc5)ccc4n(-c4ccccc4)c3cc21]
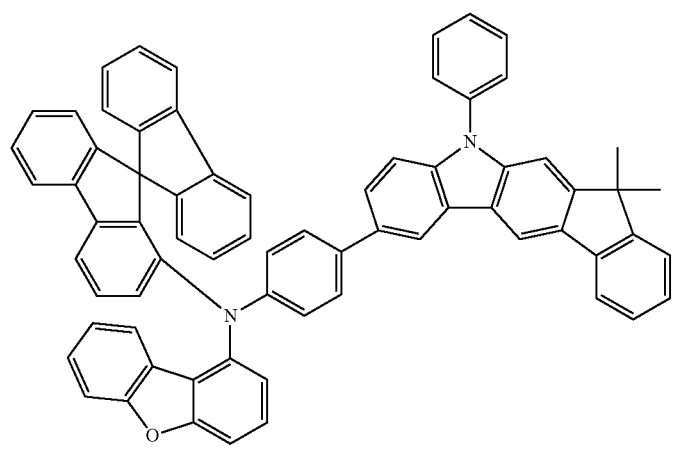 [SMILES: CC1(C)c2ccccc2-c2cc3c4cc(-c5ccc(N(c6cccc7c6C6(c8ccccc8-c8ccccc86)c6ccccc6-7)c6cccc7oc8ccccc8c67)cc5)ccc4n(-c4ccccc4)c3cc21]

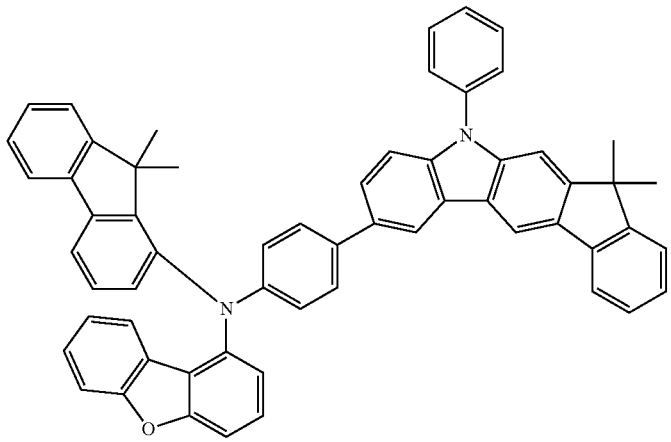 [SMILES: CC1(C)c2ccccc2-c2cc3c4cc(-c5ccc(N(c6cccc7c6C(C)(C)c6ccccc6-7)c6cccc7oc8ccccc8c67)cc5)ccc4n(-c4ccccc4)c3cc21]
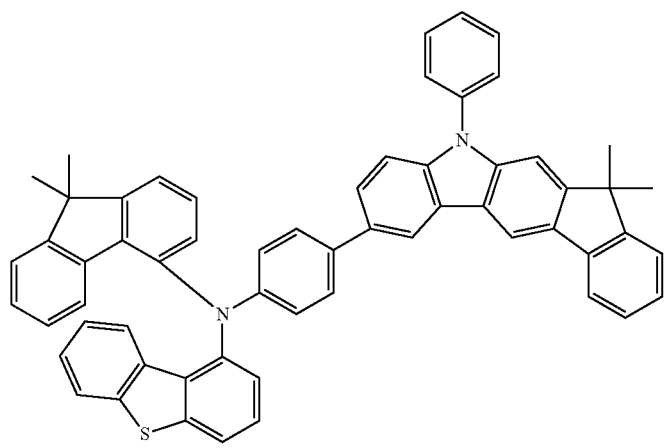
The compounds of the invention can be synthesized by the route outlined in general terms in the following scheme and described hereinafter:
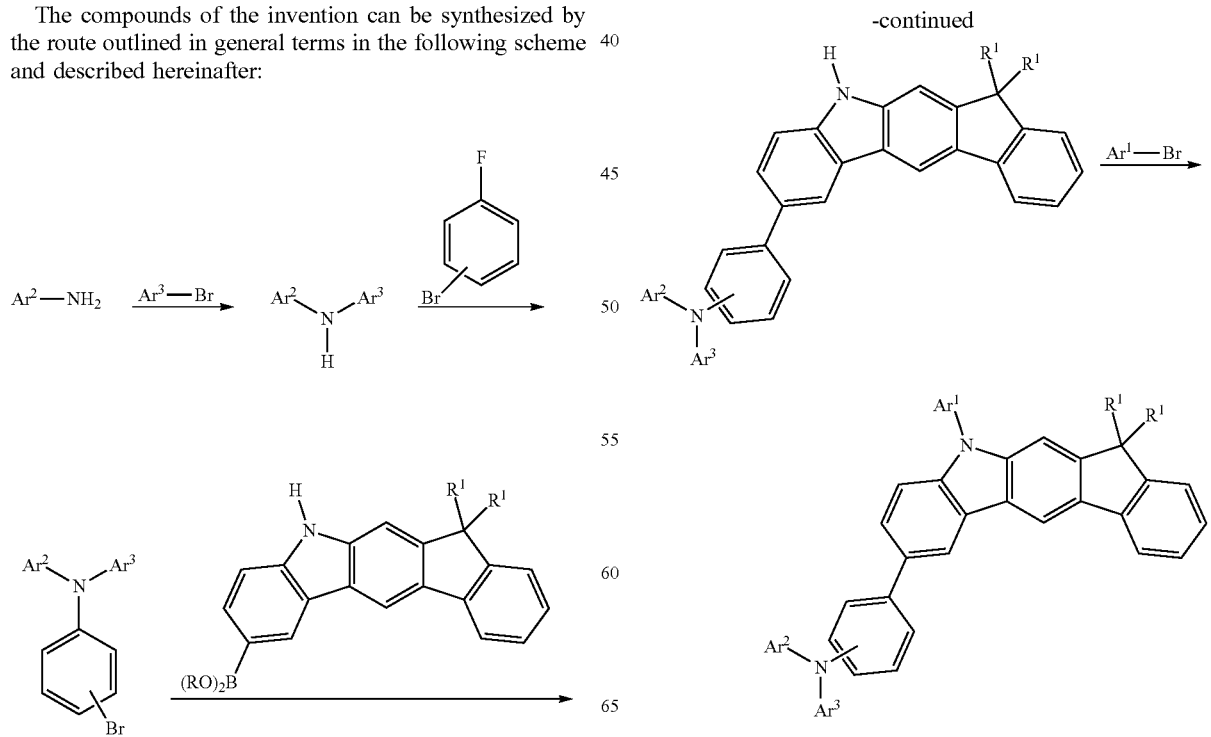

A primary amine Ar²—NH₂ is coupled in a C—N coupling reaction, for example a Hartwig-Buchwald coupling, with an aryl group Ar³ bearing a reactive leaving group. There follows reaction with a fluorine-substituted benzene bearing a further reactive leaving group, followed by a C-C coupling reaction, for example a Suzuki coupling, to the indenocarbazole. In the last step, the Ar¹ group in the indenocarbazole is introduced by a C—N coupling reaction, for example a Hartwig-Buchwald coupling, with an aryl group Ar¹ bearing a reactive leaving group. Suitable reactive leaving groups in the above-described reactions are, for example, bromine, iodine or tosylate. In addition, for synthesis of correspondingly substituted compounds, it is possible to use the correspondingly substituted reactants.

The present invention therefore further provides a process for synthesis of the compounds of the invention, comprising a coupling reaction between the Ar²Ar³N-phenylene unit substituted by a reactive leaving group, and an indenocarbazole substituted by a reactive leaving group.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, hexamethylindane, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound and/or a further matrix material. Suitable emitting compounds and further matrix materials are listed at the back in connection with the organic electroluminescent device. This further compound may also be polymeric.

The compounds of the invention are suitable for use in an electronic device, especially in an organic electroluminescent device.

The present invention therefore further provides for the use of a compound of the invention in an electronic device, especially in an organic electroluminescent device.

The present invention still further provides an electronic device comprising at least one compound of the invention.

An electronic device in the context of the present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitized organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), more preferably phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction, see, for example, WO 2005/011013). The organic electroluminescent device of the invention may also be a tandem OLED, especially also for white-emitting OLEDs.

The compound of the invention according to the above-detailed embodiments may be used in different layers, according to the exact structure. Preference is given to an organic electroluminescent device comprising a compound of formula (1) or the preferred embodiments detailed above as matrix material for phosphorescent emitters in an emitting layer. In this case, the organic electroluminescent device may contain an emitting layer, or it may contain a plurality of emitting layers, where at least one emitting layer contains at least one compound of the invention as matrix material. Preference is further given to an organic electroluminescent device comprising a compound of formula (1) or the preferred embodiments detailed above as electron blocker material in an electron blocker layer or as hole transport material in a hole transport or hole injection layer.

When the compound of the invention is used as matrix material for a phosphorescent compound in an emitting layer, it is preferably used in combination with one or more phosphorescent materials (triplet emitters). Phosphorescence in the context of this invention is understood to mean luminescence from an excited state having higher spin multiplicity, i.e. a spin state>1, especially from an excited triplet state. In the context of this application, all luminescent complexes with transition metals or lanthanides, especially all iridium, platinum and copper complexes, shall be regarded as phosphorescent compounds.

The mixture of the compound of the invention and the emitting compound contains between 99% and 1% by volume, preferably between 98% and 10% by volume, more preferably between 97% and 60% by volume and especially between 95% and 80% by volume of the compound of the invention, based on the overall mixture of emitter and matrix material. Correspondingly, the mixture contains between 1% and 99% by volume, preferably between 2% and 90% by volume, more preferably between 3% and 40% by volume and especially between 5% and 30% by volume of the emitter, based on the overall mixture of emitter and matrix material.

A further preferred embodiment of the present invention is the use of the compound of the invention as matrix material for a phosphorescent emitter in combination with a further matrix material. When the compound of the invention is used in combination with a further matrix material, the proportion thereof is preferably 20% to 50% by volume, based on the overall mixture. The further matrix material is preferably an electron-transporting material. Suitable matrix materials which can be used in combination with the inventive compounds are aromatic ketones, aromatic phosphine oxides or aromatic sulphoxides or sulphones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or WO 2013/041176, indolocarbazole derivatives, for example according to WO 2007/063754 or WO 2008/056746, indenocarbazole derivatives, for example according to WO 2010/136109, WO 2011/000455, WO 2013/041176 or WO 2013/056776, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 2001/41512, WO 2002/02714, WO 2002/15645, EP 1191613, EP 1191612, EP 1191614, WO 2005/033244, WO 2005/019373, US 2005/0258742, WO 2010/086089, WO 2011/044988, WO 2011/157339, WO 2012/007086, WO 2012/163471, WO 2013/000531 and WO 2013/020631, WO 2014/008982, WO 2014/023377, WO 2014/094962, WO 2014/094961, WO 2014/094960, WO 2015/039723, WO 2015/104045, WO 2015/117718 and WO 2016/015815. Additionally suitable are, for example, the metal complexes disclosed in the unpublished application EP 15000307.7. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

The compounds of the invention are especially also suitable as matrix materials for phosphorescent emitters in organic electroluminescent devices, as described, for example, in WO 98/24271, US 2011/0248247 and US 2012/0223633. In these multicolour display components, an additional blue emission layer is applied by vapour deposition over the full area to all pixels, including those having a colour other than blue.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In the further layers of the organic electroluminescent device of the invention, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than 10–6 mbar. It is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition.

These methods are known in general terms to those skilled in the art and can be applied by those skilled in the art without exercising inventive skill to organic electroluminescent devices comprising the compounds of the invention.

The compounds of the invention, used in OLEDs as matrix material for phosphorescent emitters or as electron blocker material in an electron blocker layer, lead to improved lifetimes compared to the analogous matrix materials according to the prior art which, rather than a group of the formula (2), contain a different aromatic ring system. These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further compounds of the invention without exercising inventive skill and to use them in electronic devices or to employ the process of the invention.

EXAMPLES

Synthesis Examples

The syntheses which follow, unless stated otherwise, are conducted under a protective gas atmosphere in dried solvents. The solvents and reagents can be purchased from ALDRICH or ABCR. The numbers given for the reactants that are not commercially available are the corresponding CAS numbers.

The synthesis of the compounds of the invention is specified by way of example for an example structure in the scheme which follows. Derivatives having other $Ar^1$, $Ar^2$, $Ar^2$, R and $R^1$ groups are synthesized correspondingly.

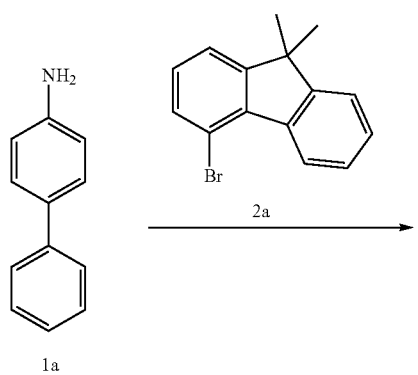

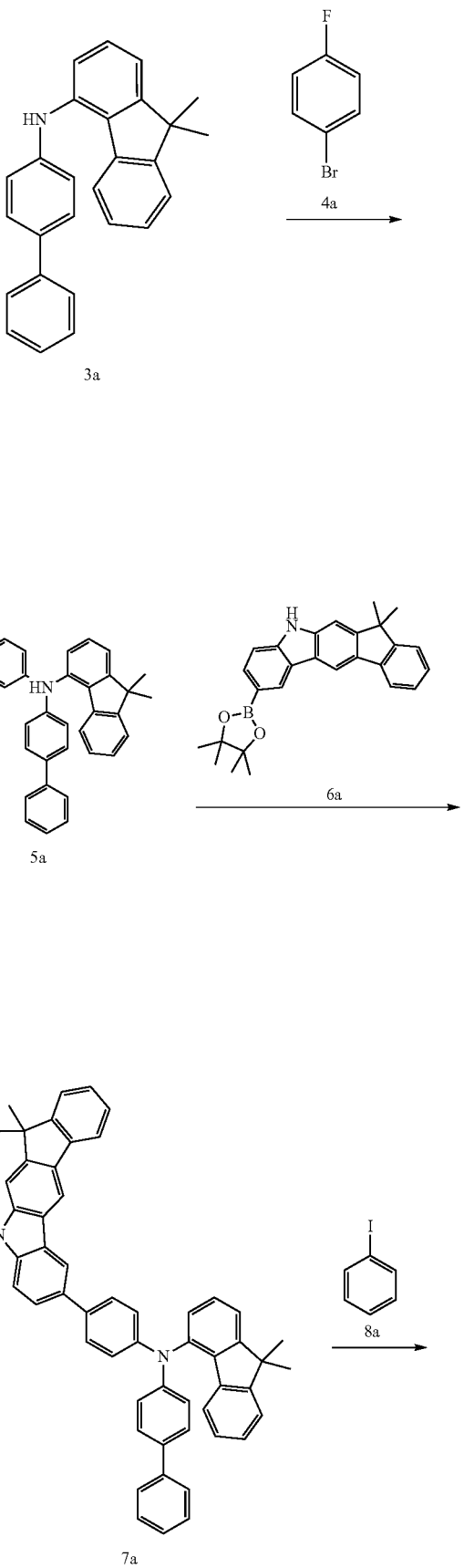

-continued

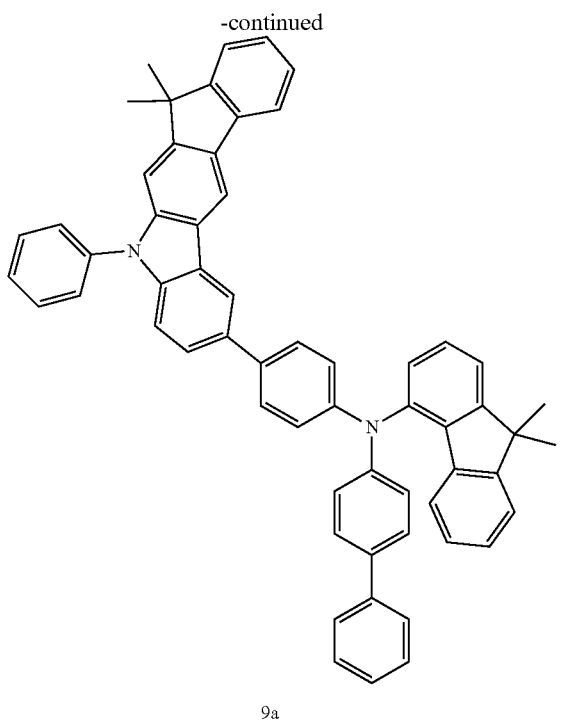

9a

Stage 1: Preparation of biphenyl-4-yl(9,9-dimethyl-9H-fluoren-4-yl)amine 3a

In a 2 l four-neck flask, 30.0 g (177 mmol, 1.0 eq) of 4-aminobiphenyl [92-67-1] 1a are initially charged together with 48.4 g (177 mmol, 1.0 eq) of 4-bromo-9,9-dimethyl-9H-fluorene [942615-32-9] 2a and 23.4 g (212 mmol, 1.20 eq) of sodium t-pentoxide [14593-46-5] in 600 ml of absolute toluene and degassed for 30 minutes. Subsequently, 398 mg (1.77 mmol, 0.01 eq) of palladium(II) acetate [3375-31-3] and 1.46 g (3.56 mmol, 0.02 eq) of 2-dicyclohexylphosphino-2',6'-dimethoxybiphenyl SPHOS [657408-07-6] are added and the mixture is heated under reflux overnight. After the reaction has ended, the mixture is cooled down to room temperature and extracted with 500 ml of water. Subsequently, the aqueous phase is washed three times with toluene, the combined organic phases are dried over sodium sulphate and the solvent is removed on a rotary evaporator. The brown residue is taken up in about 200 ml of toluene and filtered through silica gel. For further purification, a recrystallization from toluene/heptane is conducted. 51.3 g (142 mmol, 80%) of the amine 3a are obtained.

The following are prepared analogously:

-continued

| | Reactant 1 | Reactant 2 | Product 3 | Yield [%] |
|---|---|---|---|---|
| 3d | H₂N-biphenyl [92-67-1] | 4-bromodibenzothiophene [97511-05-2] | N-([1,1'-biphenyl]-4-yl)dibenzothiophen-4-amine | 68 |
| 3e | H₂N-biphenyl [92-67-1] | 4-bromo-6-phenyldibenzothiophene [1415844-67-5] | N-([1,1'-biphenyl]-4-yl)-6-phenyldibenzothiophen-4-amine | 34 |
| 3f | H₂N-biphenyl [92-67-1] | 4-(4-bromophenyl)dibenzofuran [1225053-54-2] | N-([1,1'-biphenyl]-4-yl)-4-(dibenzofuran-4-yl)aniline | 78 |
| 3g | H₂N-biphenyl [92-67-1] | 2-bromodibenzofuran [86-76-0] | N-([1,1'-biphenyl]-4-yl)dibenzofuran-2-amine | 51 |

-continued

| | Reactant 1 | Reactant 2 | Product 3 | Yield [%] |
|---|---|---|---|---|
| 3h | H₂N-biphenyl [92-67-1] | 1-bromodibenzofuran [50548-45-3] | N-(biphenyl-4-yl)dibenzofuran-1-amine | 65 |
| 3i | H₂N-biphenyl [92-67-1] | 4-bromobenzo[b]naphtho-furan [1642127-11-4] | N-(biphenyl-4-yl)benzo[b]naphthofuran-4-amine | 81 |
| 3j | H₂N-biphenyl [92-67-1] | 3-bromo-9,9-dimethylfluorene [1190360-23-6] | N-(biphenyl-4-yl)-9,9-dimethyl-9H-fluoren-3-amine | 33 |
| 3k | H₂N-biphenyl [92-67-1] | 3-bromo-9,9'-spirobifluorene [1361227-58-8] | N-(biphenyl-4-yl)-9,9'-spirobifluoren-3-amine | 63 |

-continued
| | Reactant 1 | Reactant 2 | Product 3 | Yield [%] |
|---|---|---|---|---|
| 3l | 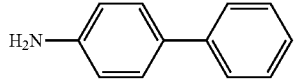 [SMILES: Nc1ccc(-c2ccccc2)cc1]<br>[92-67-1] | 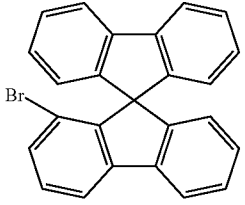 [SMILES: Brc1cccc2c1C1(c3ccccc3-c3ccccc31)c1ccccc1-2]<br>[1450933-18-2] | 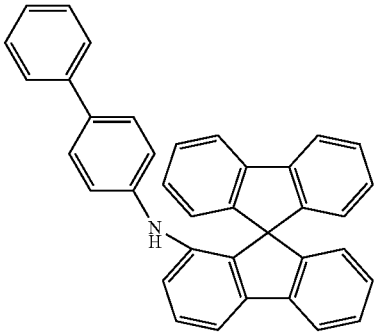 [SMILES: c1ccc(-c2ccc(Nc3cccc4c3C3(c5ccccc5-c5ccccc53)c3ccccc3-4)cc2)cc1] | 23 |
| 3m | 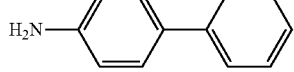<br>[92-67-1] | 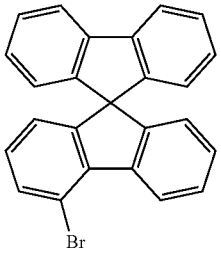 [SMILES: Brc1cccc2c1-c1ccccc1C21c2ccccc2-c2ccccc21]<br>[1161009-88-6] | 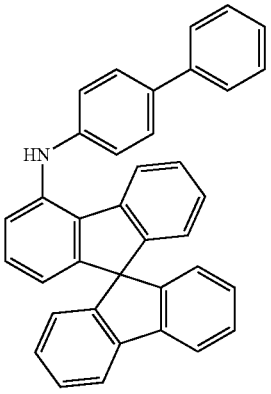 [SMILES: c1ccc(-c2ccc(Nc3cccc4c3-c3ccccc3C43c4ccccc4-c4ccccc43)cc2)cc1] | 55 |
| 3n | 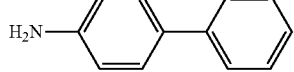<br>[92-67-1] | 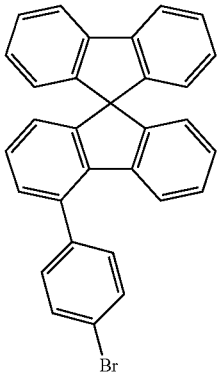 [SMILES: Brc1ccc(-c2cccc3c2-c2ccccc2C32c3ccccc3-c3ccccc32)cc1]<br>[1421789-08-3] | 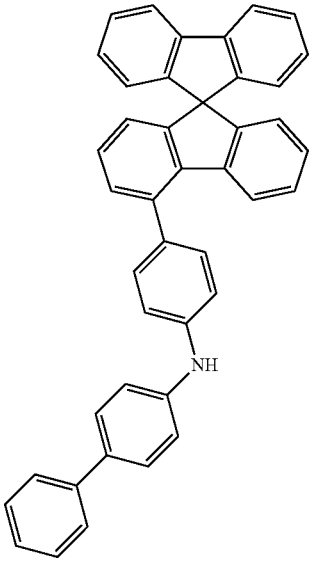 [SMILES: c1ccc(-c2ccc(Nc3ccc(-c4cccc5c4-c4ccccc4C54c5ccccc5-c5ccccc54)cc3)cc2)cc1] | 68 |

-continued
| | Reactant 1 | Reactant 2 | Product 3 | Yield [%] |
|---|---|---|---|---|
| 3o | 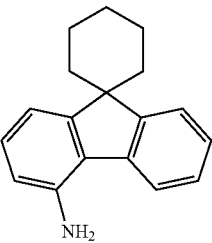 [SMILES: Nc1cccc2c1-c1ccccc1C21CCCCC1] [18998-24-8] | 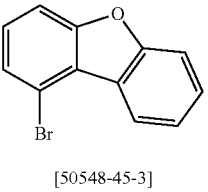 [50548-45-3] | 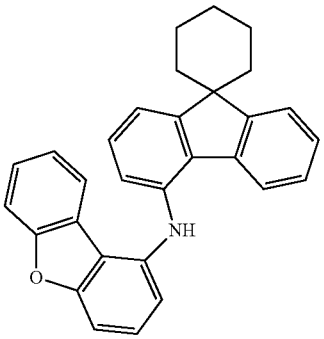 [SMILES: c1ccc2c(c1)-c1c(Nc3cccc4oc5ccccc5c34)cccc1C21CCCCC1] | 43 |
| 3p | 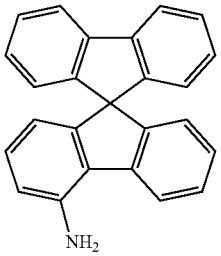 [SMILES: Nc1cccc2c1-c1ccccc1C21c2ccccc2-c2ccccc21] [1579281-06-3] | 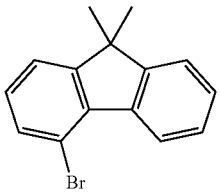 [SMILES: CC1(C)c2ccccc2-c2c(Br)cccc21] [942615-32-9] | 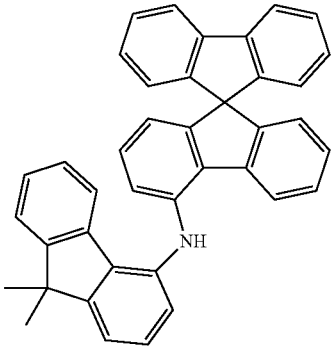 [SMILES: CC1(C)c2ccccc2-c2c(Nc3cccc4c3-c3ccccc3C43c4ccccc4-c4ccccc43)cccc21] | 29 |
| 3q | 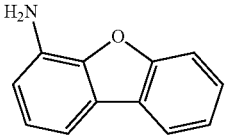 [SMILES: Nc1cccc2c1oc1ccccc12] [50548-43-1] | 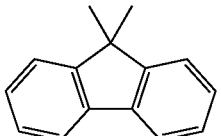 [942615-32-9] | 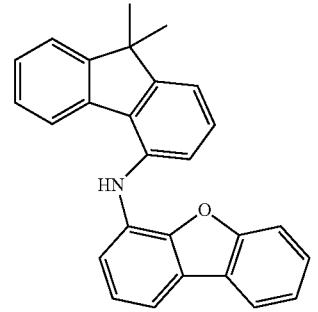 [SMILES: CC1(C)c2ccccc2-c2c(Nc3cccc4c3oc3ccccc34)cccc21] | 34 |
| 3r | 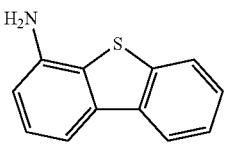 [72433-66-0] | 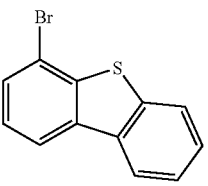 [SMILES: Brc1cccc2c1sc1ccccc12] [97511-05-2] | 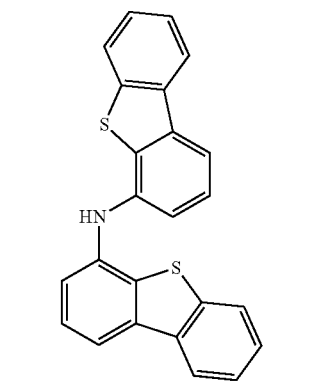 [SMILES: c1ccc2c(c1)sc1c(Nc3cccc4c3sc3ccccc34)cccc12] | 55 |

-continued

| | Reactant 1 | Reactant 2 | Product 3 | Yield [%] |
|---|---|---|---|---|
| 3s | [578027-21-1] | [942615-32-9] | | 62 |
| 3t | [578027-21-1] | [1225053-54-2] | | 72 |
| 3u | [50548-43-1] | [1161009-88-6] | | 45 |

Stage 2: Preparation of (4-bromophenyl)-(9,9-dimethyl-9H-fluoren-4-yl)-{4-[(E)-((Z)-1-propenyl)buta-1,3-dienyl]phenyl}amine 5a In a 1 l four-neck flask, 51.3 g (142 mmol, 1.00 eq) of the amine 3a and also 75.6 g (426 mmol, 3.00 eq) of 1-bromo-4-fluorobenzene [460-00-4] 4a and 92.5 g (284 mmol, 2.00 eq) of caesium carbonate [534-17-8] are initially charged, and 500 ml of dimethylacetamide are added. The reaction mixture is stirred at 150° C. for three days. After the reaction has ended, the mixture is cooled down to room temperature and the solids are filtered off through Celite. The mother liquor is concentrated and the precipitated solids, after filtration, are extracted by stirring with hot methanol. After drying, 43.5 g (135 mmol, 95%) of the colourless product 5a are obtained.

The following are prepared analogously:

| | Reactant 3 | Product 5 | Yield [%] |
|---|---|---|---|
| 5b | | | 78 |
| 5c | | | 81 |
| 5d | | | 94 |
| 5e | | | 92 |

-continued

| Reactant 3 | Product 5 | Yield [%] |
|---|---|---|
| 5f | | 71 |
| 5g | | 88 |
| 5h | | 65 |
| 5i | | 79 |

-continued

| Reactant 3 | Product 5 | Yield [%] |
|---|---|---|
| 5j | | 36 |
| 5k | | 91 |
| 5l | | 26 |
| 5m | | 84 |

-continued
| | Reactant 3 | Product 5 | Yield [%] |
|---|---|---|---|
| 5n | 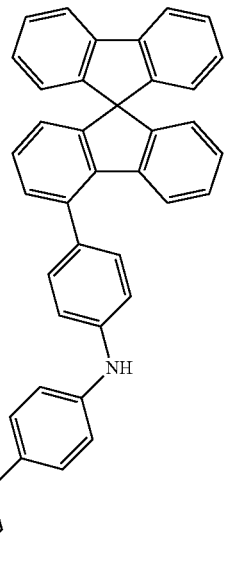 | 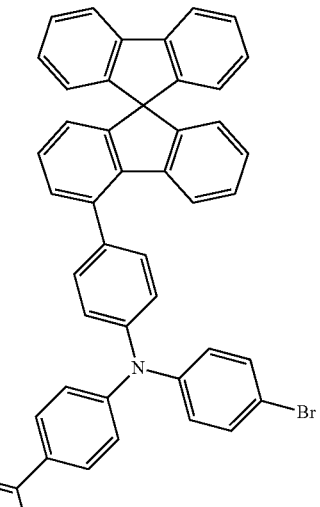 | 68 |
| 5o | 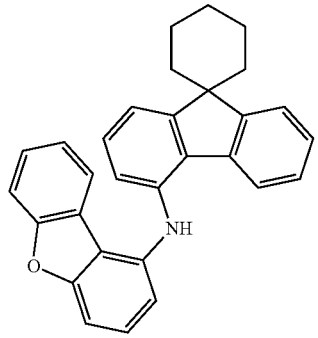 [SMILES: c1ccc2c(c1)-c1c(Nc3cccc4oc5ccccc5c34)cccc1C21CCCCC1] | 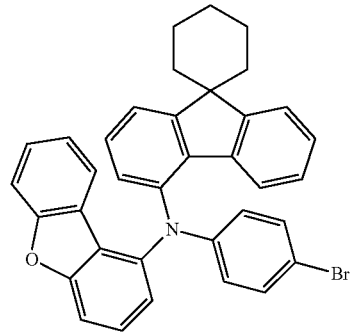 [SMILES: Brc1ccc(N(c2cccc3c2-c2ccccc2C32CCCCC2)c2cccc3oc4ccccc4c23)cc1] | 52 |
| 5p | 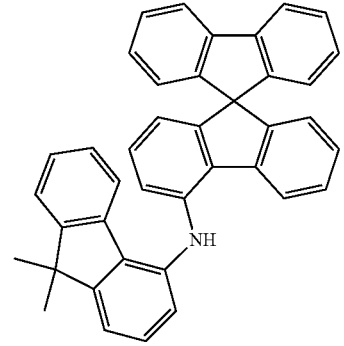 [SMILES: CC1(C)c2ccccc2-c2c(Nc3cccc4c3-c3ccccc3C43c4ccccc4-c4ccccc43)cccc21] | 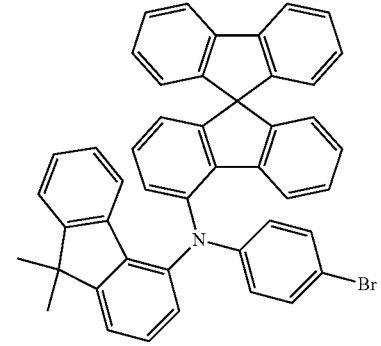 [SMILES: CC1(C)c2ccccc2-c2c(N(c3ccc(Br)cc3)c3cccc4c3-c3ccccc3C43c4ccccc4-c4ccccc43)cccc21] | 48 |
| 5q | 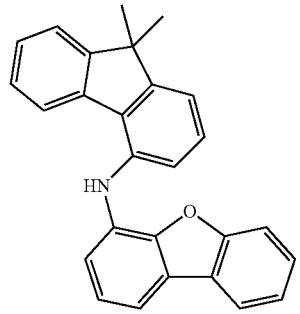 [SMILES: CC1(C)c2ccccc2-c2c(Nc3cccc4c3oc3ccccc34)cccc21] | 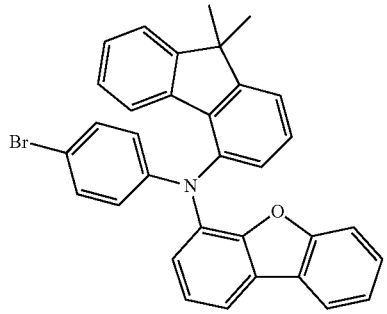 [SMILES: CC1(C)c2ccccc2-c2c(N(c3ccc(Br)cc3)c3cccc4c3oc3ccccc34)cccc21] | 67 |

-continued

| Reactant 3 | Product 5 | Yield [%] |
|---|---|---|
| 5r | | 56 |
| 5s | | 44 |
| 5t | | 21 |

| Reactant 3 | Product 5 | Yield [%] |
|---|---|---|
| 5u | | 49 |

Stage 3: Preparation of biphenyl-4-yl[4-(12,12-dimethyl-10,12-dihydro-10-azaindeno[2,1-b]fluoren-7-yl)phenyl](9,9-dimethyl-9H-fluoren-4-yl)amine 7a In a 2 l four-neck flask, 43.5 g (135 mmol, 1.00 eq) of the amine 5a are initially charged together with 61.0 g (149 mmol, 1.10 eq) of 5,7-dihydro-7,7-dimethyl-2-(44,55-tetramethyl-1,3,2-dioxaborolan-2-yl)-indeno[2,1-b]carbazole [1357286-77-1] and 53.9 g (270 mmol, 2.00 eq) of tripotassium phosphate [7778-53-2], in 300 ml each of toluene and dioxane, and 150 ml of demineralized water, and degassed for 30 minutes. Subsequently, 1.21 g (5.40 mmol, 0.04 eq) of palladium(II) acetate [3375-31-3] and 2.47 g (8.10 mmol, 0.06 eq) of tri-o-tolylphosphine [6163-58-2] are added and the mixture is heated under reflux overnight. After the reaction has ended, a further 100 ml of water are added and the aqueous phase is removed. The aqueous extract is extracted three times with toluene, the combined organic phases are dried over sodium sulphate and the solvent is removed on a rotary evaporator. After recrystallization from toluene/heptane, 81.2 g (113 mmol, 84%) of the desired product 7a are obtained.

The following are prepared analogously:

| Reactant 5 | Product 7 | Yield [%] |
|---|---|---|
| 7b | | 67 |

| Reactant 5 | Product 7 | Yield [%] |
|---|---|---|
| 7c | | 81 |
| 7d | | 89 |

-continued
| Reactant 5 | Product 7 | Yield [%] |
|---|---|---|
| 7e 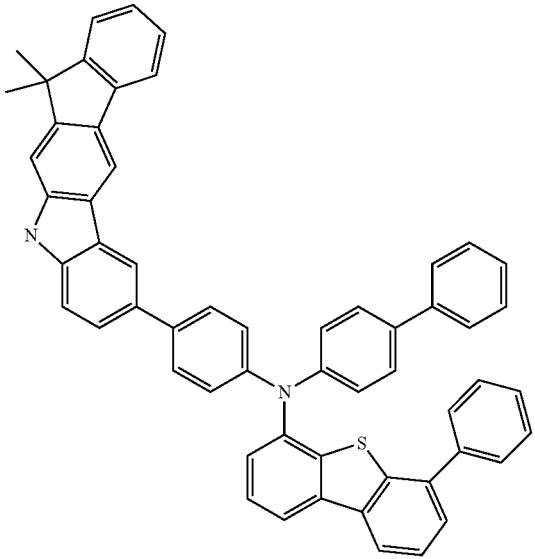 [SMILES: CC1(C)c2ccccc2-c2cc3c(cc21)[nH]c1ccc(-c2ccc(N(c4ccc(-c5ccccc5)cc4)c4cccc5c4sc4c(-c6ccccc6)cccc45)cc2)cc13] | 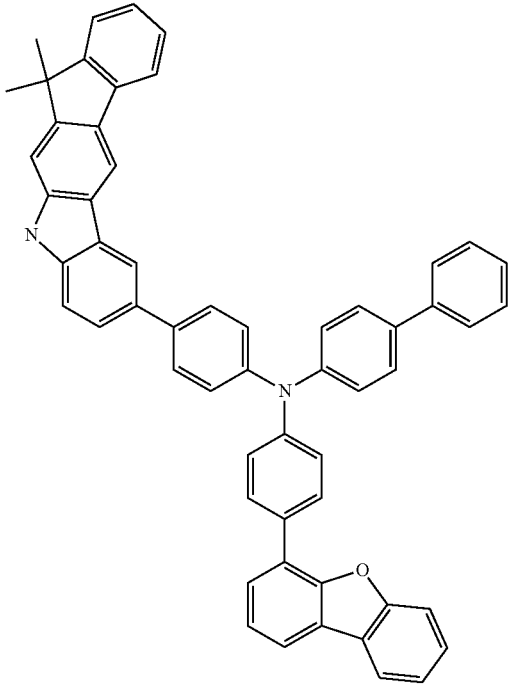 [SMILES: CC1(C)c2ccccc2-c2cc3c(cc21)[nH]c1ccc(-c2ccc(N(c4ccc(-c5ccccc5)cc4)c4ccc(-c5cccc6c5oc5ccccc56)cc4)cc2)cc13] | 77 |
| 7f | | 67 |

| | Reactant 5 | Product 7 | Yield [%] |
|---|---|---|---|
| 7g | 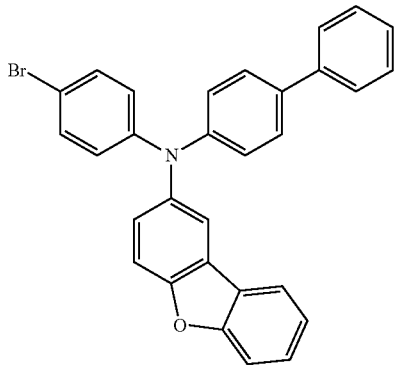 [SMILES: Brc1ccc(N(c2ccc(-c3ccccc3)cc2)c2ccc3oc4ccccc4c3c2)cc1] | 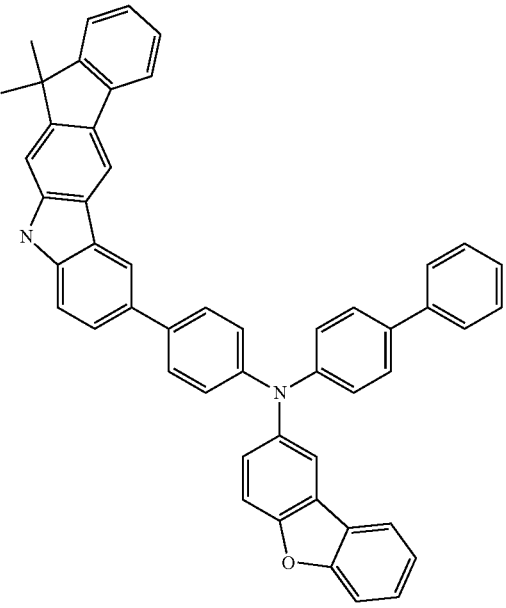 [SMILES: CC1(C)c2ccccc2-c2cc3c(cc21)[nH]c1ccc(-c2ccc(N(c4ccc(-c5ccccc5)cc4)c4ccc5oc6ccccc6c5c4)cc2)cc13] | 45 |
| 7h | 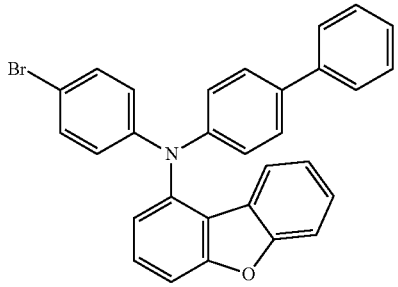 [SMILES: Brc1ccc(N(c2ccc(-c3ccccc3)cc2)c2cccc3oc4ccccc4c23)cc1] | 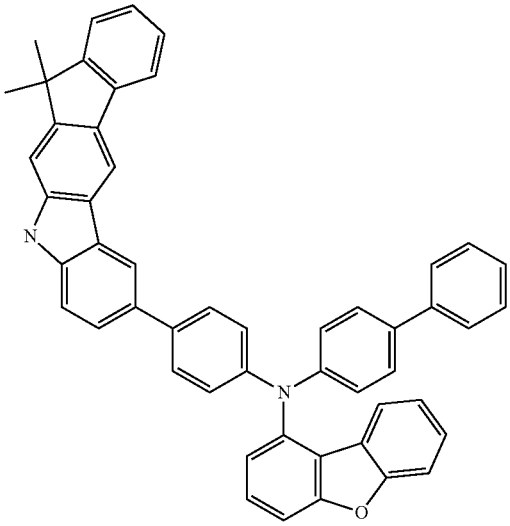 [SMILES: CC1(C)c2ccccc2-c2cc3c(cc21)[nH]c1ccc(-c2ccc(N(c4ccc(-c5ccccc5)cc4)c4cccc5oc6ccccc6c45)cc2)cc13] | 91 |

| Reactant 5 | Product 7 | Yield [%] |
|---|---|---|
| 7i 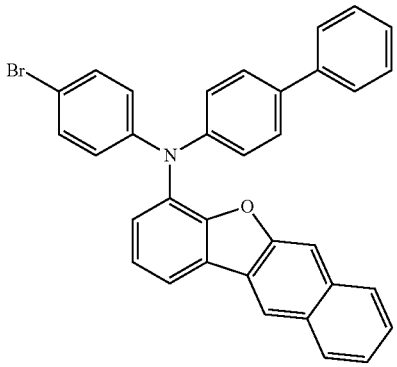 [SMILES: Brc1ccc(N(c2ccc(-c3ccccc3)cc2)c2cccc3c2oc2cc4ccccc4cc23)cc1] | 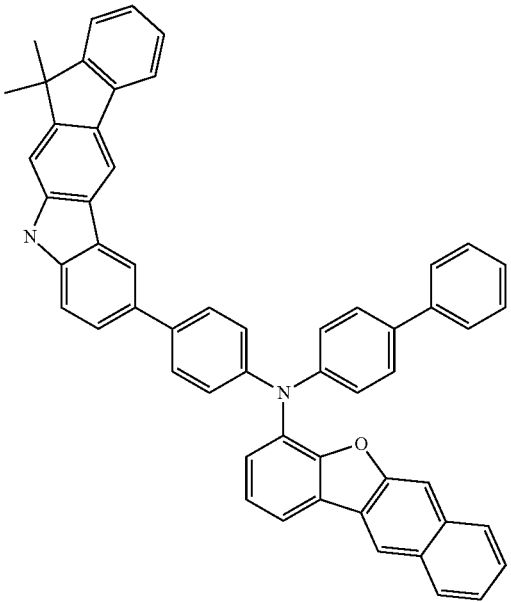 [SMILES: CC1(C)c2ccccc2-c2cc3c(cc21)[nH]c1ccc(-c2ccc(N(c4ccc(-c5ccccc5)cc4)c4cccc5c4oc4cc6ccccc6cc45)cc2)cc13] | 74 |
| 7j 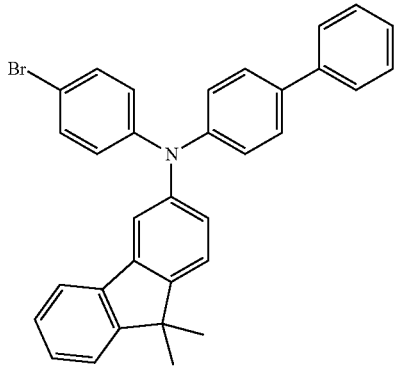 [SMILES: CC1(C)c2ccccc2-c2cc(N(c3ccc(Br)cc3)c3ccc(-c4ccccc4)cc3)ccc21] | 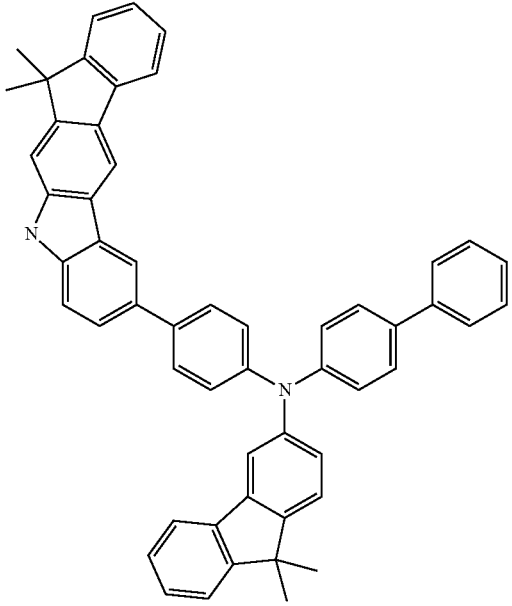 [SMILES: CC1(C)c2ccccc2-c2cc(N(c3ccc(-c4ccccc4)cc3)c3ccc(-c4ccc5[nH]c6cc7c(cc6c5c4)-c4ccccc4C7(C)C)cc3)ccc21] | 66 |

| Reactant 5 | Product 7 | Yield [%] |
|---|---|---|
| 7k | | 58 |
| 7l | | 31 |

| Reactant 5 | Product 7 | Yield [%] |
|---|---|---|
| 7m 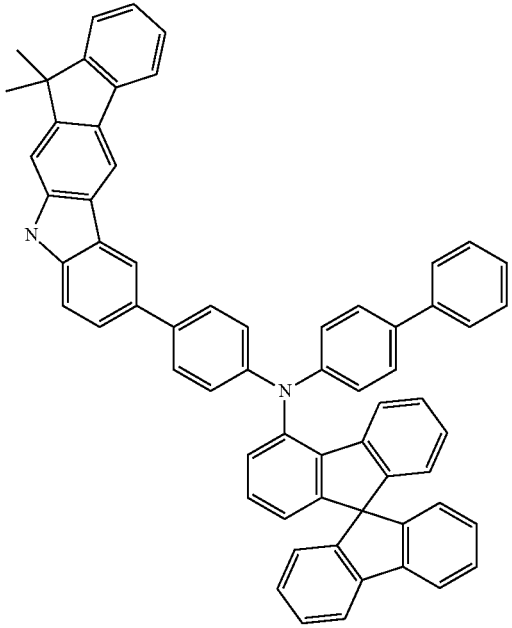 [SMILES: CC1(C)c2ccccc2-c2cc3c(cc21)[nH]c1ccc(-c2ccc(N(c4ccc(-c5ccccc5)cc4)c4cccc5c4-c4ccccc4C54c5ccccc5-c5ccccc54)cc2)cc13] | 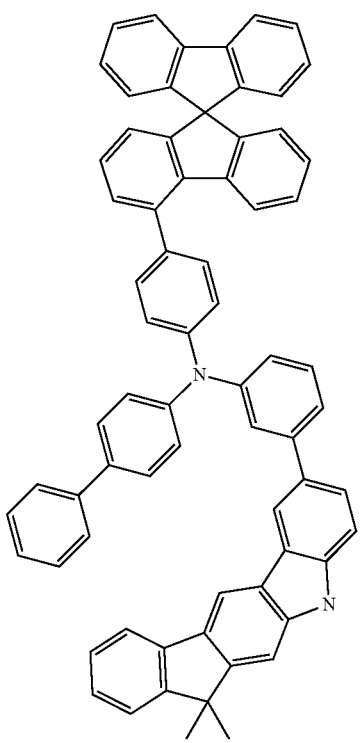 [SMILES: CC1(C)c2ccccc2-c2cc3c(cc21)[nH]c1ccc(-c2cccc(N(c4ccc(-c5ccccc5)cc4)c4ccc(-c5cccc6c5-c5ccccc5C65c6ccccc6-c6ccccc65)cc4)c2)cc13] | 63 |
| 7n | | 54 |

| Reactant 5 | Product 7 | Yield [%] |
|---|---|---|
| 7o 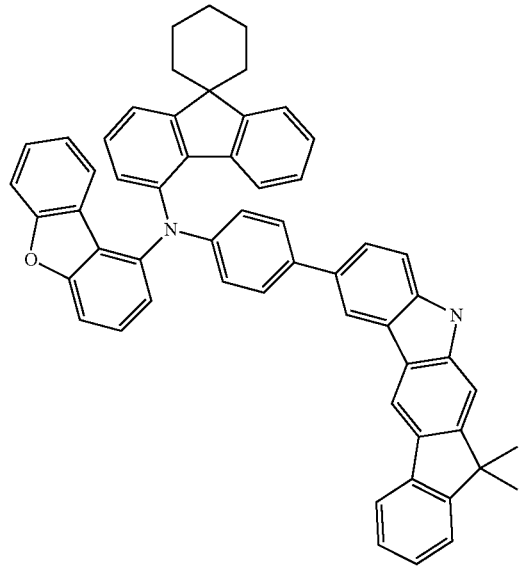 [SMILES: CC1(C)c2ccccc2-c2cc3c(cc21)[nH]c1ccc(-c2ccc(N(c4cccc5c4-c4ccccc4C54CCCCC4)c4cccc5oc6ccccc6c45)cc2)cc13] | 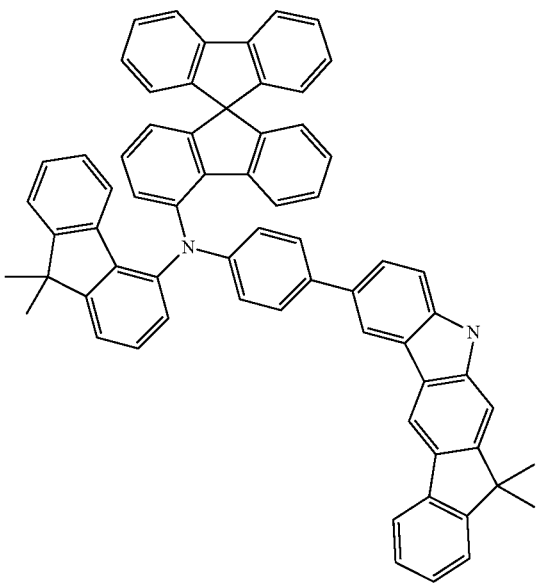 | 87 |
| 7p | | 81 |

-continued
| | Reactant 5 | Product 7 | Yield [%] |
|---|---|---|---|
| 7q | 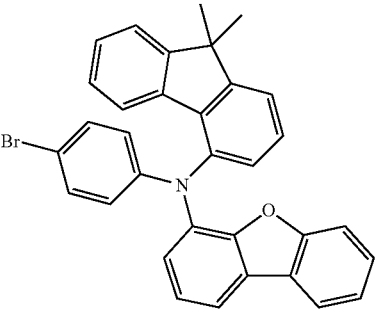 [SMILES: CC1(C)c2ccccc2-c2c(N(c3ccc(Br)cc3)c3cccc4c3oc3ccccc34)cccc21] | | 73 |
| 7r | 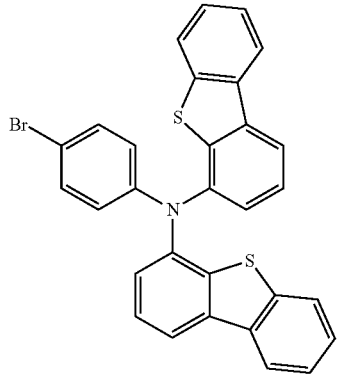 [SMILES: Brc1ccc(N(c2cccc3c2sc2ccccc23)c2cccc3c2sc2ccccc23)cc1] | | 64 |

|  | Reactant 5 | Product 7 | Yield [%] |
|---|---|---|---|
| 7s | 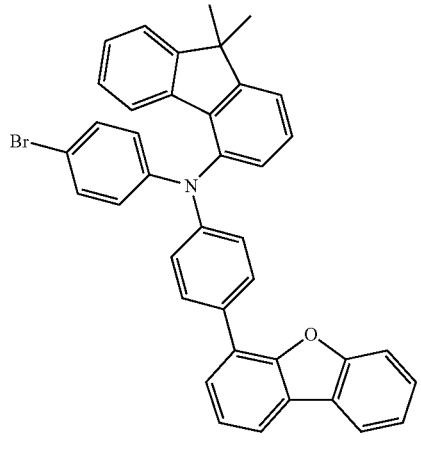 [SMILES: CC1(C)c2ccccc2-c2c(N(c3ccc(Br)cc3)c3ccc(-c4cccc5c4oc4ccccc45)cc3)cccc21] | 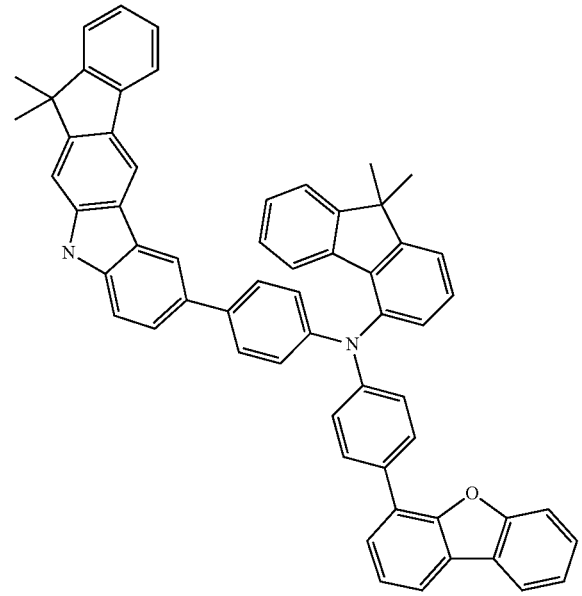 [SMILES: CC1(C)c2ccccc2-c2cc3c(cc21)[nH]c1ccc(-c2ccc(N(c4ccc(-c5cccc6c5oc5ccccc56)cc4)c4cccc5c4-c4ccccc4C5(C)C)cc2)cc13] | 78 |
| 7t | 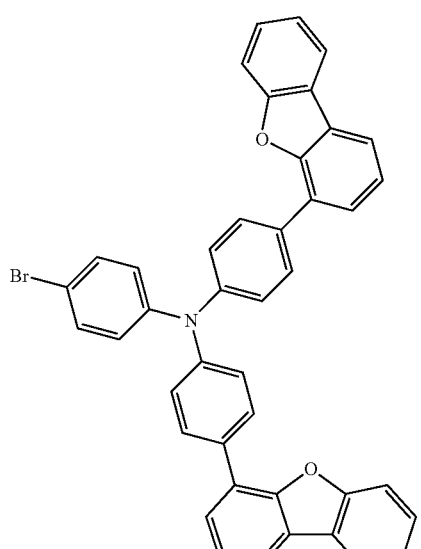 | 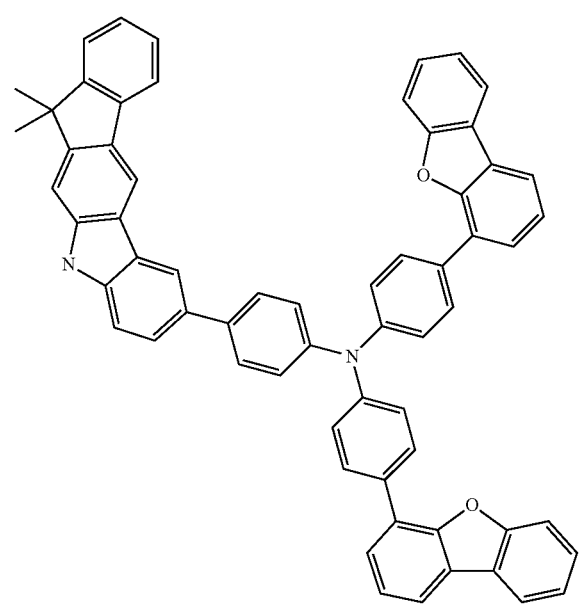 [SMILES: CC1(C)c2ccccc2-c2cc3c(cc21)[nH]c1ccc(-c2ccc(N(c4ccc(-c5cccc6c5oc5ccccc56)cc4)c4ccc(-c5cccc6c5oc5ccccc56)cc4)cc2)cc13] | 93 |

-continued

| Reactant 5 | Product 7 | Yield [%] |
|---|---|---|
| 7u | | 68 |

Stage 4: Preparation of biphenyl-4-yl(9,9-dimethyl-9H-fluoren-4-yl)-[4-(12,12-dimethyl-10-phenyl-10,12-dihydro-10-azaindeno[2,1-b]fluoren-7-yl)phenyl]amine 9a In a 1 l four-neck flask, 20.0 g (25.2 mmol, 1.00 eq) of the intermediate 7a are initially charged together with 11.3 g (55.4 mmol, 2.20 eq) of iodobenzene 8a [591-50-4] and 14.9 g (101 mmol, 4.00 eq) of potassium carbonate [584-08-7] in 300 ml of absolute DMF, and degassed for 30 minutes. Subsequently, 570 mg (2.52 mmol, 0.10 eq) of 1,3-di(2-pyridyl)-1,3-propanedione [10198-89-7] and 480 mg (2.52 mmol, 0.10 eq) of copper(I) iodide [7681-65-4] are added and the mixture is heated under reflux for one day. After the reaction has ended, the reaction mixture is cooled down and transferred gradually into 1000 ml of water. The precipitated solids are filtered off with suction and washed with 400 ml each of saturated ammonium chloride solution, water and 200 ml each of ethanol and heptane. For purification, the solids are subjected to hot extraction with toluene/heptane, recrystallization twice from toluene/heptane and final purification by means of sublimation. 11.2 g (14.1 mmol, 56%) of the desired target compound 9a are obtained with an HPLC purity of >99.9%.

The following are prepared analogously:

| 9b | Reactant 7 | Reactant 8 | Product 9 | Yield [%] |
|---|---|---|---|---|
| | | [591-50-4] | | 34 |

-continued
| Reactant 7 | Reactant 8 | Product 9 | Yield [%] |
|---|---|---|---|
| 9c 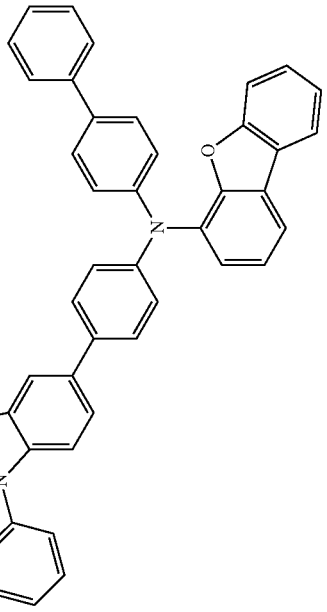 | 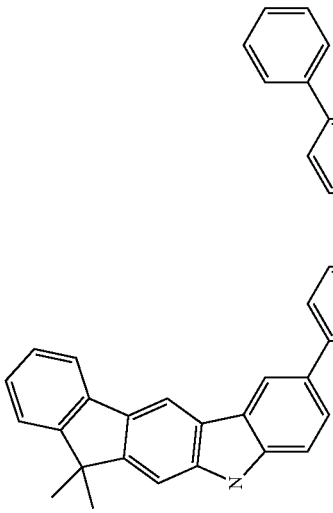 [591-50-4] | 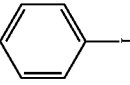 | 51 |

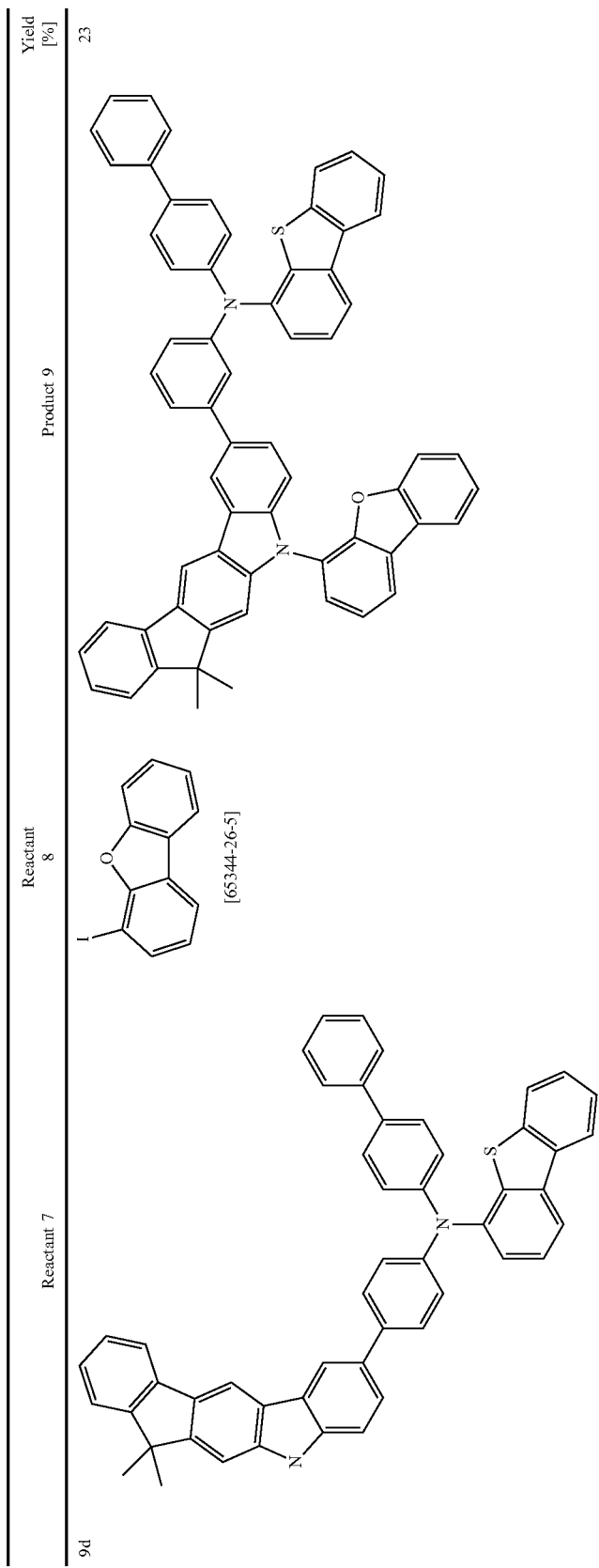

| Reactant 7 | Reactant 8 | Product 9 | Yield [%] |
|---|---|---|---|
| 9e 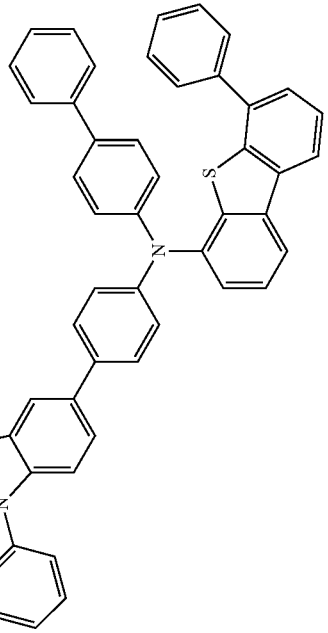 | 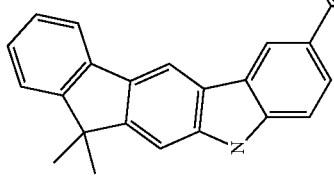 [591-50-4] | 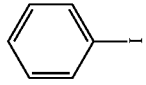 | 37 |

-continued
| Reactant 7 | Reactant 8 | Product 9 | Yield [%] |
|---|---|---|---|
| 9f | [20442-79-9] | | 14 |
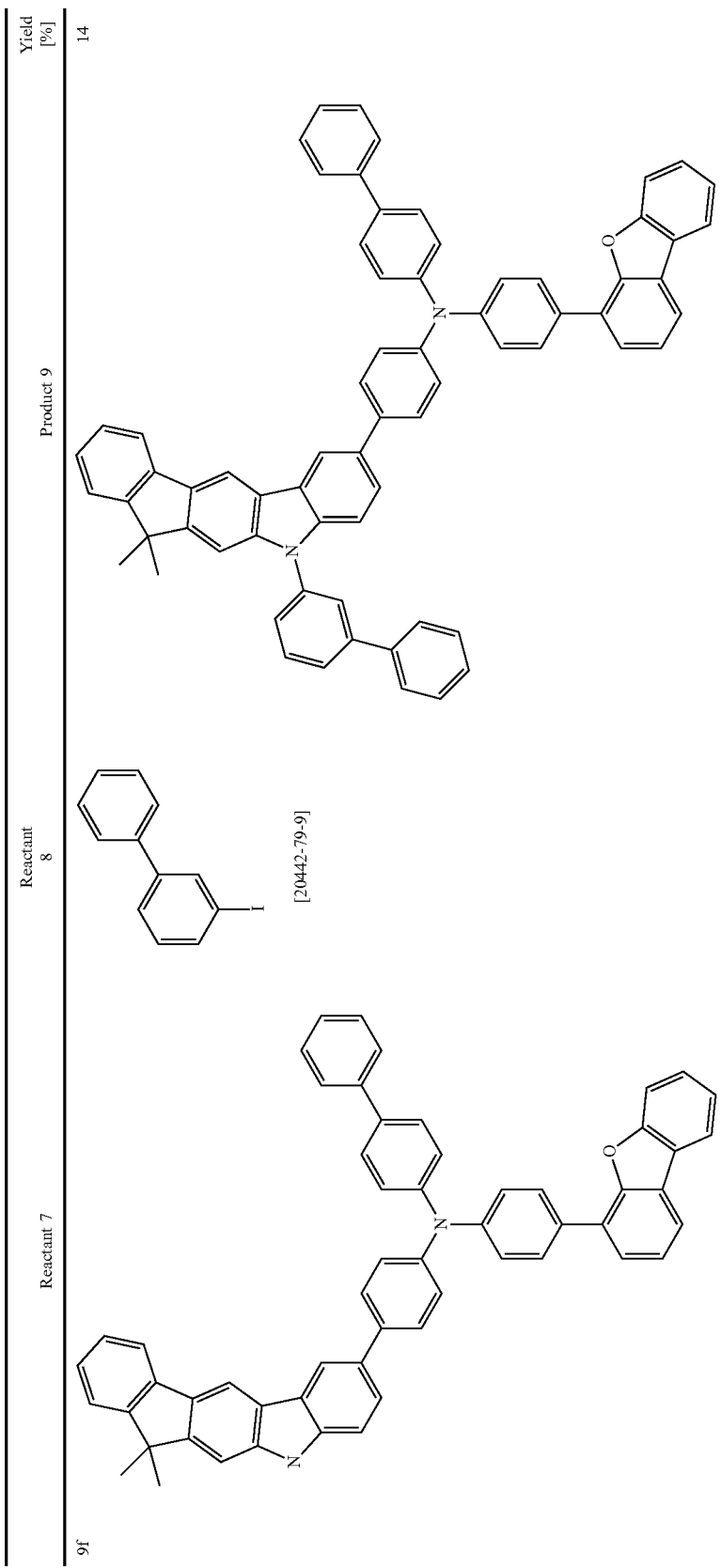

-continued
| Reactant 7 | Reactant 8 | Product 9 | Yield [%] |
|---|---|---|---|
| 9g 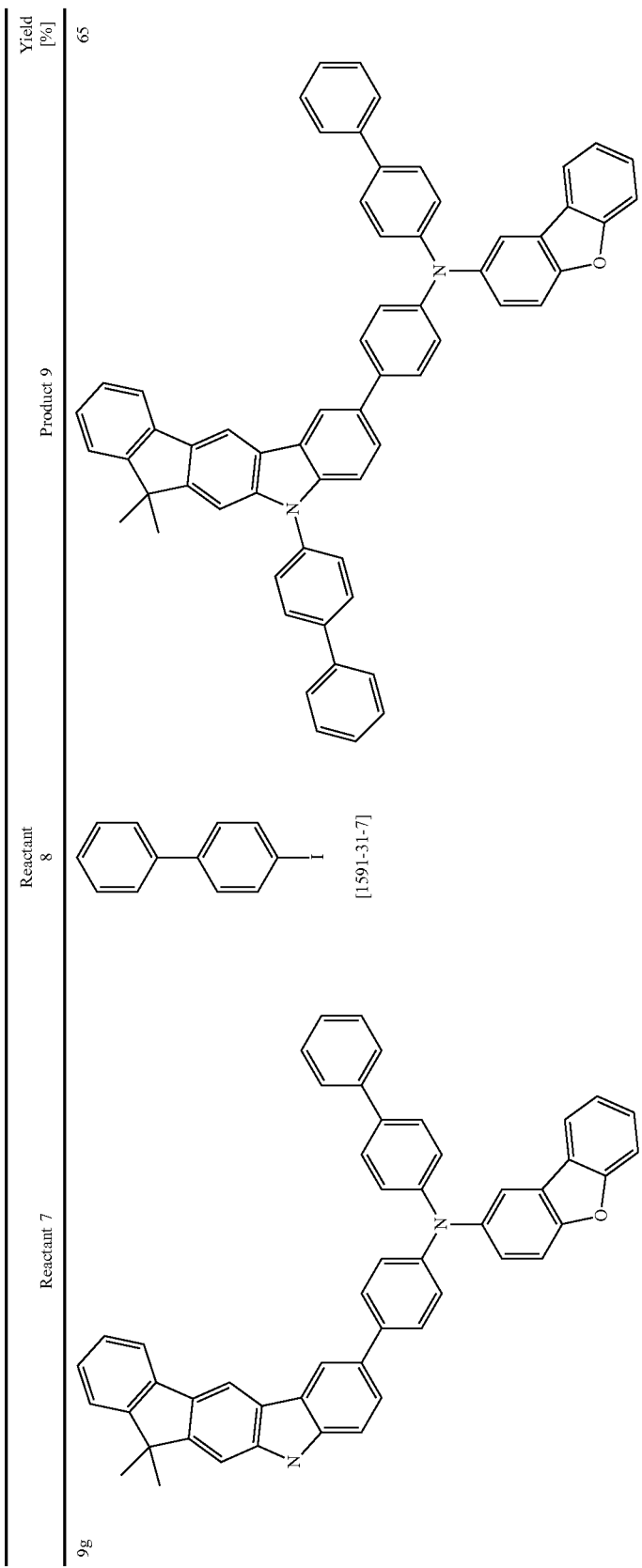 | [1591-31-7] | | 65 |

-continued
| 9h | Reactant 7 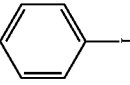 | Reactant 8 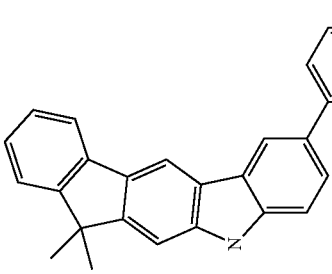 [591-50-4] | Product 9 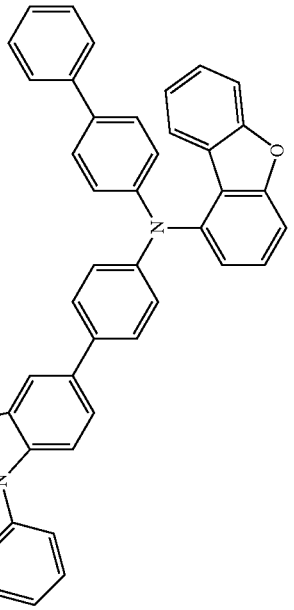 | Yield [%] 47 |

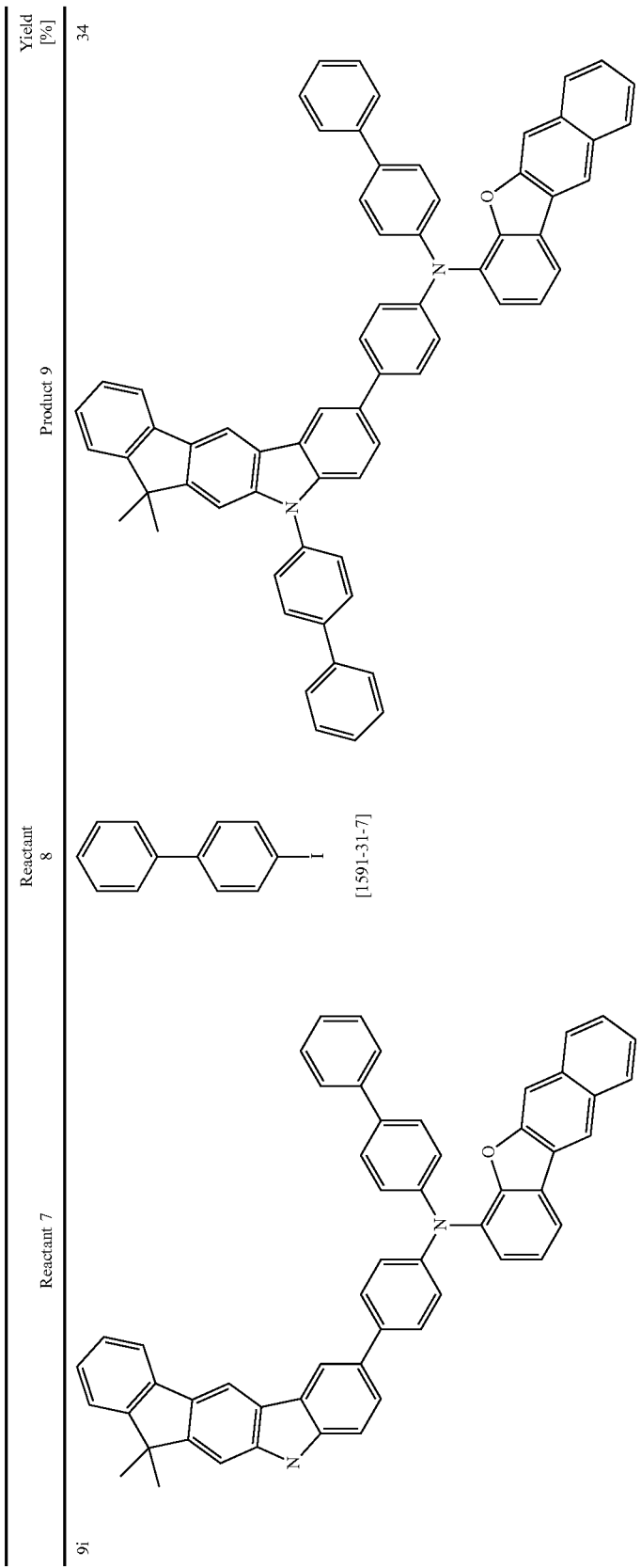

| Reactant 7 | Reactant 8 | Product 9 | Yield [%] |
|---|---|---|---|
| 9j | [1591-31-7] | | 52 |

-continued
| | Reactant 7 | Reactant 8 | Product 9 | Yield [%] |
|---|---|---|---|---|
| 9k | | [20442-79-9] | | 13 |
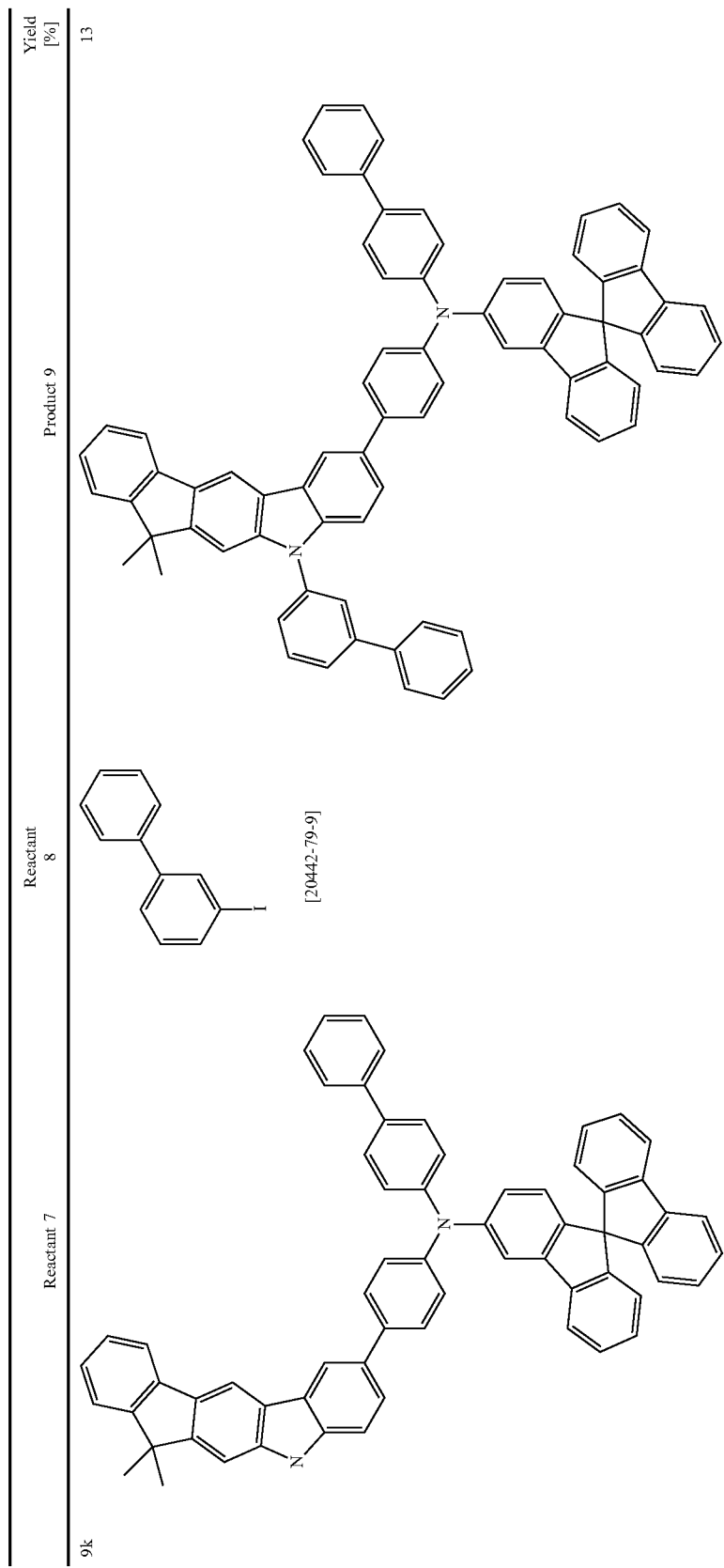

| Reactant 7 | Reactant 8 | Product 9 | Yield [%] |
|---|---|---|---|
| (structure) | (structure) [144981-85-1] | (structure) | 46 |
| 91 | | | |

-continued

| | Reactant 7 | Reactant 8 | Product 9 | Yield [%] |
|---|---|---|---|---|
| 9m | (structure) | (structure) [591-50-4] | (structure) | 61 |

-continued
| 9n | Reactant 7 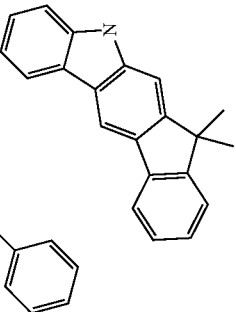 | Reactant 8 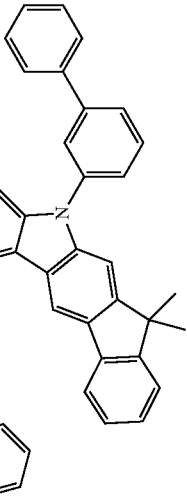 [20442-79-9] | Product 9  | Yield [%] 49 |

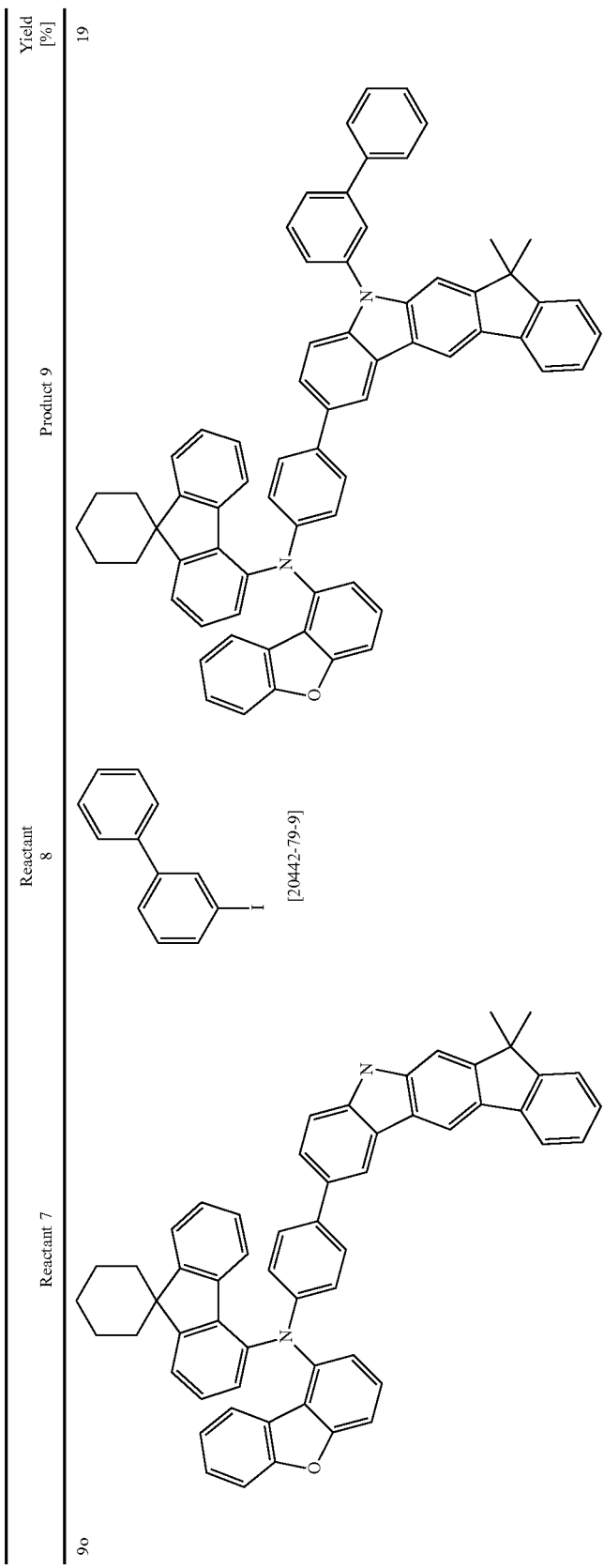

| | Reactant 7 | Reactant 8 | Product 9 | Yield [%] |
|---|---|---|---|---|
| 9p | 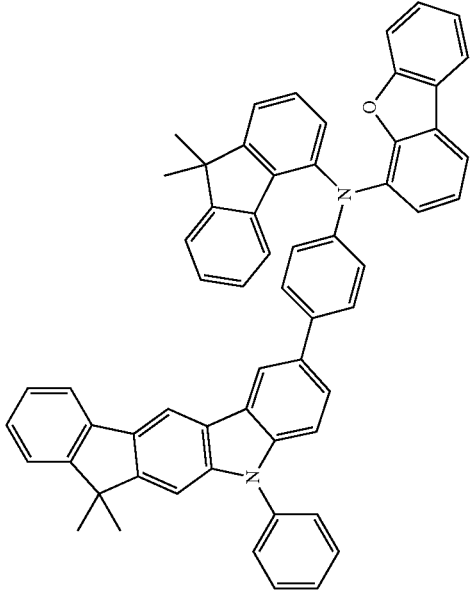 | 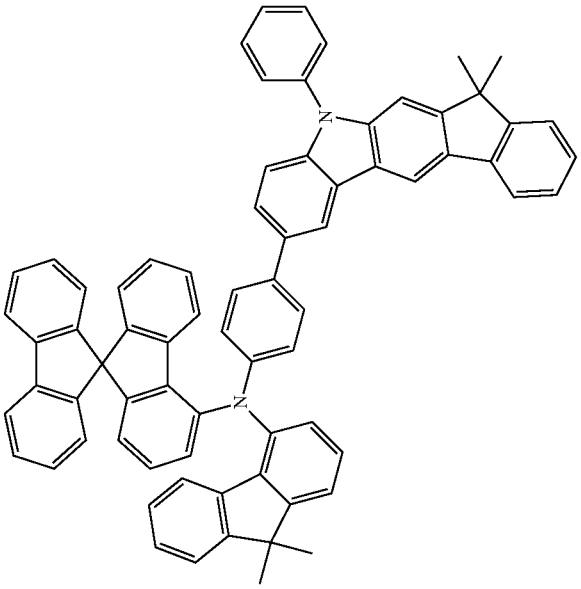 [591-50-4] | 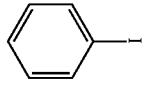 | 33 |
| 9q | 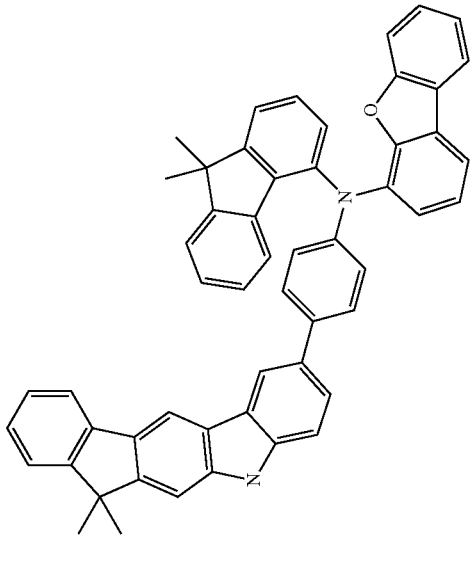 | 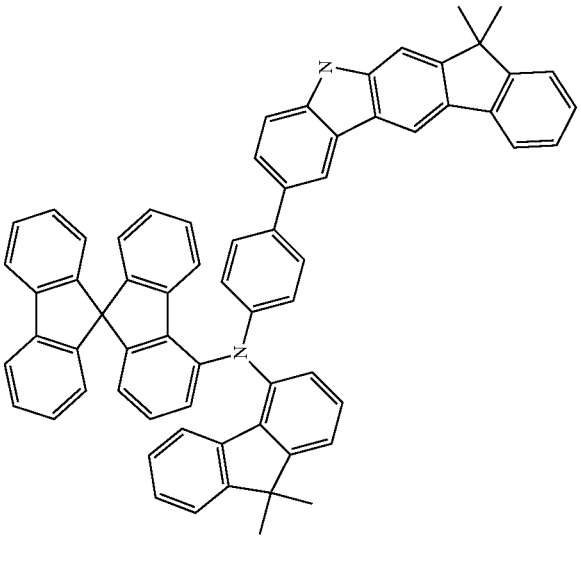 [591-50-4] | 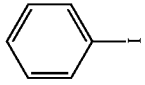 | 23 |

-continued
| | Reactant 7 | Reactant 8 | Product 9 | Yield [%] |
|---|---|---|---|---|
| 9r | 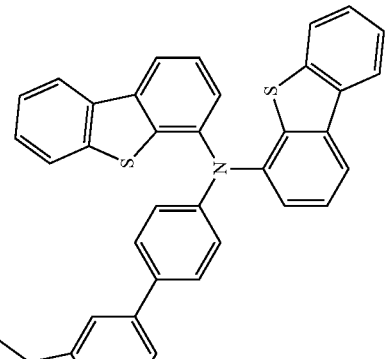 | 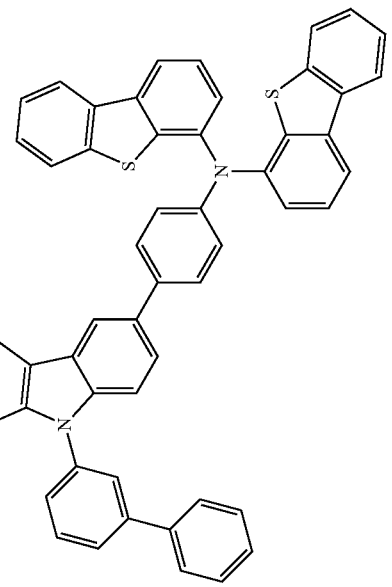  [20442-79-9] | 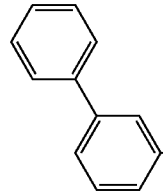 | 21 |

| | -continued | | |
|---|---|---|---|
| | Reactant 7 | Reactant 8 | Product 9 | Yield [%] |
| 9s | 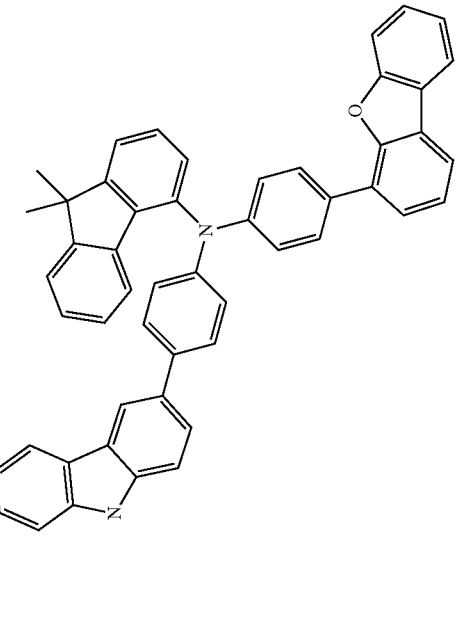 | 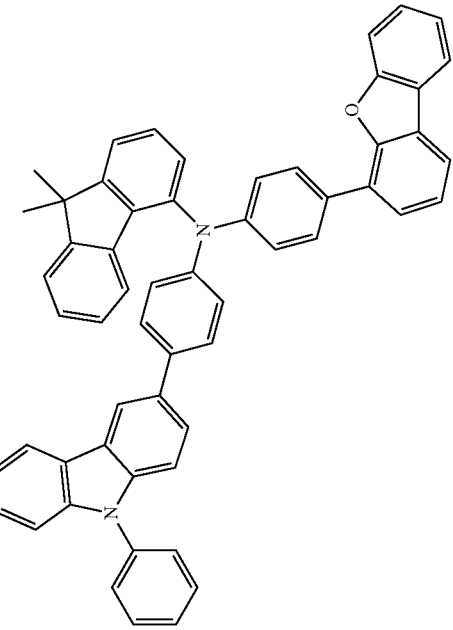
[591-50-4] | 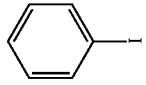 | 55 |

-continued

| Reactant 7 | Reactant 8 | Product 9 | Yield [%] |
|---|---|---|---|
| 9t | [591-50-4] | | 13 |

-continued

| | Reactant 7 | Reactant 8 | Product 9 | Yield [%] |
|---|---|---|---|---|
| 9u | (structure) | (structure) [591-50-4] | (structure) | 63 |

Production of the OLEDs

In examples C1 to C9 and I1 to I20 which follow (see Tables 1 and 2), the data of various OLEDs are presented.

Pretreatment for Examples C1-I20

Glass plaques coated with structured ITO (indium tin oxide) of thickness 50 nm, for improved processing, are coated with 20 nm of PEDOT:PSS (poly(3,4-ethylenedioxythiophene) poly(styrenesulphonate), purchased as CLEVIOS™ PVP AI 4083 from Heraeus Precious Metals GmbH, Germany, spun on from aqueous solution). These coated glass plaques form the substrates to which the OLEDs are applied.

The OLEDs basically have the following layer structure: substrate/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC5:9a:TEG1 (60%:30%:10%) mean here that the material IC5 is present in the layer in a proportion by volume of 60%, 9a in a proportion by volume of 30% and TEG1 in a proportion by volume of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) as a function of luminance, calculated from current-voltage-luminance characteristics (IUL characteristics) assuming Lambertian emission characteristics, and also the lifetime are determined. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. EQE1000 refers to the external quantum efficiency at an operating luminance of 1000 cd/m$^2$. The lifetime LT is defined as the time after which the luminance drops from the starting luminance to a certain proportion $L_1$ in the course of operation with constant current. A FIGURE of $L_{0;j0}$=4000 cd/m$^2$ and $L_1$=70% in Table 2 means that the lifetime reported in the LT column corresponds to the time after which the starting luminance falls from 4000 cd/m$^1$ to 2800 cd/m$^2$. Analogously, $L_{0;j0}$=20 mA/cm$^2$, $L_1$=80% means that the luminance in the course of operation at 20 mA/cm$^2$ falls to 80% of its starting value after the time LT.

The data for the various OLEDs are collated in Table 2. Examples C1 to C29 are comparative examples according to the prior art; examples I1 to I20 show data of OLEDs of the invention.

Some of the examples are elucidated in detail hereinafter, in order to illustrate the advantages of the OLEDs of the invention.

Use of Mixtures of the Invention in the Emission Layer of Phosphorescent OLEDs

The materials of the invention, when used in the emission layer (EML) of phosphorescent OLEDs, give significant improvements over the prior art, particularly with regard to the lifetime of the OLED components. By use, for example, of the inventive compounds 9a, 9b, 9c and 9h in combination with IC5 and the green dopant TEG1, it is possible to observe an increase in lifetime by more than 40% compared to the prior art PA1-PA9 (comparison of examples C1-C9 with I1-I4). This is also true of the further compounds of the invention, as can be inferred from the examples in Table 2. This is a surprising and unforeseeable result, since the compounds according to the prior art are structurally very similar to the compounds of the invention.

Use of Mixtures of the Invention in the Electron Blocker Layer of Phosphorescent OLEDs The materials of the invention, when used as electron blocker material in the electron blocker layer of phosphorescent OLEDs as well, give significant improvements over the prior art, particularly with regard to the lifetime. By use of the compounds of the invention, for example of compounds 9f, 9g, 9j, 9k, 9n, 9o and 9t in examples I7, I8, I10, I11, I14, I15 and I20, it is possible to produce OLEDs having improved lifetimes.

TABLE 1

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| C1 | SpA1 70 nm | HATCN 5 nm | SpMA1 70 nm | — | IC5:PA1:TEG1 (60%:30%:10%) 30 nm | ST2 10 nm | ST2:LiQ (50%:50%) 30 nm | — |
| C2 | SpA1 70 nm | HATCN 5 nm | SpMA1 70 nm | — | IC5:PA2:TEG1 (60%:30%:10%) 30 nm | ST2 10 nm | ST2:LiQ (50%:50%) 30 nm | — |
| C3 | SpA1 70 nm | HATCN 5 nm | SpMA1 70 nm | — | IC5:PA3:TEG1 (60%:30%:10%) 30 nm | ST2 10 nm | ST2:LiQ (50%:50%) 30 nm | — |
| C4 | SpA1 70 nm | HATCN 5 nm | SpMA1 70 nm | — | IC5:PA4:TEG1 (60%:30%:10%) 30 nm | ST2 10 nm | ST2:LiQ (50%:50%) 30 nm | — |
| C5 | SpA1 70 nm | HATCN 5 nm | SpMA1 70 nm | — | IC5:PA5:TEG1 (60%:30%:10%) 30 nm | ST2 10 nm | ST2:LiQ (50%:50%) 30 nm | — |
| C6 | SpA1 70 nm | HATCN 5 nm | SpMA1 70 nm | — | IC5:PA6:TEG1 (60%:30%:10%) 30 nm | ST2 10 nm | ST2:LiQ (50%:50%) 30 nm | — |
| C7 | SpA1 70 nm | HATCN 5 nm | SpMA1 70 nm | — | IC5:PA7:TEG1 (60%:30%:10%) 30 nm | ST2 10 nm | ST2:LiQ (50%:50%) 30 nm | — |
| C8 | SpA1 70 nm | HATCN 5 nm | SpMA1 70 nm | — | IC5:PA8:TEG1 (60%:30%:10%) 30 nm | ST2 10 nm | ST2:LiQ (50%:50%) 30 nm | — |
| C9 | SpA1 70 nm | HATCN 5 nm | SpMA1 70 nm | — | IC5:PA9:TEG1 (60%:30%:10%) 30 nm | ST2 10 nm | ST2:LiQ (50%:50%) 30 nm | — |

TABLE 1-continued

Structure of the OLEDs

| Ex. | HIL thickness | IL thickness | HTL thickness | EBL thickness | EML thickness | HBL thickness | ETL thickness | EIL thickness |
|---|---|---|---|---|---|---|---|---|
| I1 | SpA1 70 nm | HATCN 5 nm | SpMA1 70 nm | — | IC5:9a:TEG1 (60%:30%:10%) 30 nm | ST2 10 nm | ST2:LiQ (50%:50%) 30 nm | — |
| I2 | SpA1 70 nm | HATCN 5 nm | SpMA1 70 nm | — | IC5:9b:TEG1 (60%:30%:10%) 30 nm | ST2 10 nm | ST2:LiQ (50%:50%) 30 nm | — |
| I3 | SpA1 70 nm | HATCN 5 nm | SpMA1 70 nm | — | IC5:9c:TEG1 (60%:30%:10%) 30 nm | ST2 10 nm | ST2:LiQ (50%:50%) 30 nm | — |
| I4 | SpA1 70 nm | HATCN 5 nm | SpMA1 70 nm | — | IC5:9h:TEG1 (60%:30%:10%) 30 nm | ST2 10 nm | ST2:LiQ (50%:50%) 30 nm | — |
| I5 | SpA1 70 nm | HATCN 5 nm | SpMA1 70 nm | — | IC5:9d:TEG1 (60%:30%:10%) 30 nm | ST2 10 nm | ST2:LiQ (50%:50%) 30 nm | — |
| I6 | SpA1 70 nm | HATCN 5 nm | SpMA1 70 nm | — | IC5:9e:TEG1 (60%:30%:10%) 30 nm | ST2 10 nm | ST2:LiQ (50%:50%) 30 nm | — |
| I7 | SpA1 70 nm | HATCN 5 nm | SpMA1 50 nm | 9f 20 nm | IC5:IC3:TEG1 (45%:45%:10%) 30 nm | ST2 10 nm | ST2:LiQ (50%:50%) 30 nm | — |
| I8 | SpA1 70 nm | HATCN 5 nm | SpMA1 50 nm | 9g 20 nm | IC5:IC3:TEG1 (45%:45%:10%) 30 nm | ST2 10 nm | ST2:LiQ (50%:50%) 30 nm | — |
| I9 | SpA1 70 nm | HATCN 5 nm | SpMA1 70 nm | — | IC5:9u:TEG1 (50%:40%:10%) 30 nm | ST2 10 nm | ST2:LiQ (50%:50%) 30 nm | — |
| I10 | SpA1 70 nm | HATCN 5 nm | SpMA1 50 nm | 9j 20 nm | IC5:IC3:TEG1 (45%:45%:10%) 30 nm | ST2 10 nm | ST2:LiQ (50%:50%) 30 nm | — |
| I11 | SpA1 70 nm | HATCN 5 nm | SpMA1 50 nm | 9k 20 nm | IC5:IC3:TEG1 (45%:45%:10%) 30 nm | ST2 10 nm | ST2:LiQ (50%:50%) 30 nm | — |
| I12 | SpA1 70 nm | HATCN 5 nm | SpMA1 70 nm | — | IC5:9l:TEG1 (60%:30%:10%) 30 nm | ST2 10 nm | ST2:LiQ (50%:50%) 30 nm | — |
| I13 | SpA1 70 nm | HATCN 5 nm | SpMA1 50 nm | 9m 20 nm | IC5:9m:TEG1 (60%:30%) 30 nm | ST2 10 nm | ST2:LiQ (50%:50%) 30 nm | — |
| I14 | SpA1 70 nm | HATCN 5 nm | SpMA1 50 nm | 9n 20 nm | IC1:TEG1 (60%:30%:10%) 30 nm | ST2 10 nm | ST2:LiQ (50%:50%) 30 nm | — |
| I15 | SpA1 70 nm | HATCN 5 nm | SpMA1 50 nm | 9o 20 nm | IC1:TEG1 (90%:10%) 30 nm | ST2 10 nm | ST2:LiQ (50%:50%) 30 nm | — |
| I16 | SpA1 70 nm | HATCN 5 nm | SpMA1 50 nm | 9p 20 nm | IC5:9p:TEG1 (90%:10%) 30 nm | ST2 10 nm | ST2:LiQ (50%:50%) 30 nm | — |
| I17 | SpA1 70 nm | HATCN 5 nm | SpMA1 70 nm | — | IC5:9q:TEG1 (60%:30%:10%) 30 nm | ST2 10 nm | ST2:LiQ (50%:50%) 30 nm | — |
| I18 | SpA1 70 nm | HATCN 5 nm | SpMA1 70 nm | — | IC5:9r:TEG1 (60%:30%:10%) 30 nm | ST2 10 nm | ST2:LiQ (50%:50%) 30 nm | — |
| I19 | SpA1 70 nm | HATCN 5 nm | SpMA1 50 nm | 9s 20 nm | IC5:9s:TEG1 (60%:30%:10%) 30 nm | ST2 10 nm | ST2:LiQ (50%:50%) 30 nm | — |
| I20 | SpA1 70 nm | HATCN 5 nm | SpMA1 50 nm | 9t 20 nm | IC5:IC3:TEG1 (45%:45%:10%) 30 nm | ST2 10 nm | ST2:LiQ (50%:50%) 30 nm | — |
| I21 | SpA1 70 nm | HATCN 5 nm | SpMA1 70 nm | — | IC5:9f:TEG1 (60%:30%:10%) 30 nm | ST2 10 nm | ST2:LiQ (50%:50%) 30 nm | — |
| I22 | SpA1 70 nm | HATCN 5 nm | SpMA1 70 nm | — | IC5:9g:TEG1 (60%:30%:10%) 30 nm | ST2 10 nm | ST2:LiQ (50%:50%) 30 nm | — |
| I23 | SpA1 70 nm | HATCN 5 nm | SpMA1 70 nm | — | IC5:9j:TEG1 (60%:30%:10%) 30 nm | ST2 10 nm | ST2:LiQ (50%:50%) 30 nm | — |
| I24 | SpA1 70 nm | HATCN 5 nm | SpMA1 70 nm | — | IC5:9k:TEG1 (60%:30%:10%) 30 nm | ST2 10 nm | ST2:LiQ (50%:50%) 30 nm | — |
| I25 | SpA1 70 nm | HATCN 5 nm | SpMA1 70 nm | — | IC5:9n:TEG1 (60%:30%:10%) 30 nm | ST2 10 nm | ST2:LiQ (50%:50%) 30 nm | — |
| I26 | SpA1 70 nm | HATCN 5 nm | SpMA1 70 nm | — | IC5:9o:TEG1 (60%:30%:10%) 30 nm | ST2 10 nm | ST2:LiQ (50%:50%) 30 nm | — |
| I27 | SpA1 70 nm | HATCN 5 nm | SpMA1 70 nm | — | IC5:9t:TEG1 (60%:30%:10%) 30 nm | ST2 10 nm | ST2:LiQ (50%:50%) 30 nm | — |
| I28 | SpA1 70 nm | HATCN 5 nm | SpMA1 70 nm | — | IC5:9m:TEG1 (60%:30%:10%) 30 nm | ST2 10 nm | ST2:LiQ (50%:50%) 30 nm | — |
| I29 | SpA1 70 nm | HATCN 5 nm | SpMA1 70 nm | — | IC5:9p:TEG1 (60%:30%:10%) 30 nm | ST2 10 nm | ST2:LiQ (50%:50%) 30 nm | — |
| I30 | SpA1 70 nm | HATCN 5 nm | SpMA1 70 nm | — | IC5:9s:TEG1 (60%:30%:10%) 30 nm | ST2 10 nm | ST2:LiQ (50%:50%) 30 nm | — |
| I31 | SpA1 70 nm | HATCN 5 nm | SpMA1 70 nm | — | IC5:9u:TEG1 (60%:30%:10%) 30 nm | ST2 10 nm | ST2:LiQ (50%:50%) 30 nm | — |

TABLE 2

Data of the OLEDs

| Ex. | U1000 (V) | EQE 1000 | $L_0$; $j_0$ | $L_1$ % | LT (h) |
|---|---|---|---|---|---|
| C1 | 3.1 | 15.3% | 20 mA/cm$^2$ | 80 | 130 |
| C2 | 3.2 | 15.4% | 20 mA/cm$^2$ | 80 | 120 |
| C3 | 3.2 | 15.2% | 20 mA/cm$^2$ | 80 | 140 |
| C4 | 3.3 | 15.5% | 20 mA/cm$^2$ | 80 | 110 |

TABLE 2-continued

Data of the OLEDs

| Ex. | U1000 (V) | EQE 1000 | $L_0; j_0$ | $L_1$ % | LT (h) |
|---|---|---|---|---|---|
| C5 | 3.1 | 15.6% | 20 mA/cm² | 80 | 105 |
| C6 | 3.2 | 15.7% | 20 mA/cm² | 80 | 100 |
| C7 | 3.1 | 15.6% | 20 mA/cm² | 80 | 115 |
| C8 | 3.2 | 15.1% | 20 mA/cm² | 80 | 75 |
| C9 | 3.1 | 15.8% | 20 mA/cm² | 80 | 125 |
| I1 | 3.2 | 16.1% | 20 mA/cm² | 80 | 260 |
| I2 | 3.3 | 16.3% | 20 mA/cm² | 80 | 230 |
| I3 | 3.3 | 16.2% | 20 mA/cm² | 80 | 240 |
| I4 | 3.2 | 16.0% | 20 mA/cm² | 80 | 255 |
| I5 | 3.3 | 16.2% | 20 mA/cm² | 80 | 235 |
| I6 | 3.2 | 16.1% | 20 mA/cm² | 80 | 225 |
| I7 | 3.2 | 16.7% | 20 mA/cm² | 80 | 265 |
| I8 | 3.3 | 16.5% | 20 mA/cm² | 80 | 225 |
| I9 | 3.4 | 16.2% | 20 mA/cm² | 80 | 250 |
| I10 | 3.4 | 16.6% | 20 mA/cm² | 80 | 225 |
| I11 | 3.5 | 16.5% | 20 mA/cm² | 80 | 220 |
| I12 | 3.1 | 16.0% | 20 mA/cm² | 80 | 210 |
| I13 | 3.3 | 16.3% | 20 mA/cm² | 80 | 245 |
| I14 | 3.5 | 17.4% | 20 mA/cm² | 80 | 125 |
| I15 | 3.4 | 17.5% | 20 mA/cm² | 80 | 115 |
| I16 | 3.4 | 16.2% | 20 mA/cm² | 80 | 255 |
| I17 | 3.3 | 16.0% | 20 mA/cm² | 80 | 250 |
| I18 | 3.3 | 16.1% | 20 mA/cm² | 80 | 245 |
| I19 | 3.3 | 16.2% | 20 mA/cm² | 80 | 240 |
| I20 | 3.3 | 16.5% | 20 mA/cm² | 80 | 270 |
| I21 | 3.4 | 15.6% | 20 mA/cm² | 80 | 150 |
| I22 | 3.4 | 15.5% | 20 mA/cm² | 80 | 155 |
| I23 | 3.3 | 15.8% | 20 mA/cm² | 80 | 160 |
| I24 | 3.4 | 15.9% | 20 mA/cm² | 80 | 150 |
| I24 | 3.4 | 16.1% | 20 mA/cm² | 80 | 145 |
| I25 | 3.3 | 16.0% | 20 mA/cm² | 80 | 220 |
| I26 | 3.4 | 15.7% | 20 mA/cm² | 80 | 155 |
| I27 | 3.4 | 16.1% | 20 mA/cm² | 80 | 230 |
| I28 | 3.5 | 16.2% | 20 mA/cm² | 80 | 245 |
| I29 | 3.3 | 16.0% | 20 mA/cm² | 80 | 250 |
| I30 | 3.4 | 16.2% | 20 mA/cm² | 80 | 235 |

TABLE 3

Structural formulae of the materials for the OLEDs

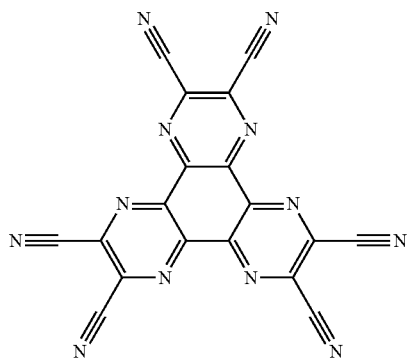

HATCN

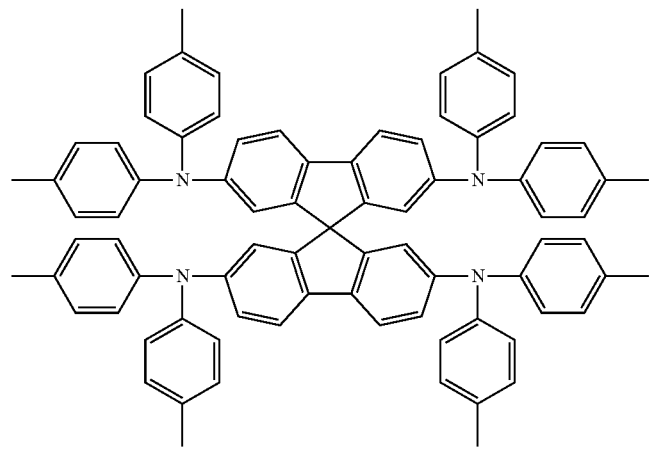

SpA1

TABLE 3-continued
Structural formulae of the materials for the OLEDs
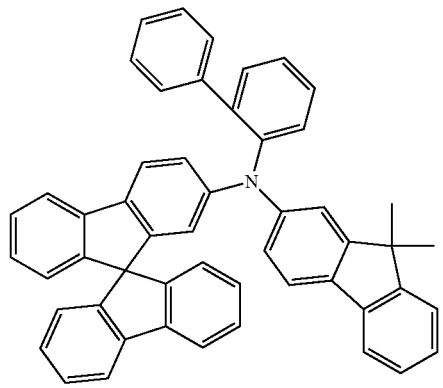
SpMA1
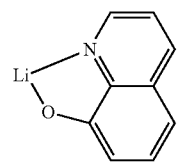
LiQ
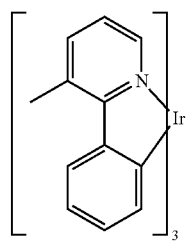
TEG1
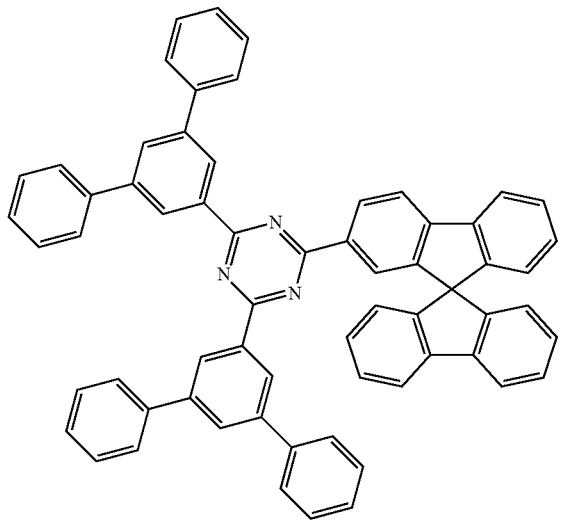
ST2

TABLE 3-continued
Structural formulae of the materials for the OLEDs
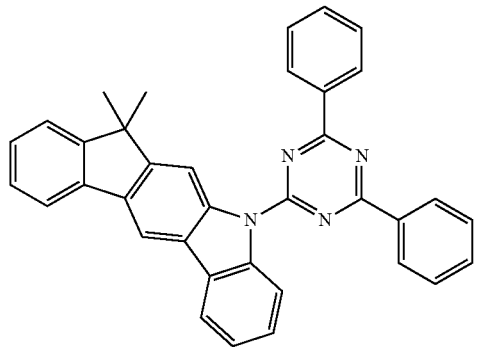
IC1
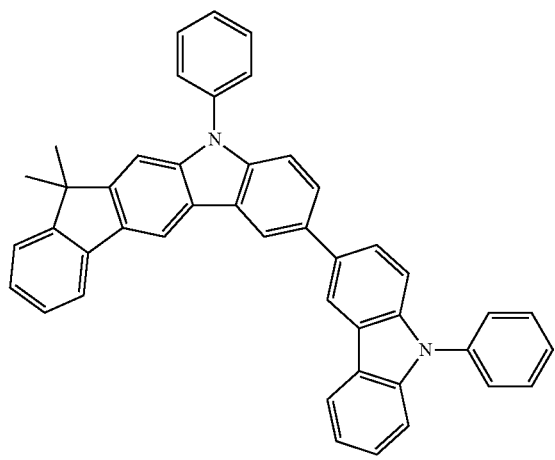
IC3
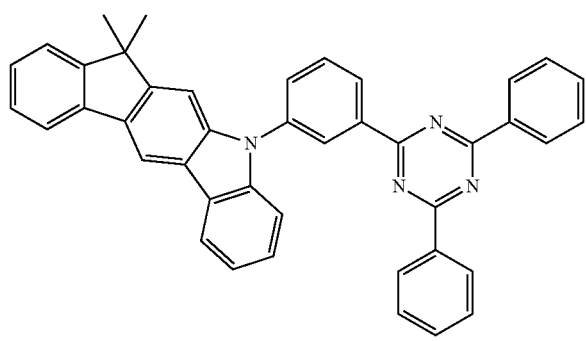
IC5

TABLE 3-continued
Structural formulae of the materials for the OLEDs
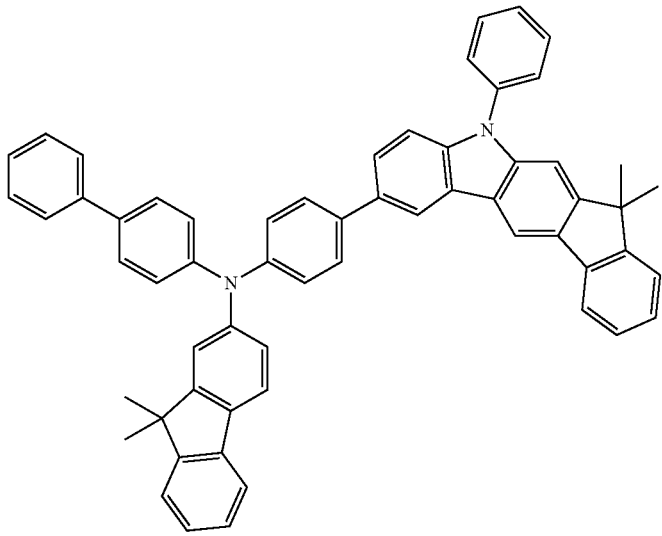
PA1 (according to WO 2012/014500)
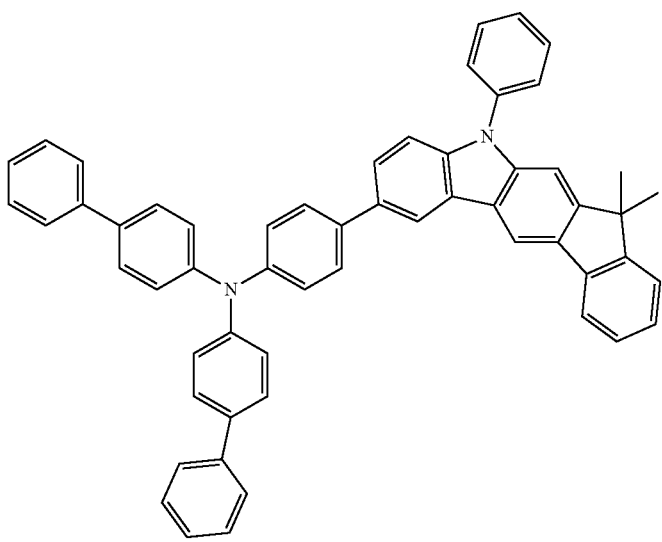
PA2 (according to WO 2012/014500)

TABLE 3-continued
Structural formulae of the materials for the OLEDs
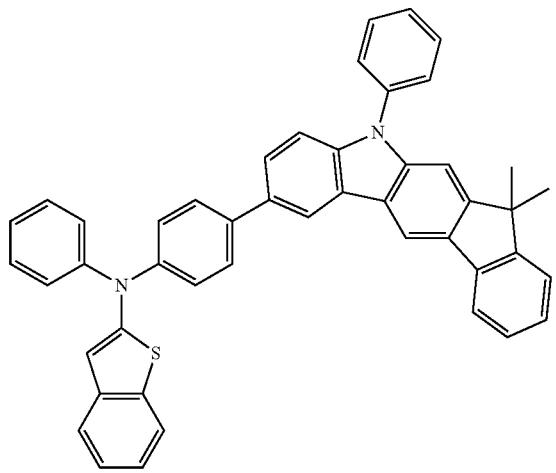
PA3 (according to WO 2012/014500)
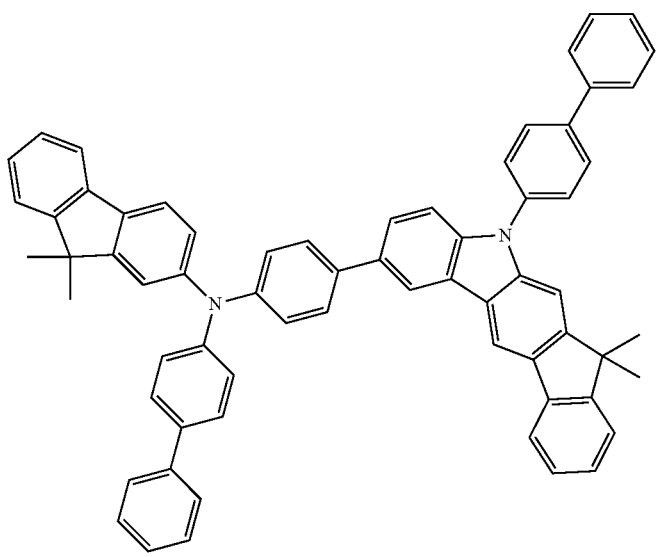
PA4 (according to WO 2010/136109)
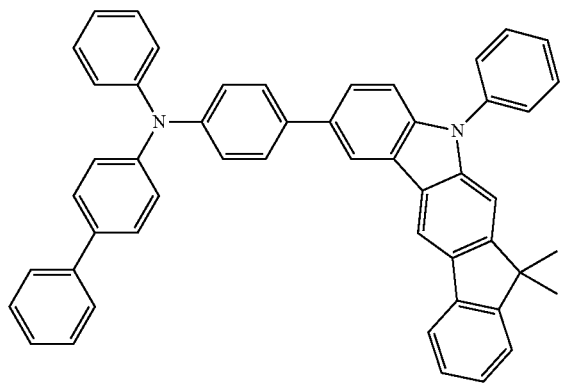
PA5 (according to WO 2010/136109)

TABLE 3-continued
Structural formulae of the materials for the OLEDs
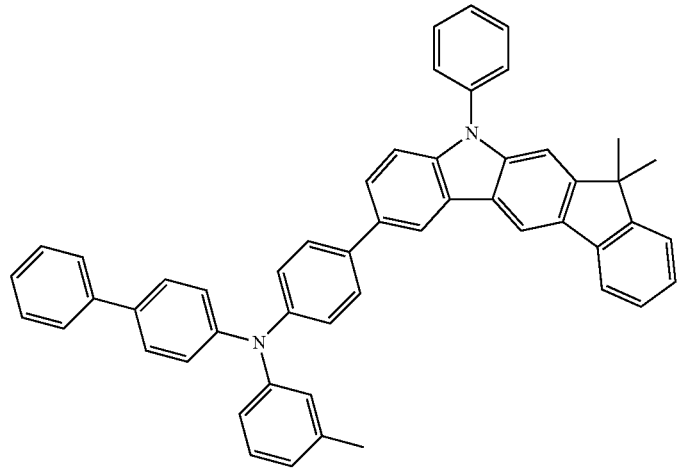
PA6 (according to WO 2010/136109)
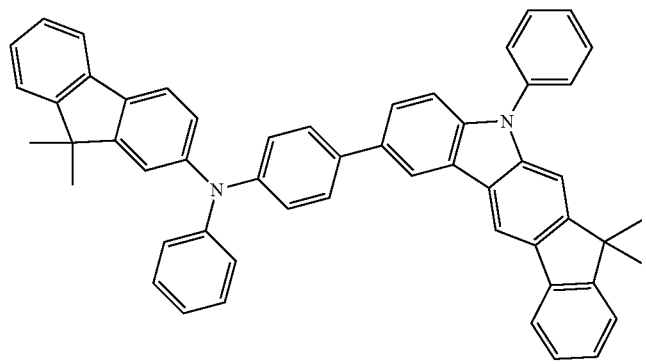
PA7 (according to WO 2010/136109)
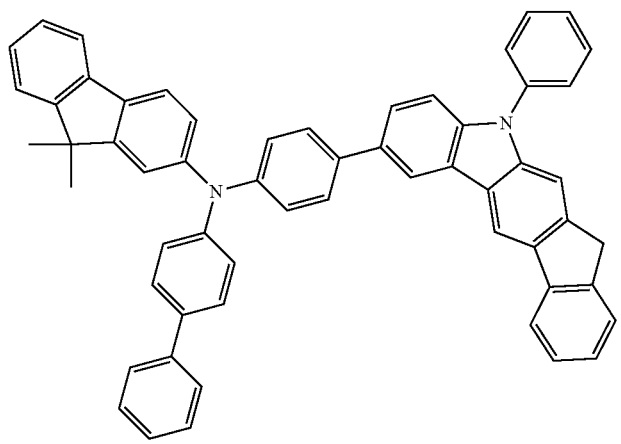
PA8 (according to WO 2010/136109)

TABLE 3-continued
Structural formulae of the materials for the OLEDs
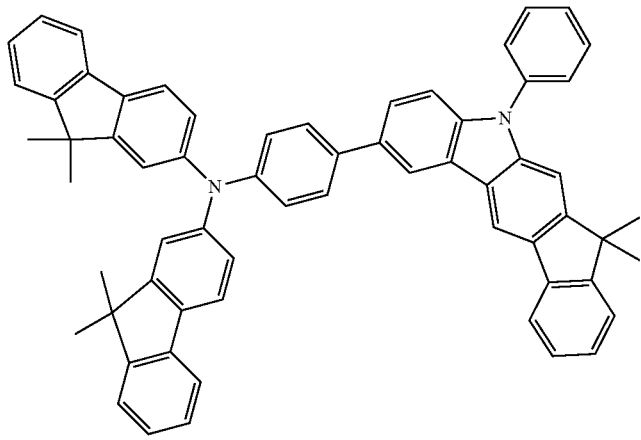
PA9 (according to WO 2012/014500)
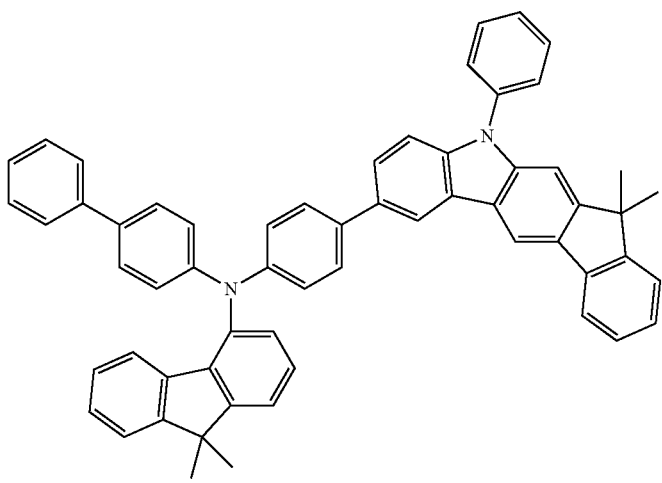
9a
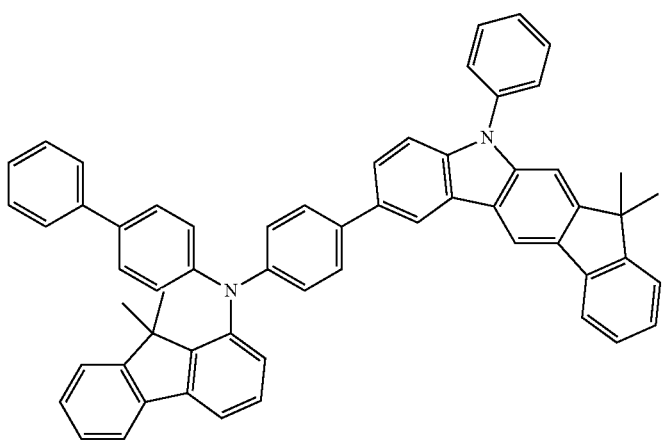
9b TABLE 3-continued
Structural formulae of the materials for the OLEDs
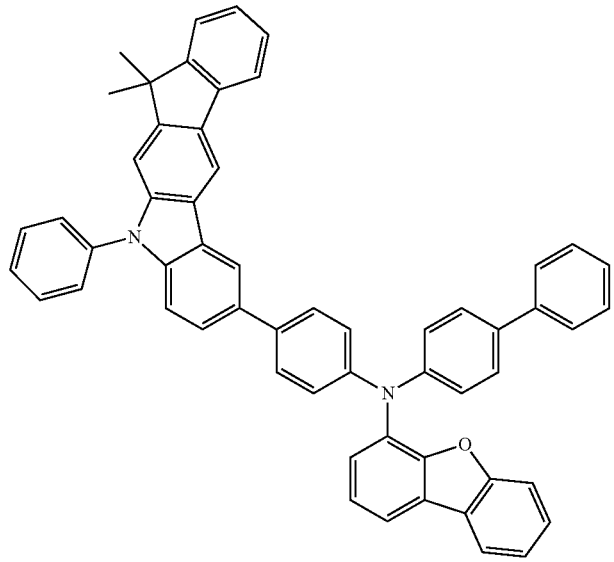 [SMILES: CC1(C)c2ccccc2-c2cc3c4cc(-c5ccc(N(c6ccc(-c7ccccc7)cc6)c6cccc7c6oc6ccccc67)cc5)ccc4n(-c4ccccc4)c3cc21]
9c
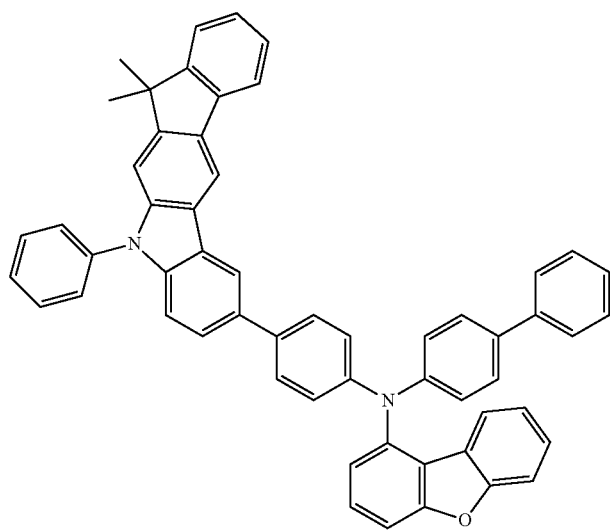
9h TABLE 3-continued
Structural formulae of the materials for the OLEDs
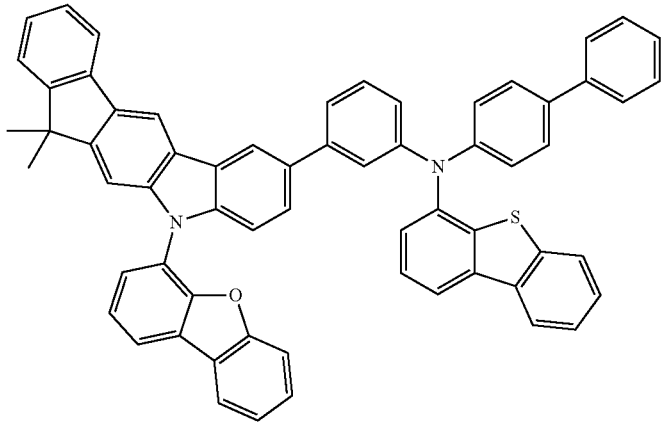
9d
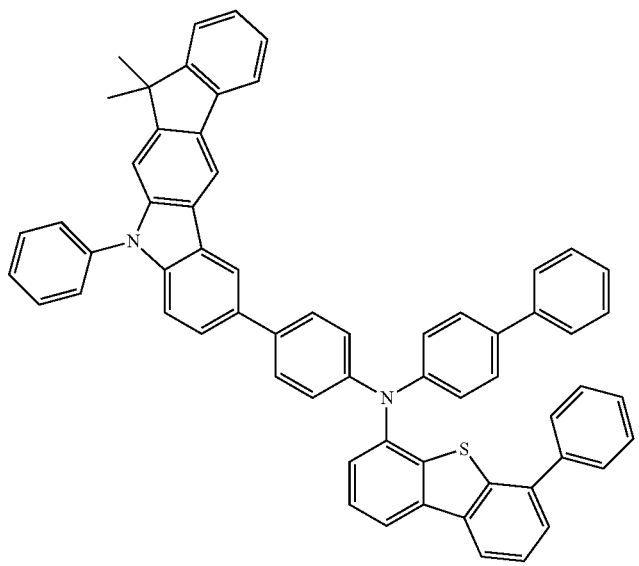 [SMILES: CC1(C)c2ccccc2-c2cc3c4cc(-c5ccc(N(c6ccc(-c7ccccc7)cc6)c6cccc7c6sc6c(-c8ccccc8)cccc67)cc5)ccc4n(-c4ccccc4)c3cc21]
9e TABLE 3-continued
Structural formulae of the materials for the OLEDs
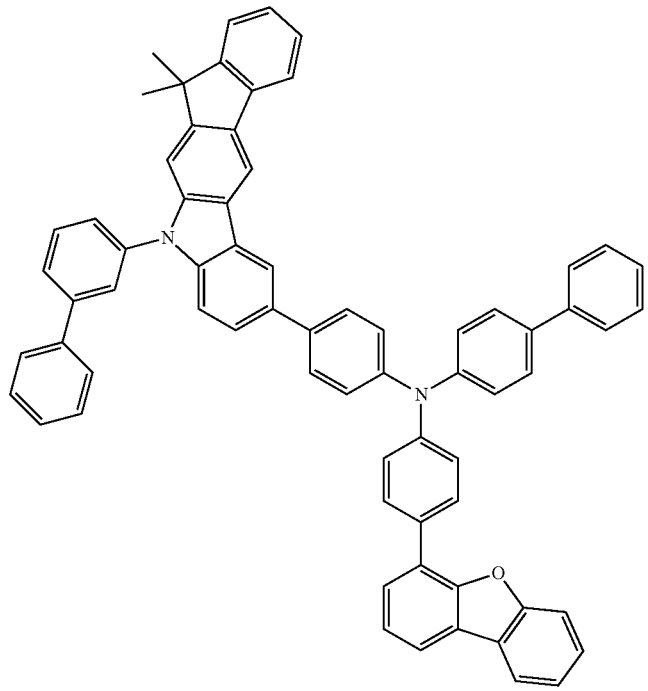 [SMILES: CC1(C)c2ccccc2-c2cc3c4cc(-c5ccc(N(c6ccc(-c7ccccc7)cc6)c6ccc(-c7cccc8c7oc7ccccc78)cc6)cc5)ccc4n(-c4cccc(-c5ccccc5)c4)c3cc21]
9f
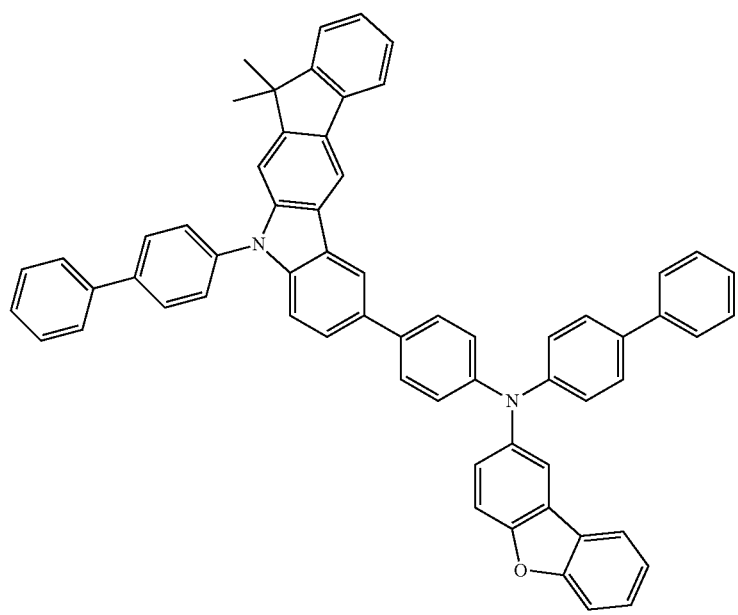 [SMILES: CC1(C)c2ccccc2-c2cc3c4cc(-c5ccc(N(c6ccc(-c7ccccc7)cc6)c6ccc7oc8ccccc8c7c6)cc5)ccc4n(-c4ccc(-c5ccccc5)cc4)c3cc21]
9g TABLE 3-continued
Structural formulae of the materials for the OLEDs
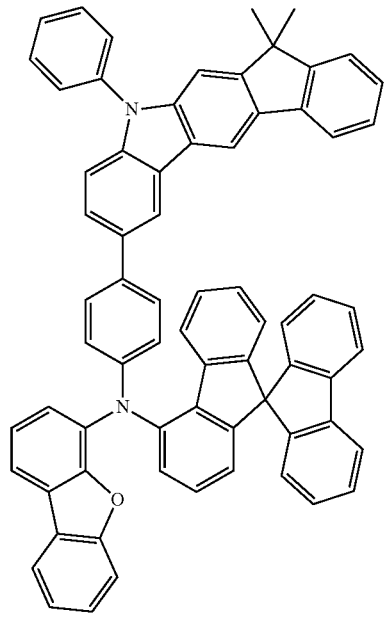
9u
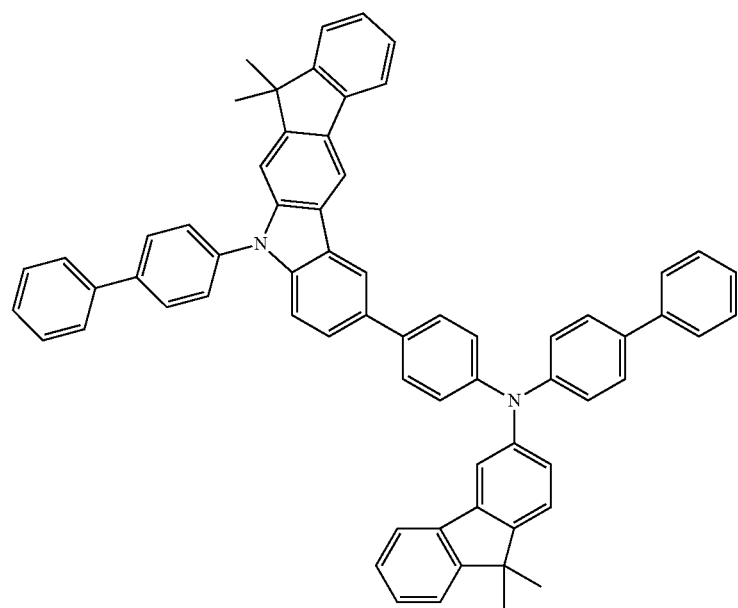 [SMILES: CC1(C)c2ccccc2-c2cc(N(c3ccc(-c4ccccc4)cc3)c3ccc(-c4ccc5c(c4)c4cc6c(cc4n5-c4ccc(-c5ccccc5)cc4)C(C)(C)c4ccccc4-6)cc3)ccc21]
9j TABLE 3-continued
Structural formulae of the materials for the OLEDs
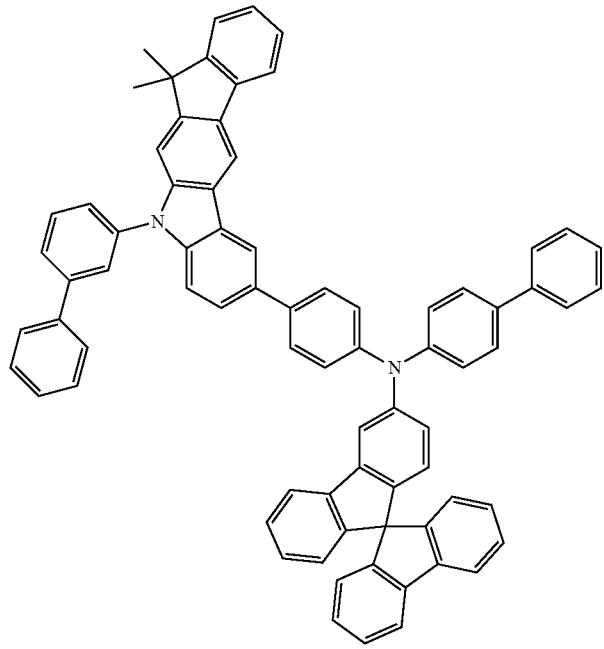 [SMILES: CC1(C)c2ccccc2-c2cc3c4cc(-c5ccc(N(c6ccc(-c7ccccc7)cc6)c6ccc7c(c6)-c6ccccc6C76c7ccccc7-c7ccccc76)cc5)ccc4n(-c4cccc(-c5ccccc5)c4)c3cc21]
9k
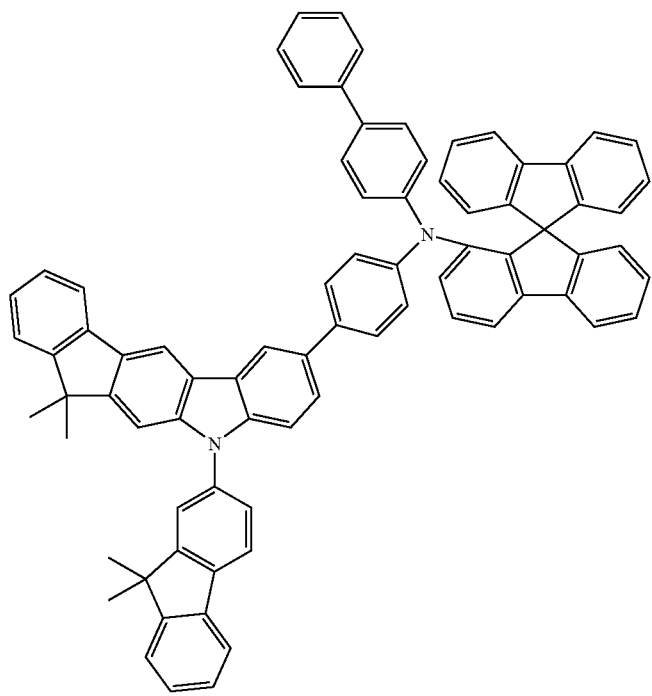

TABLE 3-continued
Structural formulae of the materials for the OLEDs
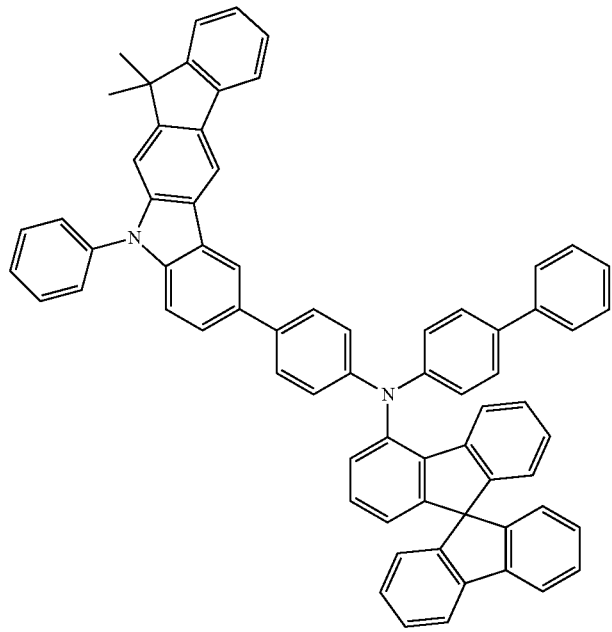 [SMILES: CC1(C)c2ccccc2-c2cc3c4cc(-c5ccc(N(c6ccc(-c7ccccc7)cc6)c6cccc7c6-c6ccccc6C76c7ccccc7-c7ccccc76)cc5)ccc4n(-c4ccccc4)c3cc21]
9m
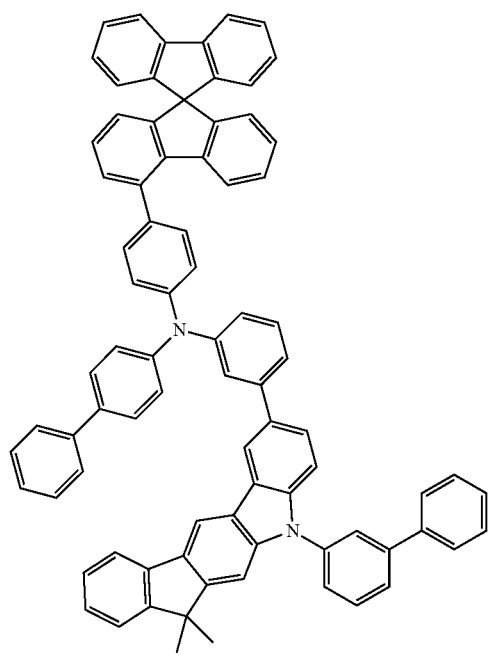
9n TABLE 3-continued
Structural formulae of the materials for the OLEDs
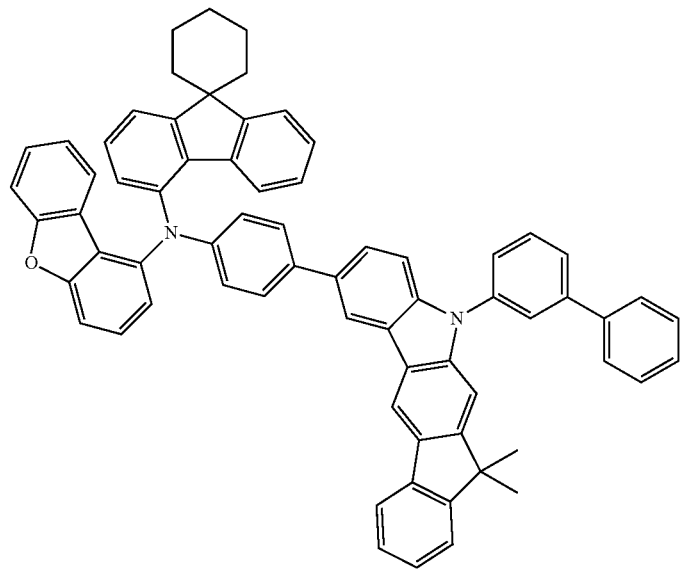 [SMILES: CC1(C)c2ccccc2-c2cc3c4cc(-c5ccc(N(c6cccc7c6-c6ccccc6C76CCCCC6)c6cccc7oc8ccccc8c67)cc5)ccc4n(-c4cccc(-c5ccccc5)c4)c3cc21]
9o
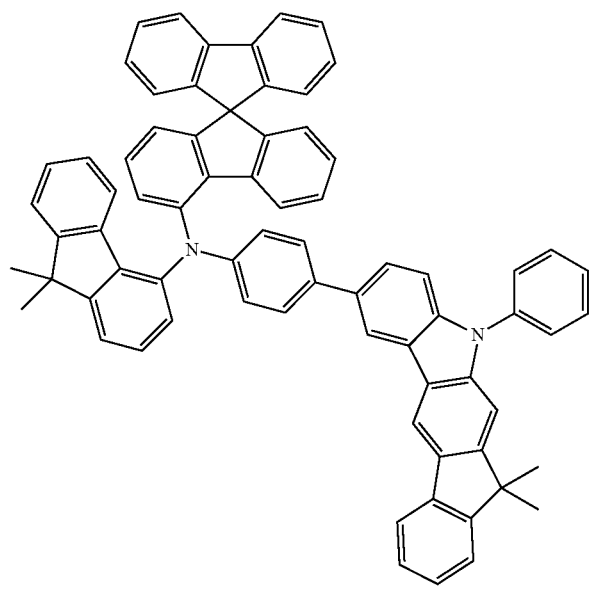 [SMILES: CC1(C)c2ccccc2-c2cc3c4cc(-c5ccc(N(c6cccc7c6-c6ccccc6C7(C)C)c6cccc7c6-c6ccccc6C76c7ccccc7-c7ccccc76)cc5)ccc4n(-c4ccccc4)c3cc21]
9p TABLE 3-continued
Structural formulae of the materials for the OLEDs
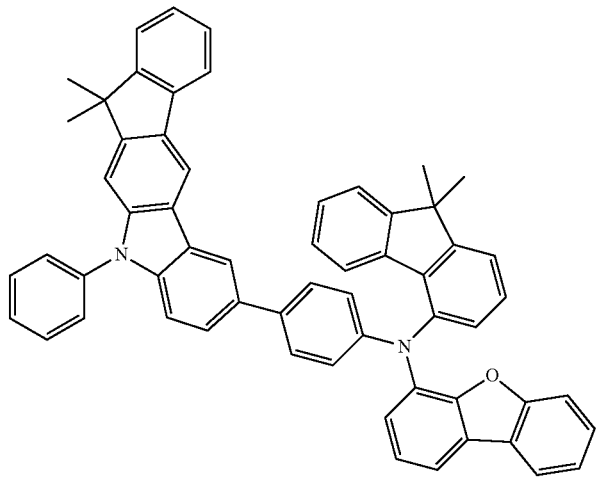
9q
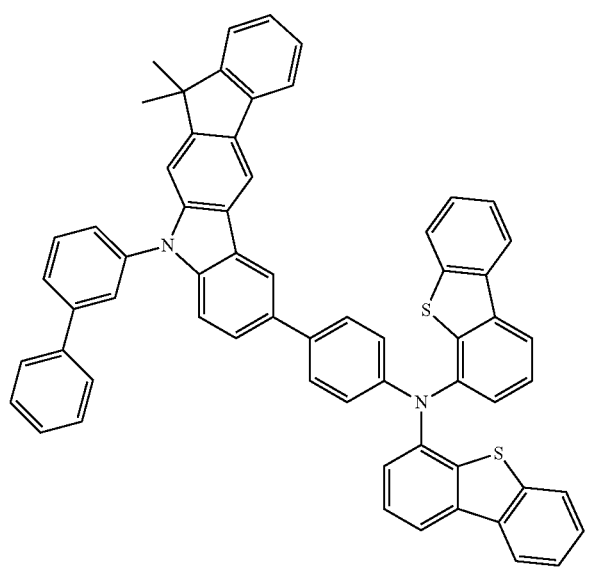 [SMILES: CC1(C)c2ccccc2-c2cc3c4cc(-c5ccc(N(c6cccc7c6sc6ccccc67)c6cccc7c6sc6ccccc67)cc5)ccc4n(-c4cccc(-c5ccccc5)c4)c3cc21]
9r TABLE 3-continued
Structural formulae of the materials for the OLEDs
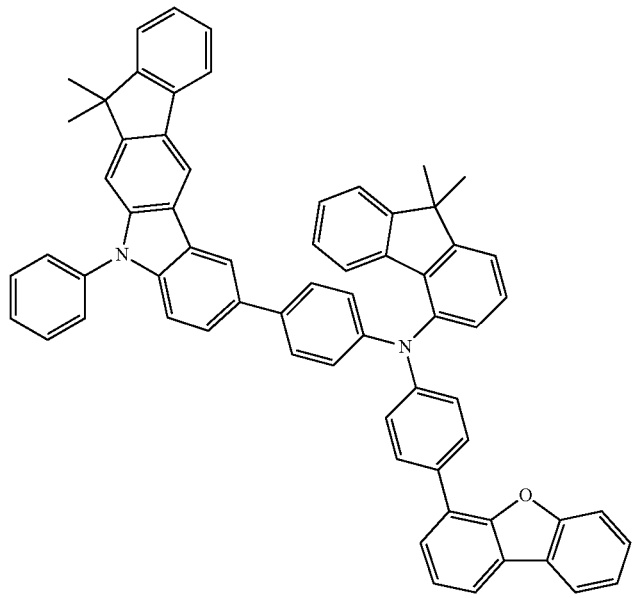 [SMILES: CC1(C)c2ccccc2-c2cc3c4cc(-c5ccc(N(c6ccc(-c7cccc8c7oc7ccccc78)cc6)c6cccc7c6-c6ccccc6C7(C)C)cc5)ccc4n(-c4ccccc4)c3cc21]
9s
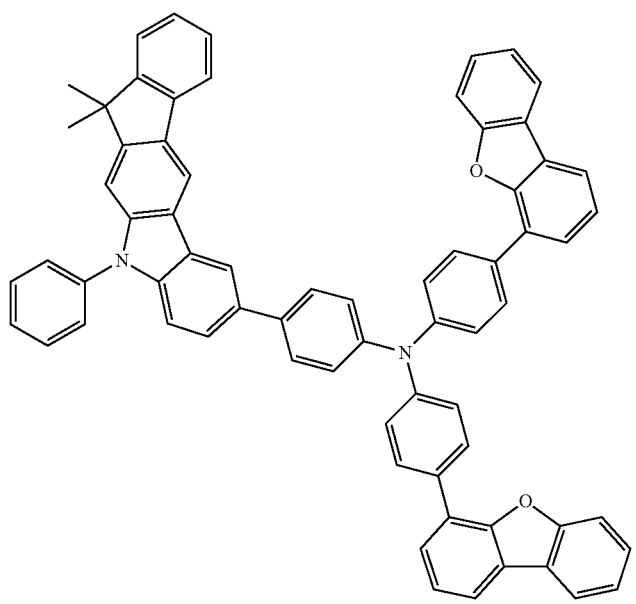 [SMILES: CC1(C)c2ccccc2-c2cc3c4cc(-c5ccc(N(c6ccc(-c7cccc8c7oc7ccccc78)cc6)c6ccc(-c7cccc8c7oc7ccccc78)cc6)cc5)ccc4n(-c4ccccc4)c3cc21]
9t

The invention claimed is:
1. A compound of Formula (3a)

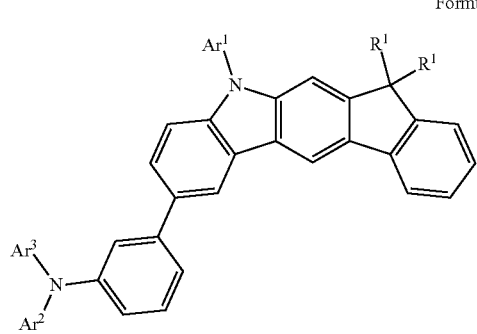

Formula (3a)

where the symbols and indices used are as follows:
Ar¹ is selected from the group consisting of phenyl, biphenyl, terphenyl, quaterphenyl, and fluorenyl;
Ar² is selected from the group consisting of phenyl, biphenyl, terphenyl, quaterphenyl, fluorenyl, spirobifluorenyl, dibenzofuranyl, and dibenzothienyl;
Ar³ is a group of Formula (2a-1), (2a-2) or (2a-3)

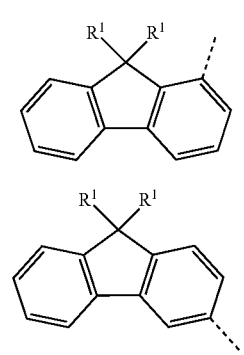

Formula (2a-1)

Formula (2a-2)

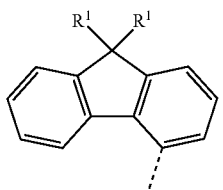

Formula (2a-3)

where the dotted bond indicates the linkage of this group to the nitrogen atom and the fluorene group is joined to the nitrogen atom;
R¹ in formulae (2a-1), (2a-2) or (2a-3) is the same at each instance and is selected from the group consisting a straight-chain alkyl group having 1 to 4 carbon atoms phenyl and two phenyl groups which together form a ring system and hence a spiro system
wherein R¹ radicals on the indenocarbazole are the same or different at each instance and are selected from the group consisting of methyl, phenyl and two phenyl groups which together form a ring system and hence a spiro system.

2. The compound according to claim 1, wherein the R¹ radicals on the indenocarbazole are the same.

3. A formulation comprising at least one compound according to claim 1 and at least one further compound.

4. A formulation comprising at least one compound according to claim 1 and at least one solvent.

5. An electronic device comprising the compound according to claim 1.

6. An organic electroluminescent device which comprises the compound according to claim 1 is used as matrix material for phosphorescent emitters in an emitting layer or in an electron blocker layer or in a hole transport or hole injection layer.

* * * * *